United States Patent [19]
Donahoe et al.

[11] Patent Number: 5,661,126
[45] Date of Patent: Aug. 26, 1997

[54] USE OF MULLERIAN INHIBITING SUBSTANCE FOR TREATING CERTAIN TUMORS AND FOR MODULATING CLASS I MAJOR HISTOCOMPATIBILITY ANTIGEN EXPRESSION

[75] Inventors: Patricia K. Donahoe, Weston, Mass.; Tai Wai Chin, Taipei, Taiwan; Robert L. Parry, Silver Spring, Md.; James Epstein; Richard C. Ragin, both of Boston, Mass.; David T. MacLaughlin, Sangus, Mass.; Edward M. Barksdale, Cincinnati, Ohio

[73] Assignee: The General Hospital Corporation, Boston, Mass.

[21] Appl. No.: 271,252

[22] Filed: Jul. 7, 1994

Related U.S. Application Data

[63] Continuation of Ser. No. 7,125, Jan. 21, 1993, abandoned, which is a continuation-in-part of Ser. No. 299,158, Jan. 19, 1989, abandoned, said Ser. No. 7,125, Jan. 21, 1993, is a continuation-in-part of Ser. No. 901,637, Jun. 19, 1992, abandoned, which is a continuation-in-part of Ser. No. 683,966, Apr. 12, 1991, abandoned.

[51] Int. Cl.$^6$ .................... A61K 38/17; A61K 38/18; C07K 1/12
[52] U.S. Cl. .................... 514/12; 435/68.1; 435/69.1; 530/413
[58] Field of Search ................... 514/12; 530/413

[56] References Cited

U.S. PATENT DOCUMENTS

| | | | |
|---|---|---|---|
| 4,289,690 | 9/1981 | Pestka et al. | 530/351 |
| 4,404,188 | 9/1983 | Donahoe et al. | 530/350 |
| 4,487,833 | 12/1984 | Donahoe et al. | 435/172.2 |
| 4,510,131 | 4/1985 | Donahoe et al. | 530/350 |
| 4,753,794 | 6/1988 | Donahoe | 424/145.1 |
| 4,760,156 | 7/1988 | Hefferman et al. | 556/136 |
| 4,792,601 | 12/1988 | Donahoe et al. | 530/388.24 |
| 4,889,724 | 12/1989 | Kasan et al. | 424/649 |
| 5,010,055 | 4/1991 | Donahoe | 514/8 |
| 5,011,687 | 4/1991 | Donahoe et al. | 424/559 |
| 5,047,336 | 9/1991 | Cate et al. | 435/69.4 |
| 5,198,420 | 3/1993 | Donahoe et al. | 424/131.1 |

FOREIGN PATENT DOCUMENTS

| | | |
|---|---|---|
| WO88/00054 | 1/1988 | WIPO. |
| WO89/06695 | 7/1989 | WIPO. |
| WO92/18152 | 10/1992 | WIPO. |

OTHER PUBLICATIONS

Cate et al., Cold Spring Harbor Symp. Quant. Biol. LI:641–647, (1986).
Fuller et al; Gynecol. Oncol. 17:124–132 (1984).
Wilson et al., Mol. Endocrinol. 7:247–257 (1993).
Hird et al. 1990. *Sever and Cancer*, Charney et al. (Ed.), John Wiley & Sons Ltd., N.Y., pp. 184–189.
Sofer et al. 1983. Bio Techniques, Nov./Dec., pp. 198–203.
Alexander et al., Adoptively Transferred Tumor–Infiltrating Lymphocytes Can Cure Established Metastatic Tumor in Mice and Persist Long–Term In Vivo as Funtional Memory T . . . , *J. Immunol.* 10:389–397 (1991).
Armstrong et al., Prolonged Survival Of Actively Enhanced Rat Renal Allografts Despite Accelerated Cellular Infiltration And Rapid Induction Of Both Class I and Class . . . , *J. Exp. Med.* 164:891–907 (1987).
Blaese et al., Retroviral–Mediated Gene Transfer Into Human Tumor–Infiltrating Lymphocytes (TIL): The First Authorized Protocol For The Use Of Gene Transfer In Man, *Clinical Research* 37(2):599A (1989).
Cate et al., Mullerian–Inhibiting Substance, in *Handbook of Experimental Pharmacology* 95/II:179–210 (1990).
Cate et al., Isolation of the Bovine and Human Genes for Müllerian Inhibiting Substance and Expression of the Human Gene in Animal Cells, *Cells* 45:685–698 (1986).
Chin et al., Human Müllerian Inhibiting Substance Inhibits Tumor Growth *in Vitro* and *in Vivo*, *Cancer Research* 51:2101–2106 (1991).
Culver et al., Lymphocytes as cellular vehicles for gene therapy in mouse and man, *Proc. Natl. Acad. Sci USA* 88:3155–3159 (1991).
Culver et al., In Vivo Gene Transfer with Retroviral Vector–Producer Cells for Treatment of Experimental Brain Tumors, *Science* 256:1550–1552 (1992).
Donahoe, P., Mullerian Inhibiting Substance: A Tyrosine Kinase Inhibitor With Anticancer Effects, *J. Cellular Biochemistry* 12A(Supp.):183 (1988).
Donahoe et al., Mullerian Inhibiting Substance Inhibits Growth of a Human Ovarian Cancer in Nude Mice, *Ann. Surg.* pp. 472–480 (Oct. 1981).
Donahoe et al., Müllerian Duct Regression in the Embryo Correlated with Cytotoxic Activity Against Human Ovarian Cancer, *Science* 205:913–915 (1979).

(List continued on next page.)

*Primary Examiner*—Robert A. Wax
*Assistant Examiner*—Eric Grimes
*Attorney, Agent, or Firm*—Sterne, Kessler, Goldstein & Fox, P.L.L.

[57] ABSTRACT

This application concerns the treatment of certain tumors using an effective amount of the glycoprotein Müllerian Inhibiting Substance (MIS). This application further concerns the treatment of certain tumors using an effective amount of the C-terminal fragment of MIS. Also, this application concerns DNA sequences encoding the C-terminal fragment of MIS, vectors containing the DNA sequence and transformed host cells capable of producing the C-terminal fragment. This application further concerns treating certain tumors by transfecting tumor cells with a gene coding for MIS or the C-terminal fragment of MIS. Gene therapy treatments for inhibiting growth of certain tumors are also provided. Further, this application concerns a method for modulating class I histocompatibility antigens with MIS and EGF.

23 Claims, 21 Drawing Sheets

OTHER PUBLICATIONS

Eisenbach et al, MHC genes and oncogenes controlling the metastatic phenotype of tumor cells, *Cancer Res.* 5:1–18 (1986).

Feldman et al., What Makes a Tumor Cell Metastatic?, *Scientific American* Nov.:60–65, 68 and 85 (1988).

Fuller et al., Mullerian Inhibiting Substance Inhibits Colony Growth of a Human Ovarian Carcinoma Cell Line, *Journal of Clinical Endocrinology and Metabolism* 54(5):1051–1055 (1982).

Fuller et al., Mullerian Inhibiting Substance Reduction of Colony Growth of Human Gynecologic Cancers in a Stem Cell Assay, *Gynecologic Oncology* 22:135–148 (1985).

Fundenburg et al., (Eds.), *Basic and Clinical Immunopathology* 41:305–313 (1986).

Hudson et al., Mullerian Inhibiting Substance (MIS) Slows The Cell Cycle Progression of Human Epidermoid Carcinoma A431 Cells, *J. Cell Biol.* 115(3):176a Abstract No. 1599 (1991).

Hudson et al., Mullerian Inhibiting Substance (MIS) Slows The Cell Cycle Progression Human Epidermoid Carcinoma A431 Cells, *J. Cell Biochem. Supp.* 16B:123 Abstract No. G 112 (1992).

Hudson et al., An Immunoassay to Detect Human Mullerian Inhibiting Substance in Males and Females during Normal Development, *J. Clin. Endocrin. and Metab.* 70(1):16–22 (1990).

Kasid et al., Human gene transfer: Characterization of human tumor–infiltrating lymphocytes as vehicles for retroviral–mediated gene transfer in man, *Proc. Natl. Acad. Sci. USA* 87:473–477 (1990).

MacLaughlin et al., Mullerian Duct Regression and Antiproliferative Bioactivities of Mullerian Inhibiting Substance Reside in it Carboxy–Terminal Domain, *Endocrinology* 131:291–296 (1992).

Miller et al., Redesign of Retrovirus Packaging Cell Lines To Avoid Recombination Leading to Helper Virus Production, *Molecular and Cellular Biology* 6(8):2895–2902 (1986).

Moolten et al., Curability of Tumors Bearing Herpes Thymidine Kinase Genes Transferred by Retroviral Vectors, *J. Natl. Cancer Institute* 82:297–300 (1990).

Mullen et al., Transfer of the bacterial gene for cytosine deaminase to mammalian cells confers lethal sensitivity to 5–fluorocytosine: A negative selection system, *PNAS USA* 89:33–37 (1992).

Ozato et al., Mouse major histocompatibility class I gene expression begins at midsomite stage and is inducible in earlier–stage embryos by interferon, *Proc. Natl. Acad. Sci. USA* 82:2427–2431 (1985).

Parry et al., Recombinant Human Mullerian Inhibiting Substance Inhibits Human Ocular Melonoma Cell Lines *in Vitro* and *in Vivo*, *Cancer Research* 52:1182–1186 (1992).

Pepinsky et al., Proteolytic Processing of Mullerian Inhibiting Substance Produces a Transforming Growth Factor–$\beta$–like Fragment, *J. Biol. Chem.* 263(35):18961–18964 (1988).

Ragin et al., Human Mullerian Inhibiting Substance: Enhanced Purification Imparts Biochemical Stability and Restores Antiproliferative Effects, *Protein Expression and Purification* 3:236–245 (1992).

Ram et al., *In Situ* Retroviral–mediated Gene Transfer for the Treatment of Brain Tumors in Rats, *Cancer Research* 53:83–88 (1993).

Rosenberg et al, A New Approach to the Adoptive Immunotherapy of Cancer with Tumor–Infiltrating Lymphocytes, *Science* 233:1318–1321 (1986).

Rosenberg et al., Use Of Tumor–Infiltrating Lymphocytes And Interleukin–2 In The Immunotherapy of Patients With Metastatic Melanoma, *N. Eng. J. Med.* 319:1676–1680 (1988).

H. Schreiber, in *Fundamental Immunology*, W.F. Paul, Ed., pp. 923, 939–943 (1989).

Speiss et al, In Vivo Antitumor Activity of Tumor–Infiltrating Lymphocytes Expanded in Recombinant Interleukin–2, *J. Natl. Cancer Institute* 79(5):1067–1075 (1987).

Tanaka et al, Reversal of Oncogenesis by the Expression of a Major Histocompatability Complex Class I Gene, *Science* 288:26–30 (1985).

Wallen et al., Minimal Antiproliferative Effect of Recombinant Mullerian Inhibiting Substance on Gynecological Tumor Cell Lines and Tumor Explants, *Cancer Research* 49:2005–2011 (1989).

Ziegler et al, Hypothesis: AIDS Is an Autoimmune Disease Directed at the Immune System and Triggered by a Lymphotropic Retrovirus, *Clin. Immunology and Immunopathology* 41:305–313 (1986).

Semisolid Medium Colony Inhibition Assay

Liquid Medium Colony Inhibition Assay

Liquid Medium Colony Inhibition Assay

Antibody Absorption of MIS Activity

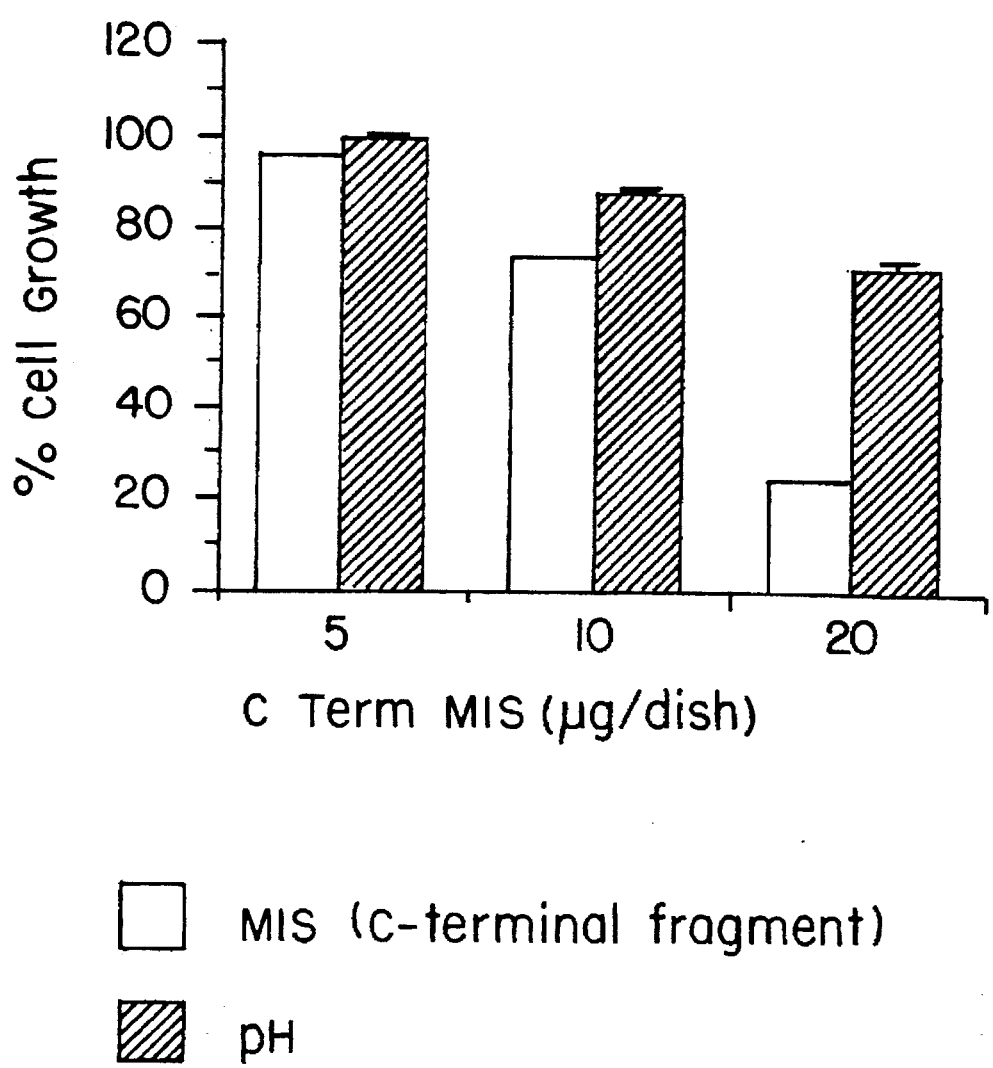

FIG. 17

```
AGCGCCGGGGCCGCGGCTGCAGACGGGCCGTGCGCTCTGCGTGAGCTGAG
-+---------+---------+---------+---------+--------
TCGCGGCCCCGGCGCCGACGTCTGCCCGGCACGCGAGACGCACTCGACTC

S  A  G  A  A  A  A  D  G  P  C  A  L  R  E  L  S

CGTAGACCTGCGGGCCGAGCGCTCGGTGCTCATCCCCGAGACATACCAGG
-+---------+---------+---------+---------+--------
GCATCTGGACGCCCGGCTCGCGAGCCACGAGTAGGGGCTCTGTATGGTCC

V  D  L  R  A  E  R  S  V  L  I  P  E  T  Y  Q  A

CCAACAACTGCCAGGGGGCCTGCGGCTGGCCTCAGTCGGACCGCAACCCG
-+---------+---------+---------+---------+--------
GGTTGTTGACGGTCCCCCGGACGCCGACCGGAGTCAGCCTGGCGTTGGGC

N  N  C  Q  G  A  C  G  W  P  Q  S  D  R  N  P

CGCTACGGCAACCACGTGGTGCTGCTGCTAAAGATGCAGGCCCGCGGCGC
-+---------+---------+---------+---------+--------
GCGATGCCGTTGGTGCACCACGACGACGATTTCTACGTCCGGGCGCCGCG

R  Y  G  N  H  V  V  L  L  L  K  M  Q  A  R  G  A

CACCCTGGCGCGCCCGCCCTGCTGTGTGCCCACAGCCTACACCGGCAAGC
-+---------+---------+---------+---------+--------
GTGGGACCGCGCGGGCGGGACGACACACGGGTGTCGGATGTGGCCGTTCG

T  L  A  R  P  P  C  C  V  P  T  A  Y  T  G  K  L

TCCTCATCAGCCTGTCCGAGGAGCGCATCAGTGCGCACCACGTCCCAAAC
-+---------+---------+---------+---------+--------
AGGAGTAGTCGGACAGGCTCCTCGCGTAGTCACGCGTGGTGCAGGGTTTG

L  I  S  L  S  E  E  R  I  S  A  H  H  V  P  N

ATGGTGGCCACCGAATGCGGCTGCCGG
-+---------+---------+-----
TACCACCGGTGGCTTACGCCGACGGCC

```
AGCGCGGGGGCCACCGCCGCCGACGGGCCGTGCGCGCTGCGCGAGCTCAG
----+---------+---------+---------+---------+-----
TCGCGCCCCCGGTGGCGGCGGCTGCCCGGCACGCGCGACGCGCTCGAGTC
 S   A   G   A   T   A   A   D   G   P   C   A   L   R   E   L   S

CGTAGACCTCCGCGCCGAGCGCTCCGTACTCATCCCCGAGACCTACCAGG
----+---------+---------+---------+---------+------
GCATCTGGAGGCGCGGCTCGCGAGGCATGAGTAGGGGCTCTGGATGGTCC
 V   D   L   R   A   E   R   S   V   L   I   P   E   T   Y   Q   A

CCAACAATTGCCAGGGCGTGTGCGGCTGGCCTCAGTCCGACCGCAACCCG
----+---------+---------+---------+---------+-----
GGTTGTTAACGGTCCCGCACACGCCGACCGGAGTCAGGCTGGCGTTGGGC
  N   N   C   Q   G   V   C   G   W   P   Q   S   D   R   N   P

CGCTACGGCAACCACGTGGTGCTGCTGCTGAAGATGCAGGCCCGTGGGGC
----+---------+---------+---------+---------+-----
GCGATGCCGTTGGTGCACCACGACGACGACTTCTACGTCCGGGCACCCCG
  R   Y   G   N   H   V   V   L   L   L   K   M   Q   A   R   G   A

CGCCCTGGCGCGCCCACCCTGCTGCGTGCCCACCGCCTACGCGGGCAAGC
----+---------+---------+---------+---------+-----
GCGGGACCGCGCGGGTGGGACGACGCACGGGTGGCGGATGCGCCCGTTCG
  A   L   A   R   P   P   C   C   V   P   T   A   Y   A   G   K   L

TGCTCATCAGCCTGTCGGAGGAACGCATCAGCGCGCACCACGTGCCCAAC
----+---------+---------+---------+---------+-----
ACGAGTAGTCGGACAGCCTCCTTGCGTAGTCGCGCGTGGTGCACGGGTTG
  L   I   S   L   S   E   E   R   I   S   A   H   H   V   P   N

ATGGTGGCCACCGAGTGTGGCTGCCGG
----+---------+---------+--
TACCACCGGTGGCTCACACCGACGGCC
  M   V   A   T   E   C   G   C   R
```

+MIS        —MIS

TESTIS 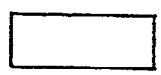 KIDNEY
FIG. 27A
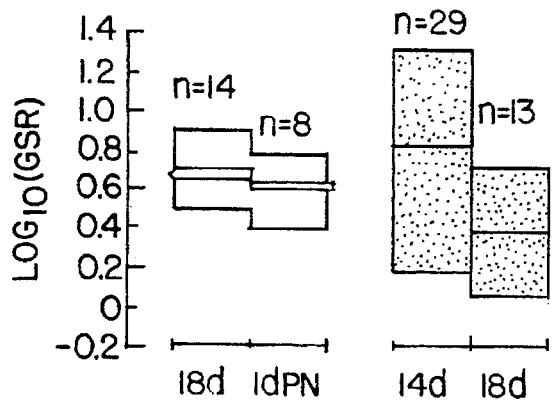
FIG. 27B
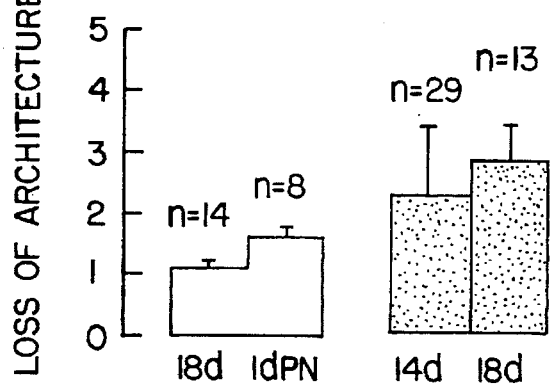
FIG. 27C
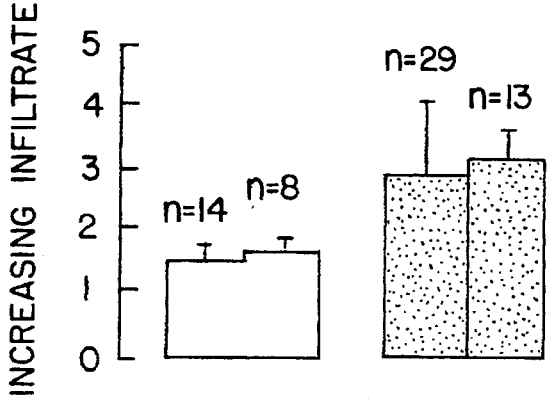

USE OF MULLERIAN INHIBITING SUBSTANCE FOR TREATING CERTAIN TUMORS AND FOR MODULATING CLASS I MAJOR HISTOCOMPATIBILITY ANTIGEN EXPRESSION

This application is a continuation of application Ser. No. 08/007,125, filed Jan. 21, 1993, now abandoned, which is a continuation-in-part of U.S. application No. 07/299,158, filed Jan. 19, 1989, now abandoned, which disclosure is herein incorporated by reference. The U.S. patent application Ser. No. 08/007,125 is also a continuation-in-part of U.S. application Ser. No. 07/901,637, filed Jun. 19, 1992, now abandoned, which is a continuation-in-part of U.S. application Ser. No. 07/683,966, filed Apr. 12, 1991, now abandoned, which disclosures are herein incorporated by reference.

This invention was made with government support under CA17393 awarded by the National Cancer Institute of the National Institutes of Health. The government has certain rights in the invention.

FIELD OF THE INVENTION

This application is directed to inhibiting local and metastatic tumor growth by administering to certain tumors an effective amount of Müllerian Inhibiting Substance or an effective amount of the carboxy-terminal fragment of MIS. This application further concerns inhibiting primary and metastatic tumor growth by transfecting tumor cells with a vector capable of expressing an effective amount of Müllerian Inhibiting Substance or an effective amount of the carboxy-terminal fragment of MIS. Also, this application is directed to DNA sequences encoding the C-terminal fragment of MIS, vectors containing the DNA sequences and transformed host cells capable of producing the C-terminal fragment. This application further concerns gene therapy treatments for patients suffering from certain tumors. Also disclosed is a method for modulating class I histocompatibility antigens by administering Müllerian Inhibiting Substance and Epidermal Growth Factor.

BACKGROUND OF THE INVENTION

Müllerian Inhibiting Substance (MIS) is produced by the fetal testis as a 140 kDa glycosylated disulfide-linked homodimer that causes regression of the Müllerian duct in the male fetus. Under reducing conditions, the protein migrates on gel electrophoresis at an apparent molecular weight of 70 kDa. The protein can be proteolytically cleaved by exogenous plasmin into two distinct fragments that migrate electrophoretically as 57 kDa and 12.5 kDa moieties with cleavage at residue 427 of the intact 535 amino acid monomer (Pepinsky, et al., *J. Biol. Chem.* 263:18961–4 (1988)).

Various methods for purifying MIS are known. U.S. Pat. No. 4,404,188, filed Jul. 29, 1981 and entitled "Purified Müllerian Inhibiting Substance and Method of Purification" describes a process for purifying MIS which comprises treatment with a protein inhibitor, chromatography on ion exchange, chromatography on wheat germ lectin, on concanavalin A and/or on a supported triazinyl dye. U.S. Pat. No. 4,487,833, filed on Mar. 1, 1982 and entitled "Method of Preparing Hybridomas and of Purifying Immunogenic Materials" describes a process for separating MIS using immunoaffinity chromatography. U.S. Pat. No. 5,011,687, filed Oct. 19, 1985 entitled "Purified Müllerian Inhibiting Substance and Process for Treating Human Ovarian Cancer Cells," describes a process for purifying MIS from testes by using aqueous polar dissociative solutions, separation of DNA and RNA, fractionation by gel filtration chromatographic elution, and isolation of the MIS. MIS may also be obtained from recombinant DNA techniques (Cate et al., *Cell* 45:685–698 (1986); Cate et al., U.S. Pat. No. 5,047,336).

In the female fetus, the Müllerian duct develops into the Fallopian tubes, uterus and upper vagina. It is known that MIS causes regression of the Müllerian duct in the male fetus. MIS has also been shown to play a role in inhibition of oocyte meiosis (Takahashi et al., *Mol. Cell. Endocrinol.* 47:225–234 (1986)), testicular descent (Hudson et al., *Endocr. Rev.* 7:270–283 (1986)), inhibition of fetal lung development (Catlin et al., *Am. J. Obstet. Gynecol.* 159:1299–1303 (1988)), inhibition of autophosphorylation of the EGF receptor (Coughlin et al., *Mol. Cell. Endocrinol.* 49:75–86 (1987); Cigarroa et al., *Growth Factors* 1:179–191 (1989)) and inhibition of tumor growth (Donahoe et al., *Science* 205:913–915 (1979); Donahoe et al., *Ann. Surg.* 194:472–480 (1981); Fuller, Jr., et al., *J. Clin. Endocrinol. Metab.* 54:1051–1055 (1982); Fuller, Jr. et al., *Gynecol. Oncol.* 22:135–148 (1985); U.S. Pat. No. 4,404,188, Donahoe, P. K., et al., filed Jul. 29, 1981).

The antitumor effect of MIS demonstrated in U.S. Pat. No. 5,011,687, was elicited using natural MIS extracted and partially purified from bovine testes. Since that time, the bovine, human, and mouse MIS genes have been cloned and the human protein expressed in Chinese hamster ovary (CHO) cells. Initial antiproliferative studies against established cell lines involved using a highly purified recombinant human MIS (rhMiS), but these studies suggested that the antiproliferative effect of rhMIS on human gynecological tumor cells is limited to ovarian cancers. (Wallen et al., *Cancer Res.* 49:2005–2011 (1986)). Furthermore, tumor response to the highly purified rhMIS was inconsistent and preparation dependent (Wallen et al., *Cancer Res.* 49:2005–2011 (1986)).

As stated, digestion of MIS with plasmin cleaves at a site 109 amino acids from the carboxy-terminus producing a 25-kDa fragment and a high molecular mass complex derived from the amino terminus of the protein. However, the N- and C-terminal fragments remain associated as a non-covalent complex. In Pepinsky et al., *Journal Biol. Chem.* 263:18961–18964 (1988), proteolysis of MIS with plasmin into N- and C-terminal fragments did not alter MIS activity in the organ culture assay measuring the ability of MIS to promote regression of the Müllerian duct. However, attempts to dissociate the non-covalent complex by acidifying the sample with acetic acid or after boiling, destroyed MIS activity in the organ culture assay. In contrast, when the two fragments were dissociated with 1% sodium deoxycholate, MIS activity in the organ culture assay was not altered. However, Pepinsky et al. were unable to determine whether both fragments were necessary for biological activity.

A later review article on MIS, Cate et al., *Müllerian-Inhibiting Substance*, in "Handbook of Experimental Pharmacology" 95/11:179–210 (1990), suggests that both the N- and C-terminal domains are necessary for regression of the Müllerian duct. The authors found that the N- and C-terminal fragment dimers were inactive when assayed individually in the organ culture assay. However, when incubated together, regression of the Müllerian duct was observed.

Recently, gene therapy has become a viable method for treating tumors. Tumor-infiltrating-lymphocytes (TILs)

have been shown efficacious in the treatment of metastatic tumors in mice and man when administered with inserted genes encoding chemotherapeutic agents. Exogenous genes can be inserted into TILs in vitro and then reinjected into a patient (Rosenberg et al., *Science* 233:1318–21 (1986); Spiess et al., *J Natl Cancer Inst* 79:1067–75 (1987); Cameron et al., *J Exp Med* 171:249–63 (1990); Rosenberg et al., *N. Engl. J. Med.* 319:1676–80 (1988); Alexander et al., *J of Immunotherapy* 10:389–97 (1991); Culver et al., *PNAS U.S.A.* 88:3155–3159 (1991); Blaese et al., *Clin. Res.* 37(2):599A (1989); Kasid et al., *PNAS U.S.A.* 87:473–77 (1990)). Direct in situ introduction of exogenous genes into proliferating tumors has also been described (Culver et al., *Science* 256:1550–2 (1992); Ram et al., *Can. Res.* 53:83–88 (1991)).

The major histocompatibility complex is a group of closely linked genes which encode molecules that restrict the specificity of antigen recognition by T lymphocytes. The antigens fall into two classes: class I and class II. The immunological aspects of the present invention are reviewed, for example, by Klein, J., *In: Immunology: The Science of Self-Non-Self Discrimination*, Wiley-Interscience, NY, pp. 270–309 (1982) and Feldman, M. et al., *Scientific American* 259:60–85 (1988), which references are herein incorporated by reference. Antigens of class I restrict antigen recognition predominantly by cytotoxic T lymphocytes, whereas antigens of class II restrict recognition by regulatory T cells. Class I MHC molecules are expressed on all cells. In contrast, MHC class II molecules are expressed predominantly, on B lymphocytes.

Agents capable of modulating the expression of the MHC class I antigens may be employed in the treatment or prevention of metastatic cancer, immunodeficiency diseases, and organ and tissue rejection.

SUMMARY OF THE INVENTION

In view of the previously reported inhibition of tumor growth caused by bovine MIS, the present inventors speculated that a highly purified form of MIS might be effective in treating tumors of generally similar origin. Although a relatively highly purified form of MIS had been previously achieved, little success was demonstrated with respect to tumor treatment. Accordingly, it was desirable to further develop a form of MIS which would be effective in inhibiting tumor growth.

This goal has been achieved by the present invention which provides for a method of inhibiting tumor growth comprising administering an effective amount of Müllerian Inhibiting Substance to a patient, said tumor selected from the group consisting of vulvar epidermoid carcinoma, cervical carcinoma, endometrial adenocarcinoma, ovarian adenocareinoma, and ocular melanoma.

Moreover, the present inventors have discovered that the Müllerian duct regression and anti-proliferative bioactivities of MIS reside in its carboxy-terminal domain. Thus, the present invention is also directed to a method of inhibiting tumor growth comprising administering an effective amount of the carboxy-terminus of MIS to a patient, said tumor selected from the group consisting of vulvar epidermoid carcinoma, cervical carcinoma, endometrial adenocarcinoma, ovarian adenocarcinoma and ocular melanoma.

The present inventors have further discovered that metastatic tumor growth can be inhibited by administering to tumor cells an effective amount of MIS or an effective amount of the C-terminal fragment of MIS.

Primary and metastatic growth of other tumors are also inhibited by administering to tumor cells an effective amount of Müllerian Inhibiting Substance or an effective amount of the C-terminal fragment of MIS. For example, in addition to the tumors recited above, prostate, lymphoid, breast, cutaneous and germ cell tumors can also be treated by methods and compositions disclosed in the present application.

The present invention is further directed to a biologically active pharmaceutical composition, i.e., a composition having Müllerian duct regression and anti-proliferative activities, containing a pharmaceutically acceptable carrier and the C-terminal fragment of MIS substantially free of the N-terminal fragment.

The present invention is further directed to DNA sequences encoding the C-terminal fragment of MIS, vectors containing the DNA sequences and transformed host cells capable of producing the C-terminal fragment.

The present invention is further directed to localized tumor treatments comprising activating MIS by cleaving MIS into C- and N-terminal fragments at the tumor site with a proteolytic enzyme.

Another goal of this invention is to reduce the concentration of chemotherapeutic agents which are currently used in the treatment of the tumors of this invention. This goal has been achieved by providing for a method of inhibiting tumor growth comprising administering an effective amount of a combination of a chemotherapeutic agent and Müllerian Inhibiting Substance or an effective amount of a combination of a chemotherapeutic agent and the carboxy-terminal fragment of MIS to a patient, said tumor selected from the group consisting of vulvar epidermoid carcinoma, cervical carcinoma, endometrial adenocarcinoma, ovarian adenocarcinoma, and ocular melanoma.

This invention further provides for a pharmaceutical composition comprising an effective tumor inhibiting amount of proteolytically cleaved Müllerian Inhibiting Substance, said tumor selected from the group consisting of vulvar epidermoid carcinoma, cervical carcinoma, endometrial adenocarcinoma, ovarian adenocarcinoma, and ocular melanoma, and a pharmaceutically acceptable carrier.

The present invention also provides DNA sequences coding for the C-terminal fragment of MIS, recombinant DNA molecules comprising such sequences, hosts comprising such sequences and processes for producing the C-terminal fragment in hosts transformed with those DNA sequences.

The present invention is further directed to inhibiting tumor growth comprising transfecting one or more tumor cells with a gene capable of expressing an effective amount of MIS. Moreover, tumor growth can also be inhibited by transletting one or more tumor cells with a gene capable of expressing an effective amount of the C-terminal fragment of MIS.

The present invention further provides a method for inhibiting metastatic tumor growth comprising transfecting one or more tumor cells with a gene capable of expressing an effective amount of MIS. Moreover, metastatic tumor growth can also be inhibited by transfecting one or more tumor cells with a gene capable of expressing an effective amount of the C-terminal fragment of MIS.

The present invention also provides gene therapy methods for treating patients with certain tumors. TILs are generated from tumor suspensions cultured in interleukin-2 (IL-2). Cultures of IL-2-stimulated TILs can be transduced in vitro with a gene capable of expressing an effective amount of MIS or an effective amount of the C-terminal fragment of MIS using an appropriate vector. When re-introduced into a patient, the gene-modified autologous TILs will infiltrate into tumors present in the patient. Therefore, the present invention is further directed to a method comprising using TILs as cellular vehicles for in vivo delivery of a gene capable of expressing an effective amount of MIS or an effective amount of the C-terminal fragment of MIS to tumors in a patient.

The present invention is also directed to other gene therapy methods for achieving in vivo delivery of a gene capable of expressing an effective amount of MIS or an effective amount of the C-terminal fragment of MIS to tumors in a patient. For example, by the method of the present invention, direct in situ introduction of a gene capable of expressing an effective amount of MIS or an effective amount of the C-terminal fragment of MIS into proliferating tumors can be achieved using retroviral vectors.

The present invention further provides methods for modulating MHC class I antigens on cell surfaces using MIS and EGF.

The MHC Class I antigens appear on the cell surface of all adult cells (Flavell et al., Science 233:437 (1986)). Their orderly yet assynchronous emergence in various embryonic organs and tissues appears to be constrained by growth factors like EGF and augmented by growth inhibitors like MIS. Thus MHC, by responding to growth modulators may act as a chemostat to serve a more basal function during fetal development, in orchestrating the divergent and uneven growth patterns so characteristic of that period.

Prolonged survival was enjoyed by fetal and postnatal testis and midgestational renal grafts transplanted beneath the renal capsule of adult congenic mice, confirming previous findings in non-immunosuppressed outbred rats (Foglia R. P. et al., Annals of Surgery 204:402 (1986); Statter M. B. et al., J. Urol. 139:204 (1988)) The strategies that enable immature tissues to escape rejection in a graft survival assay were studied by comparing expression of major histocompatibility (MHC) Class I and Class II protein and mRNA in each tissue at different ages. In general, graft survival was best when Class I & II expression was low. After transplantation, surviving kidney and testis grafts both showed marked induction of Class I and II mRNA measured using donor and recipient specific oligonucleotide probes. Immunohistochemically detected protein of both classes, however, could not be found in the kidney and was minimal in the testis. Fetal tissues appear to express lower levels of protein and mRNA, and, although invading lymphocytes may induce expression of Class I and II mRNA after transplantation, protein was not inducible. The failure of these tissues to express significant levels of transplantation antigens provides an explanation of the prolonged survival of these immature grafts.

Monoclonal antibodies raised against semi-purified bovine Müllefian Inhibiting Substance (MIS) (Shima et al., Hybridoma 3:201–214 (1984)) were found to be specific for bovine MIS and not to cross react with high affinity for human, mouse, or rat MIS. The cloning, expression and amplification of the human MIS gene (Cate et al., Cell 45:685–698 (1986)) enabled purification of sufficient quantities (Pepinsky et al., J. Biol. Chem. 263:18961 (1988)) for immunization of mice and rabbits. Mono and polyclonal antibodies were raised to human MIS by conventional techniques. An enzyme linked immunosorbent assay (EHSA) was established with the sensitivity and specificity to measure MIS in human serum. The assay is specific for MIS and does not recognize Transforming Growth Factors (Beta) 1 or 2 (TGFB1 or 2), polypeptides within the same gene family. Luteinizing Hormone (LH) and Follicle Stimulating Hormone (FSH) did not cross react or interfere with the assay.

A wide spectrum of samples have been investigated using the ELISA. Normative MIS values in humans were established for newborn males and females and for infants, children and adults. The ELISA has been useful in monitoring recombinant vector production of MIS and subsequent purification. It has also been used to investigate MIS half-life and pharmacology in anti-proliferative tumor assays. The ELISA has been used to confirm route of administration and half life in studies of the MIS effect on surfactant production in developing lungs (Carlin et al., Amer. J. Ob. Gyn 159:1299 (1988)). Also, MIS was measured in a patient with a sex cord tumor before, during and after multiple operative procedures to excise the undispersed but slow growing tumor. The assay may be used for assessment of: babies with intersex abnormalities and other sexual congenital abnormalities, newborns with Respiratory Distress Syndrome, patients with Sertoli cell neoplasms or other tumors, and patients undergoing In Vitro Fertilization (IVF).

BRIEF DESCRIPTION OF THE DRAWINGS

The present invention will be better understood by reference to the Description of the Preferred Embodiments when taken together with the attached drawings, wherein:

FIG. 16. The effect of daily addition of rhMIS carboxy-terminus and vehicle control buffer in volumes corresponding to the rhMIS carboxy-terminal domain additions of 5, 10, or 20 μg. The rhMIS carboxy-terminus significantly inhibits cell proliferation at 20 μg, and a small dose-dependent buffer effect is noted.

FIG. 17 shows the amino acid (SEQ ID NO:2) and nucleotide (SEQ ID NO:1) sequences of bovine MIS, C-terminal fragment, having about 109 amino acids.

FIG. 18 shows the amino acid (SEQ ID NO:4) and nucleotide (SEQ ID NO:3) sequences of human MIS, C-terminal fragment, having about 109 amino acids.

FIG. 27 shows a comparison of graft size ratio, and histology (architecture and lymphocytic infiltrate) between 14 and 18-day fetal kidney allografts after implantation for 7 days, and between 18-day fetal and 1-day postnatal testis allografts implanted for 10 days. All values represented in (A) are log10 transformed graft size ratios (L×W in final/ L×W in initial), as a measure of individual graft growth, illustrated as range (boxes) and mean (bars). Histologic changes, as demonstrated by loss of architecture (B), and increasing lymphocytic infiltrate (C), were graded using a scale where 1 is best and 5 is worst (Statter M. B. et al., *J. Urol.* 139:204 (1988)). (A) Fourteen-day fetal kidney grafts (gray box) (n=29) show a 6.8±3.9 fold increase (0.8 log10) in size, whereas 18-day fetal grafts (n=13) implanted for the same seven days show only a 2.2±1.3 fold increase (0.3 log10) in size (p<0.008). Eighteen-day fetal (n=14) and 1-day postnatal (n=8) testis grafts (black box) attain a comparable size (5.06±1.69 and 4.21±1.06), (0.6 log10) after 10 days of implantation. Histologically, (B), the 14-day fetal kidney grafts show mild to moderate deterioration in architecture (2.19±1.05) and a (C), moderate lymphocytic infiltrate (2.90±1.12); the 18-day fetal grafts show slightly greater deterioration in architecture (2.8±0.56) and a slightly greater lymphocytic infiltrate (2.99±0.42). In contrast, the testes at both 18 days of gestation and 1 day postnatally, (B), maintain their architecture (1.07±0.18 and 1.63±0.17 respectively) and, (C), show only a slight lymphocytic infiltrate (1.45±0.31 and 1.63±0.17 respectively). The combination in the testis of growth of older implants and minimal histologic signs of rejection indicate better functional graft survival of the testis as compared to the kidney.

DESCRIPTION OF THE PREFERRED EMBODIMENTS

Figure 1:
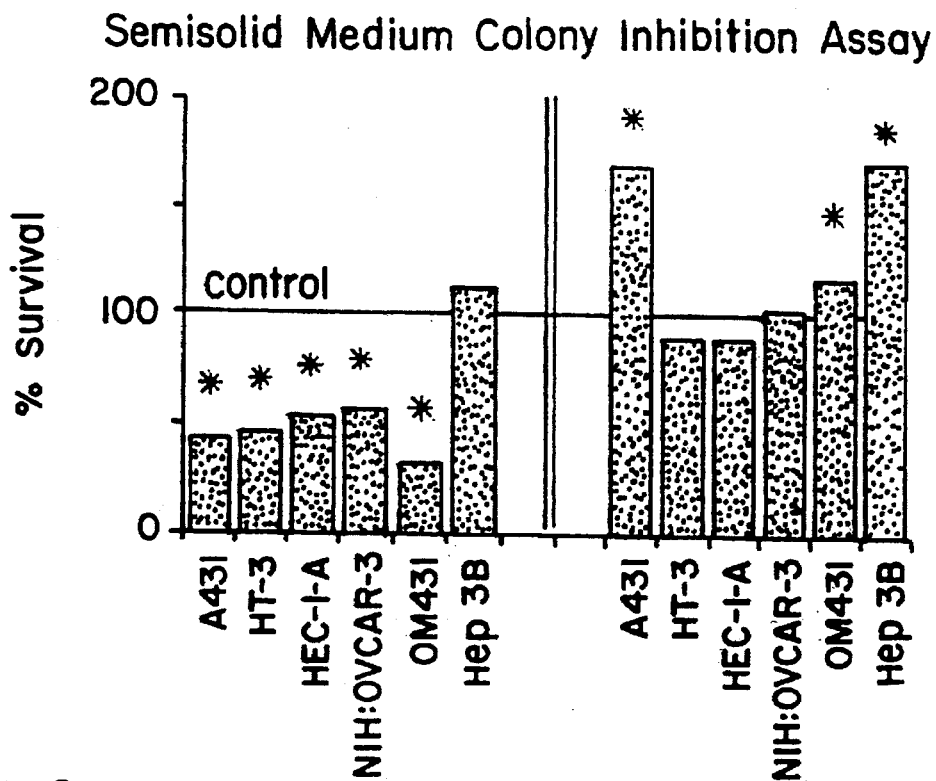
FIG. 1 shows the results of a semisolid medium (double layer) colony inhibition assay. The left side of the figure shows the effects of the immunoaffinity chromatography method described herein (IAP-MIS) in which colony formation of A431, HT-3, HEC-1-A, NIH:OVCAR-3, and OM431 cells was significantly inhibited (30 nM). The right side of FIG. 1 shows the effect of the salt fraction pre-eluted from the immunoaffinity column (IAP-salt). Stimulation of A431, OM431 and Hep 3B colony formation was seen when treated with the salt eluted fraction. The symbol "*" indicates p<0.05 when compared with control.

The term "Müllerian Inhibiting Substance" (interchangeably referred to as "MIS") is intended to include compounds and materials which are structurally similar to MIS. Examples of such included substances and materials are salts, derivatives, and aglycone forms of MIS. Additionally, the present invention is intended to include mutant forms of MIS which have substantially the same biological activity as MIS. Examples of such mutant forms would be MIS molecules carrying a deletion, insertion, or alteration in amino acid sequence. MIS may be obtained from any mammalian source or, as indicated above, from non-mammalian sources through the use of recombinant DNA technology, or from the chemical synthesis of the MIS protein.

The present inventors have found that MIS is a particularly effective anti-cancer agent due to its anti-proliferative effects on various tumors. In addition, application of MIS to patients has no known unfavorable side effects.

The term "carboxy-terminal (C-terminal) fragment of MIS" is intended to include compounds and materials structurally similar to the about 12.5 kDa (about 25 kDa under non-reducing conditions) C-terminal fragment of MIS resulting from proteolytic (e.g., plasmin) cleavage at residue 427 of the intact 535 amino acid human MIS monomer. The proteolytic (e.g., plasmin) cleavage site is at residue 443 of the 551 amino acid bovine MIS molecule. In particular, "carboxy-terminal (C-terminal) fragment of MIS" is intended to include the about 25 kDa homodimeric C-terminal fragment of MIS. The present inventors have discovered that Müllerian duct regression and antiproliferative activities reside in the C-terminal domain of MIS.

By "N-terminal fragment of MIS" is intended the about 57 kDa fragment resulting from the above-noted cleavage at residue 427 of the intact 535 amino acid human MIS monomer (residue 443 of the 551 amino acid bovine MIS). More prolonged proteolytic exposure results in further proteolysis of the N-terminal fragment of MIS yielding 34- and 22 kDa fragments of the amino-terminal moiety.

The C-terminal amino acid and nucleotide sequences for bovine MIS are shown in FIG. 17. The C-terminal amino acid and nucleotide sequences for human MIS are shown in FIG. 18. A comparison of the amino acid sequence for human and bovine MIS, showing the N- and C-terminal domains is shown in Cate et al., *Handbook of Experimental Pharmacology* 95/II: 184, edited by M. B. Spoon and A. B. Roberts, Spinger-Verlag Berlin Heidelberg (1990). The contents of FIG. 3 of this reference are herein incorporated by reference. The human sequence is shorter in that it misses certain sequences at the N-terminal domain, relative to bovine.

Additionally, the present invention is intended to include mutant forms of the C-terminal fragment of MIS which have substantially the same biological activity as the C-terminal fragment of MIS.

Examples of such mutant forms would be C-terminal fragment of MIS molecules carrying a deletion, insertion, or alteration of amino acid sequence.

In particular, the C-terminal fragment of MIS can be modified to increase its half-life in vivo. For example, addition of one or more amino acids or other chemical agents to the amino and/or carboxyl end of the C-terminal fragment can be used to increase the fragment's stability.

The C-terminal fragment of MIS can be obtained from a mammalian source or through the use of recombinant DNA technology, or from chemical synthesis of the C-terminal polypeptide.

As shown in Example 2, the about 25 kDa homodimeric C-terminal fragment of MIS can be generated by proteolytic cleavage of holo rMIS produced from Chinese hamster ovary cells.

A gene is said to be a "recombinant" gene if it results from the application of Recombinant DNA Techniques. Examples of recombinant DNA techniques include cloning, mutagenesis, transformation, etc. Recombinant DNA Techniques are disclosed in Maniatis et al., *Molecular Cloning: A Laboratory Manual*, Cold Spring Harbor, N.Y. (1982).

The term "patient" is intended to include animal patients. More preferably, "patient" is intended to include mammalian patients, most preferably, human patients.

Using any of the known methods for purifying MIS, a pharmaceutical preparation for treating the tumors of this invention can be prepared. In order to achieve a highly purified MIS which is substantially free from proteolytic enzymes or inhibition of MIS antiproliferative activity, the use of the method described in U.S. patent application No. 07/683,957, filed on Apr. 12, 1991, and which is fully incorporated by reference, is preferred. This preferred method takes advantage of the specificity of antigen-antibody interactions to recover a product having a substantially pure MIS product. Specifically, this method incorporates the use of immunoaffinity chromatography, but improves upon previously used methods in that the recovered MIS product is substantially free of contaminating enzymes having MIS proteolytic activity or inhibitors of MIS antiproliferative activity.

The immunoaffinity chromatography method used herein effectively eliminates contaminating enzymes having MIS proteolytic activity or inhibitors of MIS anti-proliferation activity from an immunoaffinity chromatography matrix by eluting with an effective amount of an alkali metal halide or an alkaline earth metal halide. The MIS is then recovered by eluting with an acid solution having a pH of between about 2.5 and 4.0. This end product is referred to herein as IAP-MIS.

The IAP-MIS can be obtained in solution at up to 95% purity. While the percent purity is comparable to other immunoaffinity purifications processes, the IAP-MIS is substantially free of contaminating proteolytic enzymes or inhibitors of MIS antiproliferative activity.

The purified MIS of this invention can be obtained in solution at up to 95% purity or greater. While the percent purity is comparable to other immunoaffinity purification processes, the MIS composition of this invention is substantially free of contaminating proteolytic enzymes or inhibitors of MIS antiproliferative activity.

For purposes of this invention, purified MIS is considered to be a MIS composition which is substantially free of contaminating proteolytic enzymes or inhibitors of MIS antiproliferative activity regardless of percent purity. The composition is considered to be substantially free of proteolytic enzymes if gel electrophoresis of the purified MIS product indicates a protein having a molecular weight of 140 kDa or 70 kDa. Gel electrophoresis of such a product will not show time dependent proteolytic fragments which are degradation products of MIS. For example the 57 kDa, 12.5 kDa, 34 kDa and 22 kDa degradation fragments of MIS further described herein will not be readily discernable by standard gel electrophoresis methods in substantially pure holo MIS.

The MIS composition will be considered to be substantially free of inhibitors of MIS antiproliferative activity if the MIS blocks proliferation of tumor cells. Examples of such tumor cells are included herein and in U.S. patent application No. 07/683,957. These examples include tumors selected from the group consisting of vulvar epidermoid carcinoma, endometrial adenocarcinoma, cervical carcinoma, endometrial adenocareinoma, ovarian adenocarcinoma, and other ocular melanoma. The determination of antiproliferative activity of these cells can be achieved by any of the procedures described herein and in U.S. patent application No. 07/683,957.

In order to obtain MIS which is substantially free of proteolytic enzymes or inhibitors of MIS antiproliferative activity, the contaminants are separated from the MIS using immunoaffinity chromatography. Separation occurs by eluting the enzymes or inhibitors with an alkali metal halide or an alkaline earth metal halide. Such a compound will generally be in solution and an effective amount of halide will be between about 0.1M and 2.0M. As alkali metals, the ions of lithium, sodium and potassium are preferred with sodium being the most preferable. As alkaline earth metals, the ions of magnesium and calcium are preferred. As halides, the ions of fluorine, chlorine, bromine and iodine are preferred with chlorine being most preferable. When eluting with sodium chloride, a solution of between about 0.1 and 2.0M is preferred. The concentration of halide can also be varied as elution progresses if desired. This can be accomplished by increasing molar concentration of halide in a stepwise fashion. It is preferred that each step be altered after about 0.1–2.0 bed volumes of solution have contacted the chromatography matrix, although such steps can be further modified as desired.

The halide can also be accompanied in solution with an effective amount of a chelating agent. These agents are capable of binding metal ions which can inactivate enzymes that require the metal ions for activity. Such agents include the compounds ethylenediamine tetraacetate (EDTA), and ethylenebis(oxyethylenenitrilo)tetraacetic acid (EGTA). Chelants can be effectively added in a range of between 0.1 and 50 mM.

After the contaminating proteolytic enzymes or inhibitors of MIS antiproliferative activity have been separated, the MIS can be recovered by eluting with an acid solution having a pH of between about 2.0 and 4.0. Although dilutions of strong acids such as HCl can be used, organic acids are preferred because of their relatively mild acid strength. For example, the use of acid amines and imines can be employed as well as monocarboxylic, dicarboxylic and tricarboxylic acids. Preferred as monocarboxylic acids are acetic, propionic and butyric acid. Preferred as dicarboxylic acids are succinic, fumaric and malic acid. Preferred as a tricarboxylic acid is citric acid. Preferred among the amines are the acidic amino acids such as aspartic and glutamic acid. The pH of the acid solution can also be incrementally varied as in the application of the halide.

After the purified MIS product has been eluted, it is preferable to neutralize the product to a pH of between 6.8 and 7.6 to guard against acid hydrolysis. This can be accomplished by various hydroxide compounds such as NaOH or $NH_4OH$ or by various buffers which can quickly achieve neutralization of the product in the desired pH range. These hydroxide compounds are not to be considered as all inclusive as those of ordinary skill in the art will appreciate.

Although this specification describes a pharmaceutical composition which comprises proteolytically cleaved Müllerian Inhibiting Substance, it is to be understood that the MIS 140 kDa homodimer or the 70 kDa subunit of MIS can be included in the pharmaceutical composition. In this case, naturally occurring proteolytic enzymes in vivo can proteolytically cleave MIS to its effective form. Such enzymes are represented by the proteolytic compounds described herein.

The term "protein fragment" is meant to include both synthetic and naturally-occurring amino acid sequences derivable from the naturally occurring amino acid sequence of MIS. The protein is said to be "derivable from the naturally-occurring amino acid sequence of MIS" if it can be obtained by fragmenting the naturally-occurring chosen sequence of MIS, or if it can be synthesized based upon a knowledge of the sequence of the naturally occurring amino acid sequence or of the genetic material (DNA or RNA) which encodes this sequence.

The term "proteolytically cleaved" refers to an MIS product obtained by treatment with any substance which is capable of cleaving either the homodimer or the 70 kDa subunit of MIS into a protein fragment which inhibits growth of the tumors of this invention. In general, MIS is effective in treating the tumors of this invention when proteolytically cleaved to form protein fragments of about 57 kDa and 12.5 kDa. Such substances which cleave MIS in this manner include serine proteases, such as plasmin, and endopeptidases. These enzymes are not to be considered as all inclusive or limiting in any manner since other enzymes can also proteolytically cleave MIS and such enzymes can be readily determined by those of ordinary skill in the art.

The about 12.5 kDa (about 25 kDa under non-reducing conditions) C-terminal fragment of MIS can be purified from proteolytically cleaved MIS thereby freeing the C-terminal fragment from its association with the N-terminal fragment in the N- and C-terminal non-covalent complex that forms after proteolytic treatment of intact MIS. Suitable purification techniques include column chromatography separation techniques known in the art. For example, the polyacrylamide column technique set forth in Example 3 is particularly suitable for purifying the C-terminal fragment of MIS. The C-terminal fragment of MIS can also be purified by other art-known techniques, provided that the biological activity of the C-terminal fragment is not destroyed during purification. As stated, the antiproliferative activity of MIS resides in its C-terminal domain. Thus, the C-terminal fragment of MIS alone is effective in treating the tumors of this invention. The N-terminal fragment may be present during tumor treatment, but it is not required for inhibition of tumor growth. Cleavage of MIS into N- and C-terminal fragments can occur by exogenous proteolysis or by proteolysis in vivo.

Another embodiment of the present invention is directed to using MIS in a method for treating the tumors of the present invention in a site-specific manner. As indicated above, MIS is activated to have antiproliferative and Müllerian duct regression activities upon proteolytic cleavage. Thus, MIS can be used as an antiproliferative agent in a site-specific method for treating the tumors of the present invention. The method comprises activating MIS which has been administered to a patient by cleaving the MIS molecule into fragments of about 57 kDa and about 12.5 kDa (about 25 kDa as a homodimer) upon contact with a cleaving substance (e.g., plasmin) located at or provided to the tumor site. As stated above, substances which cleave MIS in this manner include serine proteases, such as plasmin, and endopeptidases. The cleaving substance can be delivered to the tumor site by perfusion. Methods for perfusing tumors with substances such as plasmin are evident to one having ordinary skill in the art. After perfusing the tumor with a cleaving substance, MIS can be administered to a patient by one or more of the variety of techniques either disclosed herein or known in the art. Post-administration, MIS will remain inactive until activated by cleavage. Since the exogenous cleaving substances are localized at the tumor site, MIS is activated in a site-specific manner at the tumor site. Such a localized tumor treatment can advantageously limit possible toxicity that can be caused by systemic administration of MIS in its activated form.

When MIS is administered to a patient in inactive form, without the use of exogenous cleaving substances, endogenous cleaving substances are relied upon to cleave MIS into its activated form.

The invention further pertains to polypeptides that, in addition to the chosen sequence, may contain or lack one or more amino acids that may not be present in the naturally-occurring sequence, wherein such polypeptides are functionally similar to or possess antagonist activity to the chosen polypeptide. Such polypeptides for the present invention, are termed "functional derivatives," provided that they demonstrate activity which is substantially similar to or antagonistic to that of MIS or the C-terminal fragment of MIS.

Included within the scope of this invention are the use of additional amino acid residues added to enhance coupling to carrier protein or amino acid residues added to enhance the tumorigenic treatment of this invention. The MIS composition or the composition containing the C-terminal fragment of MIS may be in the form of the free amines (on the N-terminus), or acid-addition salts thereof. Common acid solution salts are hydrohalic acid salts, i.e., HBr, HI, or more preferably, HCl. Useful cations are alkali or alkaline earth metallic cations (i.e., Na, K, Li, ½Ca, ½Ba, etc.) or amine cations (i.e., tetraalkylammonium, trialkylammonium, where alkyl can be $C_1$–$C_{12}$). As known in the art, the amino acid residues of MIS or its C-terminal fragment may be in their protected or unprotected form, using appropriate amino or carboxyl protecting groups.

The C-terminal fragment (human or bovine) can be readily produced by the recombinant DNA techniques described in U.S. Pat. No. 5,047,336, which is fully incorporated by reference herein. Of particular interest is expression of the C-terminal fragment in E. coli and other bacteria, since the C-terminal fragment is not glycosylated.

The pharmaceutical compositions of this invention can be formulated according to known methods to prepare pharmaceutically useful compositions, whereby MIS or the C-terminal fragment of MIS or their functional derivatives are combined in admixture with a pharmaceutically acceptable carrier vehicle. Suitable vehicles and their formulation, inclusive of other human proteins, i.e., human serum albumin, are described for example in Remington's Pharmaceutical Sciences (16th Ed., A. Oslo, Ed., Mack, Easton, Pa. (1980)). In order to from a pharmaceutically acceptable composition suitable for effective administration, such compositions will contain an effective amount of MIS or the C-terminal fragment of MIS, or their functional derivatives, together with a suitable amount of carrier vehicle.

The present inventors have further discovered that, in addition to primary tumor growth, metastatic tumor growth is also inhibited when exposed to MIS or the C-terminal fragment of MIS.

Therefore, the present invention is further directed to inhibiting primary and metaastatic tumor growth by administering to tumor cells an effective amount of MIS or an effective amount of the C-terminal fragment of MIS.

The present invention is further directed to a method for inhibiting primary growth of tumors by transfecting tumor cells with a gene capable of expressing an effective amount of MIS or an effective amount of the C-terminal fragment of MIS. A further embodiment of the present invention is directed to a method for inhibiting metastatic tumor growth comprising transfecting tumor cells with a gene capable of expressing an effective amount of MIS or an effective amount of the C-terminal fragment of MIS.

Primary and metastatic growth of the following tumors can be inhibited by the above-described methods: vulvar epidermoid carcinomas, cervical carcinomas, endometrial adenocarcinomas, ovarian adenocarcinomas and ocular melanomas. Further, primary and metastatic growth of prostate, lymphoid, breast, cutaneous and germ cell tumors can also be inhibited by the methods of the present invention.

Primary tumor growth and metastases entail different molecular mechanisms. Primary tumor growth involves local proliferation of tumor cells. However, for a tumor cell to become metastatic, a complex multi-step process must occur—i.e., detachment of tumor cells from the local growth, invasion of inter-cellular matrices, penetration of basement membranes of blood vessels, circulation while undergoing homotypic aggregation, extravasation, and induction of angiogenesis in the target organ. Each of these successive steps appears to be mediated by defined molecular mechanisms of the metastatic cell. Therefore, a tumor cell, while exhibiting local tumor growth, may fail to generate metastases if it lacks the molecular machinery required for any one of the sequential metastatic steps. The differences between local (primary) and metastatic-tumor growth are discussed in Eisenbach et al., Cancer Rev. 5:1–18 (1986).

The complete nucleotide and amino acid sequence for human and bovine MIS is provided in Cate et al., U.S. Pat. No. 5,047,336, which disclosure is herein incorporated by reference. As stated, the bovine and human amino acid and nucleotide sequences of the C-terminal fragment of MIS are disclosed in FIGS. 17 and 18, respectively. Appropriate cloning or expression vehicles capable of expressing an effective amount of MIS or an effective amount of the C-terminal fragment of MIS in tumors cells will be known to the artisan. Suitable cloning or expression vehicles include those described herein and in U.S. Pat. No. 5,047,336 and Cate et al., Cell 45:685–698 (1986).

As shown in Example 4, transfecting tumor cells with expression vehicles capable of expressing an effective amount of MIS inhibits local (primary) and metastatic tumor growth in vitro and in vivo.

Within a specific cloning or expression vehicle, various sites may be selected for insertion of the gene coding for MIS or C-terminal fragment of MIS. These sites are usually designated by the restriction endonuclease which cuts them and are well recognized by those of skill in the art. Various methods for inserting DNA sequences into these sites to form recombinant DNA molecules are also well known. These include, for example, dG-dC or dA-dT tailing, direct ligation, synthetic linkers, exonuclease and polymerase-linked repair reactions followed by ligation, or extension of the DNA strand with DNA polymerase and an appropriate single-stranded template followed by ligation. It is, of course, to be understood that a cloning or expression vehicle useful in this invention need not have a restriction endonuclease site for insertion of the chosen DNA fragment. Instead, the vehicle could be joined to the fragment by alternative means.

Various expression control sequences may also be chosen to effect the expression of the DNA sequences of this invention. These expression control sequences include, for example, the lac system, the β-lactamase system, the trp system, the tac system, the trc system, the major operator and promoter regions of phase λ, the control regions of fd coat protein, the promoter for 3-phosphoglycerate kinase or other glycolytic enzymes, the promoters of acid phosphatase, e.g., Pho5, the promoters of the yeast α-mating factors, promoters for mammalian cells such as the SV40 early promoter, adenovirus late promoter and metallothionine promoter, and other sequences known to control the expression of genes of prokaryotic or eukaryotic cells or their viruses and various combinations thereof. In mammalian cells, it is additionally possible to amplify the expression units by linking the gene to that for dihydrofolate reductase and applying a selection to host Chinese hamster ovary cells.

For expression of the DNA sequences of this invention, these DNA sequences are operatively-linked to one or more of the above-described expression control sequences in the expression vector. Such operative linking, which may be effected before or after the MIS or C-terminal fragment of MIS DNA sequence is inserted into a cloning vehicle, enables the expression control sequences to control and promote the expression of the DNA sequence.

The vector or expression vehicle, and in particular the sites chosen therein for insertion of the selected DNA fragment and the expression control sequence employed in this invention, is determined by a variety of factors, e.g., number of sites susceptible to a particular restriction enzyme, size of the protein to be expressed, expression characteristics such as start and stop codons relative to the vector sequences, and other factors recognized by those of skill in the art. The choice of a vector, expression control sequence, and insertion site for the MIS or C-terminal fragment of MIS DNA sequence is determined by a balance of these factors, not all selections being equally effective for a given case.

It should also be understood that the DNA sequences coding for MIS or the C-terminal fragment of MIS that are inserted at the selected site of a cloning or expression vehicle may include nucleotides which are not part of the actual gene coding for MIS or the C-terminal fragment of MIS or may include only a fragment of the actual gene. It is only required that whatever DNA sequence is employed, a transformed host will produce MIS or the C-terminal fragment of MIS. For example, the MIS DNA sequences of this invention may be fused in the same reading frame in an expression vector of this invention to at least a portion of a DNA sequence coding for at least one eukaryotic or prokaryotic signal sequence, or combinations thereof. Such constructions enable the production of, for example, a methionyl or other peptidyl-MIS polypeptide, that is part of this invention. This N-terminal methionine or peptide may either then be cleaved intra- or extra-cellularly by a variety of known processes or the MIS polypeptide with the methionine or peptide attached may be used, uncleaved, in the pharmaceutical compositions and methods of this invention.

The cloning vehicle or expression vector containing the MIS or C-terminal fragment of MIS polypeptide coding sequences of this invention is employed in accordance with this invention to transform tumor cells so as to permit expression of an effective amount of MIS or an effective amount of the C-terminal fragment of MIS to inhibit primary or metastatic tumor growth.

As indicated, it should be understood that the MIS polypeptide (prepared in accordance with this invention) may include polypeptides in the form of fused proteins (e.g., linked to prokaryotic, eukaryotic or combination N-terminal segment to direct excretion, improve stability, improve purification or improve possible cleavage at amino acid residue 443 to release an active C-terminal fragment), in the form of a precursor of MIS (e.g., starting with all or parts of a MIS signal sequence of other eukaryotic or prokaryotic signal sequences), in the form of a mature MIS polypeptide, or in the form of an fmet-MIS polypeptide.

The present invention also encompasses substituting codons for those of the MIS or C-terminal fragment of MIS nucleotide sequences. These substituted codons may code for amino acids identical to those coded for by the codons replaced but result in higher yield of the polypeptide. Alternatively, the replacement of one or a combination of codons leading to amino acid replacement or to a longer or shorter polypeptide may alter its properties in a useful way (e.g., increase the stability, increase the solubility or increase the therapeutic activity).

The present invention also provides gene therapy methods for treating patients with certain tumors. Tumor-Infiltrating-lymphocytes (TILs) are prepared from tumor biopsies obtained from patients suffering from tumors by methods known in the art (Rosenberg et al., N. Engl. J. Med. 319:1676–80 (1988); Topalian et al., J. Immuol. 142:3714–25 (1989)). The gene coding for MIS or the C-terminal fragment of MIS can be inserted into an appropriate retroviral vector. Preferably, the retroviral vector will include a "selection" gene. That is, a gene coding for a product that allows for selection of TILs containing the retrovirus vector with insert. Suitable "selection" genes are those coding for antibiotic resistance, such as the neomycin resistance gene. Other "selection" genes are known in the art.

Preferably, the gene coding for MIS or the C-terminal fragment of MIS is inserted into the N2 retroviral vector which contains a neomycin resistance gene. The retroviral vector with MIS or C-terminal fragment insert can be transfected into an amphotropic packaging cell line. For example, the amphotropic packaging cell lines PA-12 or PA-317 can be used. Suitable retroviral vectors and amphotropic cell lines are described in Miller et al., Mol. Cell. Biol. 6:2895–29 (1986); Cornetta et al., J. Virol. Methods 23:187–94 (1989); and Anderson et al., Science 226:401–9 (1984).

The above-described TILs can be cultured in interleukin-2 (IL-2) using art-known techniques. For example, a protocol at the National Cancer Institute requires growing the TILs in plastic, gas permeable culture bags (Topalian et al., J. Immunol. Methods 102:127 (1987)). Each bag supports Up to $3 \times 10^9$ TIL in a 1.5 liter volume of tissue culture medium containing human serum albumin and IL-2. More recently, Knazek et al., J. of Immunol. Methods 127:29–37 (1990) describes an improved method for growing TILs to clinically useful quantities. The Knazek et al. method involves growing TILs in hollow fiber cartridges.

Cultures of TILs can be transduced with a recombinant retroviral vector containing the MIS or C-terminal fragment of MIS gene insert using art-known techniques. For example, transduction can occur by exposing the TILs to culture supernatant from packaging cell lines transfected with a retroviral vector containing the MIS or C-terminal fragment of MIS gene insert. Transducing cultures of TILs by exposure to culture supernatant from a packaging cell line that produces N2 containing virions is described in Culver et al., Proc. Natl. Acad. Sci. U.S.A. 88:3155–59 (1991); Kasid et al., Proc. Natl. Acad. Sci. U.S.A. 87:473–7 (1990); Miller et al., Mol. Cell. Biol. 6:2895–2902 (1986); Cornetta et al., J. Virol. Methods 23:187–94 (1989); and Anderson et al., Science 226:401–9 (1984).

Transduced-TILs can then be selected for in an appropriate selection medium. For example, if the retroviral vector contains the neomycin transferase gene, selection can occur in the neomycin analog G418. Thus, TILs containing the retroviral vector will be selected for in the medium. These TILs can then be further grown until the total growth reaches the number of cells ordinarily used for therapy. Current protocols infuse $2-3 \times 10^{11}$ cells into the patient for therapy. Infusion can occur by any suitable method. For example, the genetically-altered TILs can be re-inserted into the patient intravenously.

Genetically-altered TILs are known to preferentially localize at the tumor site in vivo. See, for example Culver a al., Proc. Natl. Acad. Sci. U.S.A. 88:3155–59 (1991) and Kasid et al., Proc. Natl. Acad. Sci. U.S.A. 87:473–7 (1990). Therefore, the present invention provides a method of treating tumors in a patient comprising using TILs as cellular vehicles for transferring a retroviral vector, capable of expressing an effective amount MIS or an effective amount of the C-terminal fragment of MIS, to the tumor site.

Another embodiment of the present invention provides a method for direct in situ introduction of a retroviral vector, capable of expressing an effective amount of MIS or an effective amount of the C-terminal fragment of MIS, into proliferating tumors. As stated, the gene coding for MIS or the C-terminal fragment of MIS can be inserted into a retroviral vector to form a recombinant construct. As indicated, this construct can be transfected into an amphotropic packaging cell line using art-known techniques. As stated, suitable retroviral vectors and amphotropic cell lines are described in Miller et al., *Mol. Cell. Biol.* 6:2895–2902 (1986); Cornetta et al., *J. Virol. Methods* 23:187–94 (1989); and Anderson et al., *Science* 226:401–9 (1984). Transfected packaging cell lines are known to continually release the retroviral vector. Thus, the transfected packaging cell line can be injected into the tumor mass for direct in situ transfer of the gene coding for MIS or the C-terminal fragment of MIS to the tumor. Alternatively, the transfected packaging cell line can be grafted near or into the tumor to provide a long-lasting source of the retrovirus containing the MIS or C-terminal fragment of MIS gene insert (see Rosenberg et al., *Science* 242:1575–78 (1988) and Wolff et al., *PNAS U.S.A.* 86:9011–9014 (1989)). In vivo gene transfer using retroviral vector-producer cells for treating tumors is described in Culver et al., *Science* 256:1550–52 (1992) and Ram et al., *Cancer Research* 53:83–88 (1991).

In addition to the gene coding for MIS or the C-terminal fragment of MIS, the above-described retroviral vectors can also contain one or more or drug susceptibility ("suicide") genes. For example, retrovirus vectors used in the methods of the present invention can further include the gene coding for herpes simplex thymidine kinase (HS-tk). Tumor cells containing the HS-tk gene become sensitive to treatment with ganciclovir (GCV) (Moolten et al., *Cancer Res.* 46:5276 (1985); Borrelli et al., *Proc. Natl. Acad. Sci U.S.A.* 85: 7572 (1988); Moolten et al., *J. Natl. Cancer Inst.* 82:297 (1990); and Ezzedine et al., *New Biol.* 3:608 (1991)). Alternatively, the retrovirus vectors of the present invention can include the gene coding for the bacterial enzyme cytosine deaminase. Tumor cells expressing the bacterial enzyme cytosine deaminase convert the ordinarily nontoxic drug 5'-fluorocytosine to the cytotoxic compound 5-fluorouracil, which will kill the tumor cells (Mullen et al., *PNAS U.S.A.* 89:33 (1992)). In addition to those described above, other drug susceptibility genes can be used. Including a drug susceptibility gene in the vector in addition to the gene coding for MIS or the C-terminal fragment of MIS can increase toxicity to the tumor cells without adversely affecting surrounding normal cells.

An "effective amount" of MIS is one which is sufficient to inhibit growth of the tumors of this invention in a human or animal. Likewise, an "effective amount" of the C-terminal fragment of MIS is one which is sufficient to inhibit growth of the tumors of this invention in a human or animal. According to this invention, inhibition of a tumor implant can be indicated by a decrease in graft size ratio. The graft size ratio is calculated as (L2×W2×W2)/(L1×W1×W1), wherein L1 is the longest diameter of the implant, W1 is the diameter perpendicular to L1, L2 is the longest diameter of the tumor, and W2 is the diameter perpendicular to L2. Using this calculation, inhibition is demonstrated when the graft size ratio of a treated specimen is less than the graft size ratio of an untreated control. When assessing inhibition of a naturally occurring tumor in a patient, the volume of the tumor (L2×W2×W2) before and after treatment need only be compared.

The effective amount may vary depending upon criteria such as the age, weight, physical condition, past medical history, and sensitivity of the recipient. The effective amount will also vary depending on whether administration is oral, intravenous, intramuscular, subcutaneous, local, or by direct application to the tumor. In the case of direct tumor application, it is preferable that a final serum concentration of at least 0.1 nM, preferably about 0.1–1.0 nM, of MIS be achieved. Likewise, for direct tumor application of the C-terminal fragment of MIS, it is preferable that a final serum concentration of at least 0.1 nM, preferably about 0.1–1.0 nM, of the C-terminal fragment of MIS be achieved. Effective individual dosage through the additionally named means of administration can be readily determined by methods well known to those of ordinary skill in the art. For example, using the size ratio calculation as detailed above, one of ordinary skill in the art can determine optimal dosage levels for any means of administration. In treating a patient, it is preferable to achieve a serum level of at least 10 ng/ml of MIS. In treating a patient with the C-terminal fragment of MIS, it is preferable to achieve a serum level ranging from about 1 ng/ml to about 20 µg/ml of the C-terminal fragment of MIS.

Whether a vector contains a gene capable of expressing an "effective amount of MIS" or an "effective amount of the C-terminal fragment of MIS" can be determined following the protocols set forth in Example 4.

Compositions containing MIS or the C-terminal fragment of MIS or their functional derivatives may be administered orally, intravenously, intramuscularly, subcutaneously, or locally. Additional pharmaceutical methods may be employed to control the duration of action. Controlled release preparations may be achieved by the use of polymers to complex or adsorb MIS or the C-terminal fragment of MIS or their functional derivatives. The controlled delivery may be exercised by selecting appropriate macromolecules (for example polyesters, polyamino acids, polyvinyl pyrrolidone, ethylenevinylacetate, methylcellulose, carboxymethylcellulose, and protamine sulfate) and the concentration of macromolecules as well as the methods of incorporation in order to control release.

Another possible method to control the duration of action by controlled release preparations is to incorporate MIS or the C-terminal fragment of MIS into particles of a polymeric material such as polyesters, polyamino acids, hydrogels, poly(lactic acid) or ethylene vinyl acetate copolymers. Alternatively, instead of incorporating MIS or the C-terminal fragment of MIS into these polymeric particles, it is possible to entrap MIS or the C-terminal fragment of MIS in microcapsules prepared, for example, by coacervation techniques or by interfacial polymerization, for example, hydroxymethylcellulose or gelatin microcapsules and poly(methylmethacrylate) microcapsules, respectively, or in colloidal drug delivery systems, for example, liposomes, albumin microspheres, microemulsions, nanoparticles, and nanocapsules or in macroemulsions. Such teachings are disclosed in *Remington's Pharmaceutical Sciences*, supra (1980).

Pharmaceutical compositions which include the proteolytically cleaved MIS protein fragments of this invention can also include chemotherapeutic agents which are known to inhibit tumor growth in a human or animal. The pharmaceutical compositions including proteolytically cleaved MIS protein fragments can include both the N- and C-terminal fragments or the C-terminal fragment alone. When the N-terminal fragment is present in the composition, it may be further cleaved into smaller fragments by prolonged proteolysis. The chemotherapeutic agent included in this composition can be directed to any specific neoplastic disease. Such agents are described in *Goodman and Gilman's The Pharmacological Basis of Therapeutics*, 8th Ed., Pergamon Press, New York, N.Y., 1985. It is preferred, however, that the chemotherapeutic agent inhibit growth of the tumors of this invention.

In general, the chemotherapeutic agent which is combined with MIS or the C-terminal fragment of MIS will have an additive effect on the treatment of the tumors of this invention. This means that the quantity of chemotherapeutic agent used in treating the tumors of this invention can be reduced from the manufacturer's recommended dose, thereby reducing undesirable side effects. For example, for every quantity of chemotherapeutic agent that is reduced in the tumor treatment, an equivalent effective amount of MIS or the C-terminal fragment of MIS can be added.

It is to be understood that the use of the term "equivalent effective amount" does not necessarily mean an equivalent weight or volume quantity, but represents the quantity of MIS or the C-terminal fragment of MIS that offers an equal inhibition to tumor growth. This may have to be evaluated on a patient by patient case, but can be determined, for example, by comparing quantities that achieve equal size reduction ratios as defined above. Typically, chemotherapeutic agents which can be combined with MIS or the C-terminal fragment of MIS for treatment of the tumors of this invention will be effective between about 0.001 and 10.0 mg/kg body weight of the patient. Administration of the combination of MIS or C-terminal fragment of MIS and chemotherapeutic agent can be accomplished in the same manner as administration of the MIS or C-terminal fragment of MIS alone.

Included as chemotherapeutic agents in the pharmaceutical compositions of this invention are nitrogen mustards such as cyclophosphamide, ifosfamide, and melphalan; ethylenimines and methylmelamines such as hexamethylmelamine and thiotepa; pyrimidine analogs such as fluorouracil and fluorodeoxyuridine; vinca alkaloids such as vinblastine; epipodophyllotoxins such as etoposide and teniposide; antibiotics such as actinomycin D, doxorubicin, bleomycin, and mithramycin; biological response modifiers such as interferon α; platinum coordination complexes such as cisplatin and carboplatin; estrogens such as diethylstilbestrol and ethinyl estradiol; antiandrogens such as flutamine; and gonadotropin releasing hormone analogs such as leuprolide. Other compounds such as decarbazine, nitrosoureas, methotrexate, diticene, and procarbazine are also effective. Of course, other chemotherapeutic agents which are known to those of ordinary skill in the art can readily be substituted as this list should not be considered exhaustive or limiting.

The expression of MHC genes is believed to correlate with the capacity of tumor cells to metastasize (Tanaka, K., et al., *Science* 228:26 (1985); Eisenbach, L., et al., *Canc. Rev.* 5:1–18 (1986), herein incorporated by reference). The metastasis of a tumor cell is a complex multi-step process, involving detachment of tumor cells from a local growth, invasion of intercellular matrices, penetration of basement membranes of blood vessels, circulation while undergoing homotypic aggregation, extravasation, and induction of angiogenesis in the target organ.

Tumors which are metastatic have been found to express depressed levels of certain MHC antigens, and in particular, the MHC class I antigen H-2K. Such metastatic tumors may, however, express normal or elevated levels of a second MHC class I antigen known as H-2D. In contrast, nonmetastatic tumors have been found to express normal or elevated levels of the H2-K antigen, but to express depressed levels of the H2-D antigen These results have suggested that the ability of a tumor cell to metastasize is impaired if the cell can be "recognized" by cytotoxic T cells. In general, such cytotoxic T cells ("CTL") recognize and destroy foreign or tumor cells through the recognition of a non-MHC cell surface epitope (i.e. a conventional antigen) which is in association with a class I MHC molecule on the surface of the foreign or tumor cell. Thus, the presence of the H-2K class I MHC antigen on a tumor cell is believed to increase the capacity of that cell to be recognized by a CTL i.e. to increase the cell's immunogenicity (Eisenbach, L., et al., *Canc. Rev.* 5:1–18 (1986); Zinkernagel, R. M., et al., *Contemp. Top. Immunobiol.* 7:179–220 (1977); Warnet, D., et al., *J. Exper. Med.* 141:573–583 (1975); Warnet, D., et al., *J. Exper. Med.* 144:654–661 (1976); Miller, S.D., et al., *J. Exper. Med.* 147:788–799 (1978)). In contrast, expression of H2-D is believed to decrease immunogenicity, and thus permit cellular metastases to occur.

In accordance with these suggestions, metastatic tumors have been found to manifest abnormally low levels of H-2K MHC class I antigens on their cell surfaces (Eisenbach, L., et al., *Int. J. Canc.* 32:113–120 (1983); Eisenbach, L., et al., *Int. J. Canc.* 34:567–573 (1984); Eisenbach, L., et al., *In: Cancer Invasion and Metatasis: Biologic and Therapeutic Aspects* (Nicolson, G. L., et al., eds.), Raven Press, NY, pp. 101–121 (1984)); Eisenbach, L., *Mod. Trends Hum. Leukemia* 6:449–507 (1985); Eisenbach, L., et al., *Trans. Proc.* 17:729–734 (1985); Eisenbach, L., et al., *In: Biochemistry and Molecular Genetics of Tumor Metatasis* (Lapis, K., et al., eds.) Boston-Dordrecht-Lancaster: Martinus Nijhoff Publ. 167–184 (1986)). Interferon has been shown to induce elevated expression of the H2-D and H2-K class I MHC antigens (Fellous, M., et al., *Proc. Natl. Acad. Sci. U.S.A.* 79:3082–3086 (1982)). Treatment of cells with a- or B-interferon has, however, been found to preferentially increase expression of the H2-D antigen, and thus to increase the metastatic properties of certain tumor cells (Eisenbach, L., *Int. J. Canc.* 32:113–120 (1983)). In contrast, γ-interferon has been found to preferentially stimulate expression of the H-2K class I MHC antigen, and to therefore decrease the metastatic competence of tumor cells (Eisenbach, L., et al., *In: Biochemistry and Molecular Genetics of Tumor Metatasis* (Lapis, K., et al., eds.) Boston-Dordrecht-Lancaster: Martinus Nijhoff Publ. 167–184 (1986)).

Retinoic acid has been found to be capable of regulating the expression of the H2-D class I MHC antigen, but not of the H2-K class I MHC antigens (Eisenbach, L., et al., *Int. J. Canc.* 32:113–120 (1983)). Accordingly, retinoic acid increases the metastatic capacity of tumor cells.

The product of the c-fos gene has been found to be capable of regulating the expression of both the H2-K and H2-D antigens (Eisenbach, L., et al., *Canc. Rev.* 5:1–18 (1986)).

In summary, the expression of the H-2K MHC class I antigen has been found to be inversely related to the capacity of a tumor cell to metatasize. Thus, increased H-2K expression is associated with nonmetastatic tumor growth. Moreover, agents capable of generally increasing MHC class I expression appear to reduce the capacity of tumor cells to proliferate.

In contrast, the H-2D MHC class I antigen has been found to be associated with tumor metatasis. An increase in H-2D expression is associated with increased metastatic activity.

Embryonic growth and development, though explosive, is stringently controlled, responding to exacting genetic and environmental signals, as well as rigorous temporal signals. The embryo evolves in a sea of growth factors and growth inhibitors which play a role in accelerating or delaying disproportionate development. However, little is understood about the mechanisms by which these disparate factors exert their control at that time.

Embryonic development is characterized by a progressive increase in the expression of Major Histocompatibility Complex (MHC) Class I and II mRNA and protein. However, the level of expression differs widely between organs and tissue types.

As a general rule, the immunoprivilege enjoyed by fetal allografts (Foglia, *Annals of Surgery* 204:402–410 (1985); Statter, M. B., et al., *J. Urol.* 139:204 (1988)), is inversely proportional to the MHC burden that the tissue expresses. As discussed below, younger fetal tissue with low MHC expression survives transplantation better than older tissue with higher MHC expression.

With these two observations in mind, i.e., that growth modulators are essential to orderly fetal growth, and that survival of fetal grafts is inversely proportional to MHC expression, the effect that growth factors and growth inhibitors might have on expression of MHC mRNA was studied using Epidermal Growth Factor (EGF) and Müllerian Inhibiting Substance (MIS).

The expression of EGF and MIS appear to comprise a dyad regulatory control mechanism. For example, the regression of the male Müllerian duct caused by MIS can be inhibited by EGF (Hutson *Science* 223:586 (1984)). Oocyte meiosis inhibition caused by MIS can be blocked by EGF (Ueno et al., *Endocrinology* 123:1652–1659 (1988)), and conversely EGF induced autophosphorylation of the EGF receptor in A431 cells can be inhibited by MIS (Coughlin et al. (*Molec. Cell Endocrinol.* 49:75 (1987)). Using these two modulators and γ-interferon as a known enhancer of Class I antigen expression a fetal tissue was sought in a mouse strain containing well established markers for H-2 class I and II loci. Secondary fetal fibroblasts from the C57B1/6 strain were selected, from which one could generate large numbers of cells for RNA extraction. Other, similar mouse strains or cells derived from humans (such as lymphocytes, etc.) could alternatively be employed.

Secondary fetal fibroblasts from the C57B1/6 strain were found to express measurable levels of Class I mRNA. EGF and MIS were tested for their capacity to modulate the expression of the antigens of the MHC and found to be capable of precisely governing the expression of MHC class I mRNA. MHC mRNA expression was found to be up-regulated by the growth inhibitor MIS and down-regulated by the EGF growth factor.

The ability of MIS to increase the expression of MHC class I mRNA suggests that expression of the MHC class I antigens will be also be increased in the presence of MIS. As discussed above, such an increase in the expression of MHC class I antigen expression is associated with increased immunogenicity, and hence, decreases the capacity of a tumor to metastasize. The discovery that MIS is capable of increasing the expression of MHC class I mRNA is one aspect of the present invention, and provides a method of controlling the growth of cells during embryonic development and during uncontrolled tumor growth.

Human Immunodeficiency Virus (HIV) is believed to be the causal agent for AIDS (Acquired Immunodeficiency Disease Syndrome). HIV is believed to cause an immunosuppressed state in an individual through its capacity to recognize and selectively inactivate T helper cells. The virus has been found to express antigens whose domains are similar in sequence to those of the MHC class II antigens (Golding, H. et al., *J. Exper. Med.* 167:914–923 (1988)). The virus has been hypothesized to confer an immune suppressed condition on an individual by attaching to the T4 (CD4) receptor of helper T lymphocytes, and (since its domains resemble those of a class II MHC molecule) of thereby provoking an immune response against any cell bearing a class II MHC molecule (Ziegler, J. L. et al., *Clin. Immunol. Immunopath.* 41:305–313 (1986)). One result of this immune response is a progressive disruption of antigen recognition, and ultimately the expression of MHC class I antigens.

Because AIDS infection is, therefore, characterized by an impairment of MHC class I antigen expression, it frequently results in the establishment of debilitating tumors (such as Kaposi's sarcomas). The ability of interferons (such as α and γ) to effect expression of MHC class I antigens provides a theoretical basis for their use in treating such tumors in AIDS patients. The use of interferons in the treatment of AIDS is reviewed by Krown, S. E. (In: *Developments in Medical Virology: Clinical Aspects of Interferons,* (Revel, M., Ed.), Kluwer Academic Pub., Boston, Mass., pp. 62–74 (1988)).

Since MIS shares with γ-interferon the capacity to increase the expression of MHC class I mRNA, it may be employed in the same manner as interferon in the treatment of immunodeficiency diseases. Thus, individuals who suffer from AIDS or other diseases which result from the prevalence of an immunosuppressed state can be treated with MIS or its functional derivatives or agonists in order to increase their immune response. MIS, its functional derivatives, or its agonists can be used to ameliorate the immune suppressed state of such patients.

As discussed in further detail below, the MIS of the present invention, its functional derivatives or its agonists, may be provided in combination (i.e. co-administered) with interferon or other antiviral therapies (such as AZT, etc.). Such therapies are reviewed by Clumeck, N., et al. (*Amer. J. Med.* 85:165–172 (1987)); Jacobs, J. L. (In: *Year in Immunology Vol.* 3 (Cruse, J. M. et al., Eds.), Karger AG, Basel, pp. 303–309 (1988)) and Sarin, P.S. (*Ann. Rev. Pharmacol. Toxicol.* 28:411–428 (1988)), all of which references are herein incorporated by reference.

Although, as discussed above, it is desirable to enhance the immunogenicity of tissue to suppress tumor metastasis or as an adjunct therapy in the treatment of immunosuppressive or immunodeficient individuals, it may alternatively be desirable to decrease the immunogenicity of tissue (such as organs, etc.), for example, as a prelude to transplantation therapies.

Rejection responses in transplanted tissue are initiated by antigenic disparity between graft and host. Medawar, P. B. (*Symp. Soc. Exp. Biol.* 7: 320 (1953)) observed that although the conceptus is analogous to allografted tissue in that half of its antigenic endowment comes from the father (Raghupathy R. et al., In: *Immunobiology of Transplantation, Cancer, and Pregnancy,* Ray, P. K., Ed. Pergamon Press, Inc., pp. 257 (1983)), the fetus is rarely rejected by the mother. Medawar suggested that the success of the fetal allograft was attributable to the fetus being non-immunogenic. For this reason, experiments designed to study the strategies used by the fetus to escape rejection, were designed and used to determine ways in which donor tissue could be modulated to augment classic clinical immunotherapies which suppress recipient response. Thus the expression of MHC products in different tissues of the fetus was studied, and correlated with the ability of the tissue to survive grafting.

Allografts of mid-gestational renal tissue survived up to 20 days after implantation (Foglia R. P. et al., *Annals of Surgery* 204:402 (1986); Foglia R. P. et al., *J. Ped. Surg.*

21:608 (1986)) and mid and late gestational and post-natal testicular tissue (Statter M. B. et al., *J. Urol.* 139:204 (1988)) survived up to 45 days after transplantation beneath the renal capsule of adult non-immunosuppressed outbred rat hosts, while corresponding adult tissue was promptly rejected. Based on these and other findings (Kirkwood K. J. et al., *Embryol. Exp. Morph.* 61:207 (1981); Edidin M., *Transplantation* 2:627 (1984); Ozato, K. et al., *Proc. Natl. Acad. Sci. U.S.A.* 82:2427 (1985); Fahrner, K. et al., *EMBO J.* 6:1265 (1984)) we attempted to determine if the observed difference in graft survival between testis and kidney, and between younger and older grafts, could be explained by differential tissue expression of products of the major histocompatibility complex and if these parameters changed during grafting.

Using northern analysis and immunohistochemical staining constituitive expression of Class I and II mRNA and protein was measured during ontogeny, comparing fetal, postnatal, and adult renal and testicular tissue. Renal and testicular tissue from C57BL/6 (H-2b) mice were dissected at each stage and implanted beneath the renal capsule of adult recipient congenic B10.A (H-2k) mice. Growth and morphology of the graft were examined at specific times after implantation and induction or suppression of Class I and II mRNA and protein in the implanted tissue was correlated with graft survival.

These studies indicated that constitutive expression of MHC was lower in the fetus than in the adult, and that timing of expression during development was stringently controlled for each organ. Induction of Class I and II mRNA occurred after transplantation and was correlated with the degree of lymphocytic infiltrate, but Class I and II protein was suppressed. This lack of protein expression provides an explanation for fetal graft survival after transplantation. Similarly, it supports the conclusion that antagonists of MIS may be used to reduce the immunogenicity of transplant tissue.

One aspect of the present invention, therefore, concerns the use of EGF and its functional derivatives and agonists (or, more preferably, the use of antagonists of MIS) to decrease the expression of class I MHC antigens in tissue or organs being prepared for transplantation.

The present invention is directed toward the use of MIS and EGF and their "functional derivatives" in the treatment of metastatic tumors, immunosuppressive and immunodeficiency diseases, and organ and tissue transplant. The MIS or EGF molecule disclosed herein are said to be "substantially free of natural contaminants" if preparations which contain them are substantially free of materials with which these products are normally and naturally found.

A "functional derivative" of either MIS or EGF is a compound which posesses a biological activity (either functional or structural) that is substantially similar to a biological activity of MIS or EGF, respectively. The term "functional derivatives" is intended to include the "fragments," "variants," "analogs," or "chemical derivatives" of a molecule. A "fragment" of a molecule such as either MIS or EGF, is meant to refer to any polypeptide subset of the molecule. Fragments of either MIS or EGF which have activity and which are soluble (i.e not membrane bound) are especially preferred. A "variant" of a molecule such as either MIS or EGF is meant to refer to a molecule substantially similar in structure and function to either the entire molecule, or to a fragment thereof. A molecule is said to be "substantially similar" to another molecule if both molecules have substantially similar structures or if both molecules possess a similar biological activity. Thus, provided that two molecules possess a similar activity, they are considered variants as that term is used herein even if the structure of one of the molecules not found in the other, or if the sequence of amino acid residues is not identical. An "analog" of a molecule such as either MIS or EGF is meant to refer to a molecule substantially similar in function to either the entire molecule or to a fragment thereof. As used herein, a molecule is said to be a "chemical derivative" of another molecule when it contains additional chemical moieties not normally a part of the molecule. Such moieties may improve the molecule's solubility, absorption, biological half life, etc. The moieties may alternatively decrease the toxicity of the molecule, eliminate or attenuate any undesirable side effect of the molecule, etc. Moieties capable of mediating such effects are disclosed in *Remington's Pharmaceutical Sciences* (1980). "Toxin-derivatized" molecules constitute a special class of "chemical derivatives." A "toxin-derivatized" molecule is a molecule (such as either MIS or EGF or an antibody to their receptors) which contains a toxin moiety. The binding of such a molecule to a cell brings the toxin moiety into close proximity with the cell and thereby promotes cell death. Any suitable toxin moiety may be employed; however, it is preferable to employ toxins such as, for example, the ricin toxin, the diphtheria toxin, radioisotopic toxins, membrane-channel-forming toxins, etc. Procedures for coupling such moieties to a molecule are well known in the art.

As used herein, the term "agonist" is intended to refer to an agent which enhances the physiologic response of an organ or organism to the presence of a second agent. Thus, an agonist of MIS increases the effectiveness of MIS by increasing an individual's response to the presence of MIS. Similarly, an agonist of EGF increases the effectiveness of that agent. Examples of agonists of MIS include antibody (or fragments thereof) to EGF, interferon ($\alpha$, $\beta$, or $\gamma$), etc. EGF is an antagonist of MIS.

As used herein, the term "antagonist" is intended to refer to an agent which diminishes the physiologic response of an organ or organism to the presence of a second agent. Thus, an antagonist of MIS would decrease the effectiveness of MIS by decreasing an individual's response to the presence of MIS. Similarly, an antagonist of EGF decreases the effectiveness of that agent. An example of an antagonist of EGF is antibody (or fragments thereof) to EGF. MIS, and interferon are examples of antagonists of EGF.

The therapeutic advantages of either MIS or EGF (or their functional derivatives, or agonists) may be augmented through the use of functional derivatives of either compound possessing additional amino acid residues added to enhance coupling to carrier or to enhance the activity of the either MIS or EGF. The scope of the present invention is further intended to include functional derivatives of either MIS or EGF which comprise therapeutically active peptide fragments of these molecules. Such fragments may lack certain amino acid residues, or may contain additional amino acid residues, so long as such derivatives exhibit the capacity to affect MHC mRNA expression. Especially included are MIS and EGF derivatives which may lack (or contain) one or two or three (additional) amino acid residues from either their amino or carboxyl termini.

Either MIS or EGF or their functional derivatives or agonists may be obtained either synthetically, through the use of recombinant DNA technology, or by proteolysis.

The therapeutic effects of either MIS (or EGF) may be obtained by providing to a patient either the entire MIS (or EGF) molecule, or any of its functional derivatives. Such therapeutic effects can be achieved (or enhanced) through the (additional) administration of either an agonist of MIS (or EGF), or an antagonist of EGF (or MIS). As used herein, two agents are said to be co-administered when they are provided to tissue or to an individual in such close proximity of time that both agents can be observed to exert a detectable effect on the tissue or individual at the same time.

A composition is said to be "pharmacologically acceptable" if its administration can be tolerated by a recipient patient. Such an agent is said to be physiologically significant if its presence results in a detectable change in the physiology of a recipient patient.

The metastasis-supressive activity of MIS may be provided to a recipient by providing either MIS, or a functional derivative or agonist of MIS. Suppression of metastasis may be achieved through the administration of antibody to EGF or to its cellular receptor, or through the administration of a toxin-derivatized EGF molecule. MIS can be co-administered with interferon (or other agonists) in order to increase the effectiveness of the therapy.

Likewise, the capacity of EGF to enhance immunogenicity may be provided to a recipient by providing either EGF, or a functional derivative or agonist of EGF. Enhancement of immunogenicity may be achieved through the administration of antibody to MIS or to its cellular receptor, or through the administration of a toxin-derivatized MIS molecule.

It is additionally possible to combine the administration of MIS and EGF (or their functional derivatives or agonists) to a patient in order to modulate the effects of these compounds on the expression of the MHC antigens, immunogenicity, or tumor metastasis. In view of the teachings of the present invention, other agents, or combinations of agents will also be perceived by those of ordinary skill. Such agents and combinations are intended to be among the equivalents of the present invention.

In providing a patient with either MIS or EGF (or a fragment, variant, or derivative thereof) to a recipient patient, the dosage of administered agent will vary depending upon such factors as the patient's age, weight, height, sex, general medical condition, previous medical history, etc. In general, when providing either MIS or EGF molecules or their functional derivatives, agonists or antagonists to a patient, it is preferable to administer such molecules in a dosage which ranges from about 1 pg/kg to 10 mg/kg (body weight of patient) although a lower or higher dosage may also be administered.

Either MIS or EGF (or their functional derivatives, agonists, or antagonists) may be administered to patients intravenously, intramuscularly, subcutaneously, enterally, or parenterally. When administering such compounds by injection, the administration may be by continuous infusion, or by single or multiple boluses.

The compounds of the present invention are intended to be provided to recipient subjects in an "effective amount." An amount of a compound is said to be "effective" if, with regard to the treatment of metastatic tumors, the dosage, route of administration, etc. of the compound is sufficient to suppress or prevent the metastasis of the tumor. Similarly, with respect to the treatment of immunocompromised individuals, an amount of a compound is said to be "effective" if the dosage, route of administration, etc. of the compound is sufficient to alleviate or improve the immune state of the individual.

The administration of such compounds may be for either a "prophylactic" or "therapeutic" purpose. When provided prophylactically to suppress metastasis, the compounds are provided in advance of the detection of any metastasis (for example, at, or shortly after the time of tumor detection). The prophylactic administration of the compounds serve to prevent or attenuate any subsequent metastasis. When provided therapeutically to suppress metastasis, the compounds are provided at (or shortly after) the detection of an actual metastatic process. The therapeutic administration of the compounds serve to attenuate such actual metastasis. The compounds of the present invention may, thus, be provided either prior to the onset of a metastatic process (so as to suppress an anticipated metastasis) or after the initiation of such a process.

When provided as an adjunct therapy in the treatment of immunosuppressive or immunodeficiency diseases, the compounds of the present invention may also be provided either prophylactically (i.e. prior to the recognition of such immunosuppressed or immunodeficient state (as to an individual having symptoms of ARC - AIDS Related Condition) ), or therapeutically (as to an individual exhibiting symptoms of such an immunocompromized state).

In employing EGF, its antagonist, or its functional derivatives (or any other suitable antagonist of MIS) to prevent or attenuate the rejection of organs or tissue in a transplant recipient, such agents can be administered (in any of the manners described above) to the transplant recipient at, or prior to, the time of transplantation.

Alternatively, such compounds can be provided to the organ donor at, or after, the time of death or donation. When provided in this manner, the organ or tissue to be donated will be perfused with the MIS antagonist in order to decrease the expression of MHC class I antigens on the surfaces of the cells of the donated material. In this manner, the immunogenicity of such materials will be diminished, and an immune rejection avoided, delayed or lessened. Such perfusion may be either systemic (as by introducing the MIS antagonist in a manner so as to cause it to be generally present throughout all or most of the organs or tissue of the donor) or localized (as by bathing, injecting or perfusing such compounds into an isolated organ, tissue or region).

In a further embodiment of the invention, an organ or tissue selected for transplantation may be provided with an MIS antagonist (by bathing, injection, or perfusion) after the removal of such material from the donor. The organ may be prepared for storage pending transplantation in a solution or composition containing an MIS antagonist.

With respect to transplantation, an amount of a compound is said to be "effective" if the dosage, route of administration, etc. of the compound is sufficient to attenuate, delay or prevent the rejection of the transplanted material.

The MIS or EGF molecules of the present invention (and their functional derivatives, agonists and antagonists can be formulated according to known methods to prepare pharmaceutically useful compositions, whereby these materials, or their functional derivatives, are combined in admixture with a pharmaceutically acceptable carrier vehicle. Suitable vehicles and their formulation, inclusive of other human proteins, e.g., human serum albumin, are described, for example, in Remington's Pharmaceutical Sciences (16th ed., Osol, A., Ed., Mack, Easton Pa. (1980)). In order to form a pharmaceutically acceptable composition suitable for effective administration, such compositions will contain an effective amount of either MIS or EGF molecule, or their functional derivatives, agonists, or antagonists, together with a suitable amount of carrier vehicle.

Additional pharmaceutical methods may be employed to control the duration of action. Control release preparations may be achieved through the use of polymers to complex or absorb either MIS or EGF, or their functional derivatives, agonists, or antagonists. The controlled delivery may be exercised by selecting appropriate macromolecules (for example polyesters, polyamino acids, polyvinyl, pyrrolidone, ethylenevinylacetate, methylcellulose, carboxymethylcellulose, or protamine, sulfate) and the concentration of macromolecules as well as the methods of incorporation in order to control release. Another possible method to control the duration of action by controlled release preparations is to incorporate either MIS or EGF molecules, or their functional derivatives, agonists, or antagonists, into particles of a polymeric material such as polyesters, polyamino acids, hydrogels, poly(lactic acid) or ethylene vinylacetate copolymers. Alternatively, instead of incorporating these agents into polymeric particles, it is possible to entrap these materials in microcapsules prepared, for example, by coacervation techniques or by interfacial polymerization, for example, hydroxymethylcelluloseorgelatine-microcapsulesandpoly(methylmethacylate) microcapsules, respectively, or in colloidal drug delivery systems, for example, liposomes, albumin microspheres, microemulsions, nanoparticles, and nanocapsules or in macroemulsions. Such techniques are disclosed in Remington's Pharmaceutical Sciences (1980). The compositions of the present invention may be prepared as articles of manufacture, such as "kits." Preferably, such kits will contain two or more containers which are specially adapted to receive MIS (or EGF) or one of their functional derivatives, and an agonist of MIS (or EGF).

The disclosures of all references, patent applications and patents recited herein are hereby incorporated by reference.

Having now generally described the invention, the same will be more readily understood through reference to the following examples which are provided by way of illustration, and are not intended to be limiting of the present invention, unless specified.

EXAMPLE 1

I. Materials and Methods

A. Production and Purification of rhMIS

After cloning MIS cDNA and genomic DNA, dihydrofolate reductase deficient CHO were cotransfected with a linear transcript of both the human MIS and the dihydrofolate reductase genes according to the method of Cate (Cate et al., *Cell* 45:685–698 (1986)). The transfected CHO cells were amplified in Methotrexate and grown at 37° C. in alpha minimal essential medium without ribonucleosides and deoxyribonucleosides, supplemented with 10% bovine MIS-free female fetal calf serum (FCS). Two different MIS purification protocols were used to provide either partially pure or homogeneous MIS. The first employed serial anion exchange and dye affinity chromatography (DG-MIS) according to the method of Budzik (Budzik et al., *Cell* 34:307–314 (1983)) to provide a 1–10% concentration of MIS. The second method employed the immunoaffinity chromatography method (IAP-MIS) detailed in U.S. patent application Ser. No. 07/683,957 to provide a 90–95% concentration of MIS.

The immunoaffinity chromatography method used herein was directed toward the recovery of recombinant human MIS (rhMIS). The protein was purified from the conditioned media of Chinese hamster ovary (CHO) cells, transfected with a linear construct of the human rhMIS gene and the DHFR gene, amplified by 30 nM Methotrexate selection, grown to confluence in four liter bioreactors on stainless steel coils as described by Epstein (Epstein et al., *In Vitro Cell. and Devel. Biol.* 25(2):213–6 (1989)) or on modified roller bottles in alpha-Modified Eagle's Medium ($\alpha$-MEM–), supplemented with 5% female fetal calf serum (FFCS), 10 mg/ml Amikacin, 1.3 gm/l 1-glutamine, 2.0 gm/l d-glucose, and 0.1 gm/l sodium pyruvate, in the absence of nucleosides. The medium was collected every 3–4 days, and stored at –20° C. Media were thawed and filtered through Whatman #4 filter paper to remove debris, concentrated 20x an a Minitan (Millipore) with a 30 kDa exclusion ultrafilter, and stored at –70° C., until purification. A 5 ml immunoaffinity column was constructed using approximately 50 mg of a Protein A-Sepharose (BioRad) purified monoclonal anti-human rhMIS antibody [6E11] as described by Hudson (Hudson et al., *J. Clin. Endocrinol. Metab.* 70:16–22 (1990)), and covalently attached to Affigel-10 agarose resin (BioRad), per the manufacturer's instructions (approximately 80% coupling efficiency). The column was equilibrated with 100 mls of 20 mM HEPES, pH 7.4, and 200 ml of the concentrated media loaded at 1 column volume/hour at 4° C. After loading, the column was washed with 20 mM HEPES, pH 7.4, until the absorbance at 280 nm returned to baseline (60–100 mls).

Elution of rhMIS bound to this column was achieved using 2.0M sodium thiocyanate (NaSCN); or 1M Acetic acid, 20 mM HEPES, pH 3.0, with or without a pre-elution step containing 0.5M NaCl, 1 mM EDTA, 0.001% NP-40, 20 mM HEPES, pH 7.4. The majority of the rhMIS protein eluted in a single 2 ml fraction, which was immediately neutralized with either NaOH or $NH_4OH$ to a pH between 7.0 and 7.4. Depending on the initial pH of the fraction and technique of neutralization, dilutional effects ranged from 10–50%.

The biological activity of MIS was detected in vitro using the rat Müllerian duct regression organ culture assay of Donahoe (Donahoe et al., *J. Surg. Res.* 23:141–148 (1977)). MIS concentrations were estimated using an enzyme-linked immunosorbent assay (ELISA) for MIS according to the method of Hudson supra. Protein concentrations were measured by the method of Bradford (Bradford, M. M., *Anal. Biochem.* 72:248–254 (1976)).

B. Preparation of Monoclonal Antibody for MIS Absorption.

Monoclonal antibody was produced by immunizing female A/J mice (Jackson Laboratory, Bar Harbor, Me.) with immunoaffinity purified rhMIS using methods previously described for bovine MIS (Hudson et al., *J. Clin. Endocrinol. Metab.* 70:16–22 (1990); Mudgett-Hunter et al., *J. Immunol.* 128:1327–33 (1982)). Spleen cells producing anti-MIS antibodies were harvested and hybridomas were produced as described by Kohler (Kohler, G., *Immunol. Methods* 2:285–98 (1981)). A monoclonal line (6E11) was selected and amplified in Dulbecco's modified essential medium supplemented with 15% FCS. The antibody was precipitated from 6E11 conditioned medium with 50% $(NH_4)_2SO_4$, and further purified by protein A-Sepharose CL-4B (Sigma, St. Louis, Mo.) chromatography.

C. Cell Lines

A431, a cell line derived from a human vulvar epidermoid carcinoma, HT-3 from a human lymph node metastasis of a cervical carcinoma, NIH:OVCAR-3 from a human ovarian adenocarcinoma, HEC-1-A from a human endometrial adenocarcinoma, RT4 from a human bladder transitional-cell papilloma, and Hep 3B from a human hepatocellular carcinoma were obtained from American Type Culture Collection. OM431, from a human ocular melanoma, was obtained from Dr. James Epstein of Massachusetts General Hospital.

The A431, HT-3, NIH:OVCAR-3, OM431 and Hep 3B cells were maintained with alpha minimal essential medium with ribonucleosides and deoxyribonucleosides (α-MEM+) supplemented with 10% female FCS and 2 mM L-glutamine. HEC-1-A and RT4 were maintained with McCoy's 5A medium supplemented with 10% female FCS. Before study, cells were serially subcultured, then trypsinized at 70–80% confluency to achieve synchrony. This proliferating cell population was then centrifuged at 1500 RPM for 5 minutes and resuspended with 10% female FCS supplemented medium. Cells were counted in a hemocytometer.

D. Semisolid Medium (Double Layer) Colony Inhibition Assay

The effects of IAP-MIS and the salt eluted fraction from the immunoaffinity column (IAP-salt) were tested using A431, HT-3, HEC-IA, NIH:OVCAR-3, OM431, and Hep 3B cells in the conventional double layer agarose colony inhibition assay of Hamburger (Hamburger et al., *Science* 197:461–463 (1977); Hamburger et al., *J. Clin. Invest.* 60:846–854 (1977)). The underlayer of the 35 mm culture dishes contained 1 ml of 0.6% agarose (Sigma, St. Louis, Mo.) in 10% female FCS supplemented α-MEM+. The overlayer consisted of 0.3% agarose in 10% female FCS supplemented MEM+, the cells to be tested (50,000 cells/ml for A431, HT-3, and OM431; 25,000 cells/ml for HEC-1-A, NIH:OVCAR-3, and Hep 3B), epidermal growth factor (EGF) 10 ng/ml (Sigma, St. Louis, Mo.) and one of the following: (a) IAP-MIS (final concentration 30 nM); (b) IAP-salt (final protein concentration 19.3 µg/ml); or (c) vehicle buffer as a negative control. The dishes were incubated in humid air with 5% $CO_2$ at 37° C. for 10–21 days. Colonies with more than 30 cells were counted with an inverted microscope (Nikon). The results were expressed as percent survival relative to a control group (number of colonies in the test group×100/number of colonies in the control group).

E. Liquid Medium Colony Inhibition Assay

Single cell suspensions were placed and grown in 24-well culture plates (Falcon, Oxnard, Calif., #3047). After cell attachment, only those with good single cell dispersion without clumping were used for further study. Agents to be tested were added in a volume less than 1/10 of the total volume in a well, and were tested in triplicate. The cells were incubated in humid air with 5% $CO_2$ at 37° C. Colonies which formed in 5–7 days were stained with Giemsa solution and those with more than 30 cells were counted with an inverted microscope or by a computer based image analyzer.

F. Comparison of IAP-MIS and IAP-salt on Colony Formation

IAP-MIS (final concentration 30 nM) and IAP-salt (final protein concentration 19.3 µg/ml) were tested in the liquid medium colony inhibition assay using 0.3 ml per well of A431 (25,000 cells/ml), OM431 (25,000 cells/ml), HT-3 (5000 cells/ml) and RT4 (5000 cells/ml). EGF 50 ng/ml was added to A431 and OM431 to suppress monolayer growth but stimulate colony formation according to the method of Lee (Lee et al. *Exp. Cell Res.* 173: 156–162 (1987)). The result was expressed as percent survival relative to the vehicle buffer control.

G. Dose Dependent Inhibition of A431 Cells by MIS

After dilution in vehicle buffer, DG-MIS was tested in final concentrations of 0.9, 1.8, 3.5, and 7.0 nM using A431 cells (25,000 cells/ml, EGF 50 ng/ml) in the liquid medium colony inhibition assay. IAP-MIS was tested in concentrations of 12, 24, 48, and 96 nM. The results were expressed as percent survival relative to the vehicle buffer control.

H. Antibody Absorption of MIS

MIS monoclonal antibody (6E11) and normal rabbit IgG (Dako Corporation, Denmark Lot 108) were dialyzed into serum-free α-MEM+ before use. Previous experiments showed maximum absorption of MIS activity at MIS:Ab ratio of 1:3. Therefore, 17.4 µg of 6E11 was added to 5.6 µg of DG-MIS. Normal rabbit IgG was diluted with culture medium and added to MIS in the same 1:3 ratio to determine nonspecific absorption. An equivalent amount of protein purified from conditioned medium of untransfected wild type CHO cells served as a negative control when mixed 1:3 with antibody as above. The preparations were mixed at 4° C. for 12 hours.

Protein A Sepharose 9CL-4B (Sigma, St. Louis, Mo.), after being washed in serum free medium, was added and incubated at 4° C. for another 12 hours. The mixtures were centrifuged and the supernatants tested in the liquid medium colony inhibition assay using A431 cells (25,000 cells/ml, EGF 50 ng/ml). Percent survival of each group was calculated by comparing the number of colonies in each group to the wild type negative control.

I. Cotreatment of IAP-MIS and the Salt Eluted Fraction (IAP-salt)

IAP-MIS was mixed with an equal volume of IAP-salt (protein concentration 0.199 mg/ml) to give a final MIS concentration of 50 nM. It was tested using A431 cells (25,000 cells/ml, EGF 50 ng/ml) in the liquid medium colony inhibition assay and compared to IAP-MIS, IAP-salt, and vehicle buffer. Percent survival was calculated by comparing the number of colonies in each group to that of vehicle buffer negative control.

J. Cotreatment of MIS and Cisplatin

Cisplatin (Bristol Laboratory, Syracuse, N.Y.) was diluted in serum free culture medium to give concentrations of 0, 0.078, 0.156, 0.312 and 0.624 µg/ml and tested in triplicate with or without DG-MIS (final concentration 7 nM) using A431 cells (25,000 cells/ml, EGF 50 ng/ml) in the liquid medium colony inhibition assay. Vehicle buffer was used as negative control. The percent survival was calculated by comparing the number of colonies grown at each dose to that achieved in the vehicle buffer negative control.

K. Multicellular Tumor Spheroids Assay

Multicellular tumor spheroids of HT-3 and Hep 3B cells were produced by the method described by Yuhas et al. (Yuhas et al., *Cancer Res.* 37:3639–3643 (1977)). In brief, either $10^6$ cells of HT-3 or Hep 3B in 10 ml of 10% female FCS supplemented α-MEM +, were plated on the top of 1% agarose in a 10 cm culture dish and incubated in humid air with 5% $CO_2$ at 37° C. Spheroids usually formed in 2–5 days. 0.5 ml of 1% agarose was added to each well of a 24-well culture plate (Falcon, Oxnard, Calif., #3047) to form a bottom layer before use. Individual spheroids of similar size (approximately 250 μm diameter) were selected under a dissecting microscope and transferred by a micropipette at one spheroid per well containing 0.5 ml of 10% female FCS supplemented α-MEM+ on top of the agarose layer. The sizes of the spheroids on day 0 were measured by the longest diameter (L) and the diameter perpendicular to the longest one (W). Volume was then expressed as (L×W×W). Six spheroid containing wells of each cell type were treated either by DG-MIS (final concentration 7 nM) or vehicle buffer. Volumes were measured again at the 3rd, 6th and 9th day. The size ratio of each spheroid at different intervals was obtained by comparing it to the size of the same spheroid at day 0. The average size ratio of each group was plotted vs. time in a growth curve and compared to the other groups.

L. Subrenal Capsule Assay

Following the method of Bogden (Bogden et al., *Exp. Cell Biol.* 47:281–293 (1979)), which was later modified by Fingert (Fingert et al., *Cancer Res.* 47:3824–3829 (1987)), A431 and OM431 cells were tested. $10^7$ of the cells were centrifuged at 1500 RPM for 5 minutes to form a pellet. 15 μl of fibrinogen (Sigma, St. Louis, Mo., 20 mg/ml dissolved in PBS pH 7.4) was added to the pellet, followed by 8 μl of thrombin (Sigma, St. Louis, Mo., 20 unit/ml dissolved in double-strength Dulbecco's modified essential medium). The mixture was incubated at 37° C. for 15 min. The cell clot thus formed was cut into approximately 100 fragments (1 $mm^3$ each containing approximately $10^5$ cells) in preparation for implantation.

MIS was delivered by an Alzet mini-osmotic pump (#2001, Alza, Palo Alto, Calif.) placed in the peritoneal cavity at the time of tumor implantation. These pumps have a fill volume of 209±6 μl and release their contents at a rate of 1.03±0.04 μl/hr for approximately eight days of delivery time. The pumps were either filled with IAP-MIS (MIS: 159 μg/ml by ELISA) or with vehicle buffer. A total MIS dose of approximately 33 μg (230 nM) was given to each mouse in the MIS group over the course of the experiment.

Virus and pathogen free female CD-1 mice (10 weeks old, average weight 35 g, Charles River Breeding Laboratory, Wilmington, Mass.) were given whole body irradiation of 640 rads by a Mark-1 cesium-137 irradiation 16–24 hours before the experiment (Gajewski et al., *Surgical Forum* 38:468–470 (1987)). After inducing anesthesia with an intraperitoneal injection of 0.3 ml of 10% Pentobarbital (Abbott Laboratory, North Chicago, Ill.), an incision was made in the left flank of the mouse and the left kidney exteriorized. A subcapsular space was developed using a 19-gauge needle trocar. A cell clot was introduced into the space with a segment of 5-0 Nylon suture (approximately 1 mm in length), which was used both to calibrate ocular micrometer measurements and to localize the tumor. Twenty-four mice were implanted with A431 cell clots and 12 mice with OM431 cell clots. The longest diameter (L1) of the implant, the one perpendicular to the longest one (W1), and the length of the suture were measured with the ocular micrometer of a dissecting microscope. The animals were either treated by IAP-MIS or vehicle buffer delivered by the Alzet pumps placed in the peritoneal cavity. Blood samples at 6, 24, 48, 120 (fifth day) and 192 hours (eighth day) were obtained from selected animals by orbital bleeding and serum MIS levels were measured by ELISA. The animals were sacrificed on the eighth day. The longest diameter (L1) of the tumor, the one perpendicular to the longest one (W1), and the length of the suture were measured blindly by two independent investigators. After calibration of the measurements, the graft size ratio was represented by (L2×W1×W2/(L1×W1×W1). Histologic sections of the kidneys were also obtained and examined. Tumors with cystic change were excluded.

M. Statistical Analysis

The results of the liquid medium and semisolid medium colony inhibition assays were analyzed by the Chi square test, with or without Yates correction, while the multicellular spheroid and the subrenal capsule assays were tested by the Student t-test. $p<0.05$ was considered as statistically significant.

II. Results

A. Semisolid Medium (Double Layer) Colony Inhibition Assay

The percent survival of the various cell lines after incubation with 30 nM of IAP-MIS was 45% for A431, 47% for HT-3, 54% for HEC-1-A, 59% for NIH:OVCAR-3, 34% for OM431, and 114% for Hep 3B. When compared to controls, the survival after treatment with MIS in all cell lines except Hep 3B were significantly inhibited by IAP-MIS ($p<0.05$). The growth of Hep 3B was not inhibited by MIS. The percent survival after incubation with IAP-salt were 172% for A431, 93% for HT3, 92% for HEC-1-A, 120% for OM431, 105% for NIH:OVCAR-3 and 173% for Hep 133B. The stimulatory effect was significant for A431, OM431 and Hep 3B cells ($p<0.05$) (FIG. 1).

Figure 2:
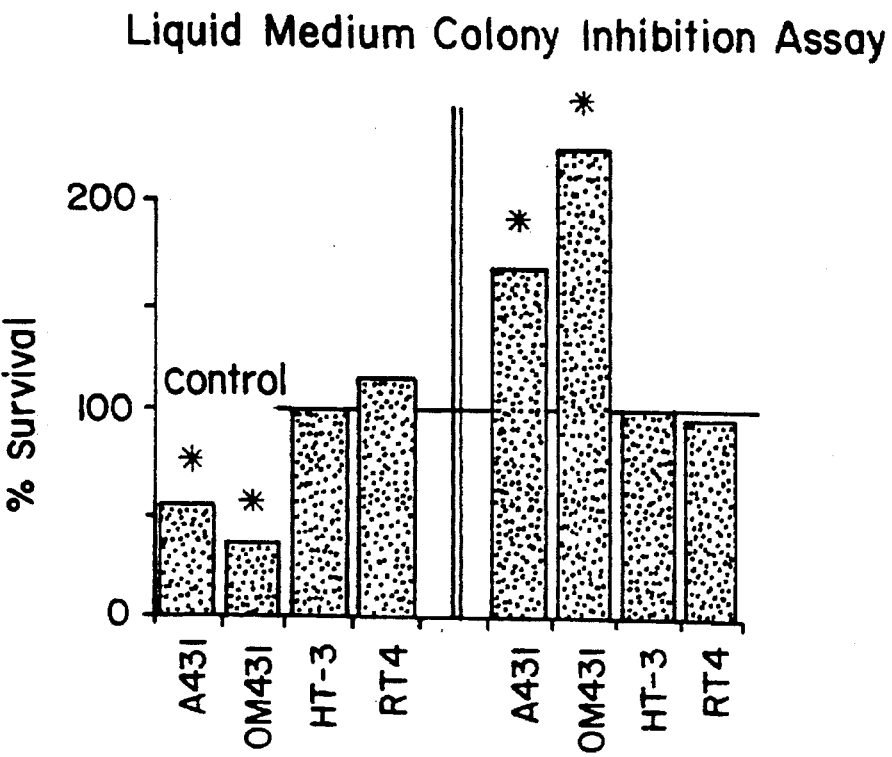
FIG. 2 shows the results of a liquid medium colony inhibition assay. The left side of the figure shows the effect of IAP-MIS in which colony formation of A431 and OM431 cells was significantly inhibited (30 nM). The right side of the figure shows the effect of the salt fraction preeluted from the immunoaffinity column (IAP-salt). The colony formation of A431 and OM431 cells was stimulated by IAP-salt. IAP-MIS and IAP-salt showed no effect on HT-3 and RT4 cells. The symbol "*" indicates p<0.05 when compared with control.

B. Effect of IAP-MIS and IAP-salt on Colony Formation using the Liquid Medium Colony Inhibition Assay The percent survival was 55.9% for A431, 36.8% for OM431, 100.5% for HT-3, and 115.8% for RT4 when treated with 30 nM of IAP-MIS. The percent survival was 169.0% for A431, 226.7% for OM431, 101.6% for HT-3 and 96.5% for RT4 when treated with IAP-salt (final protein concentration 19.3 μg/ml). The inhibitory effect of IAP-MIS and the stimulatory effect of IAP-salt were significant for A431 and OM431 colony formation ($p<0.05$) (FIG. 2).

C. Dose Dependent Inhibition of A431 Colony Formation by MIS

Figure 3:
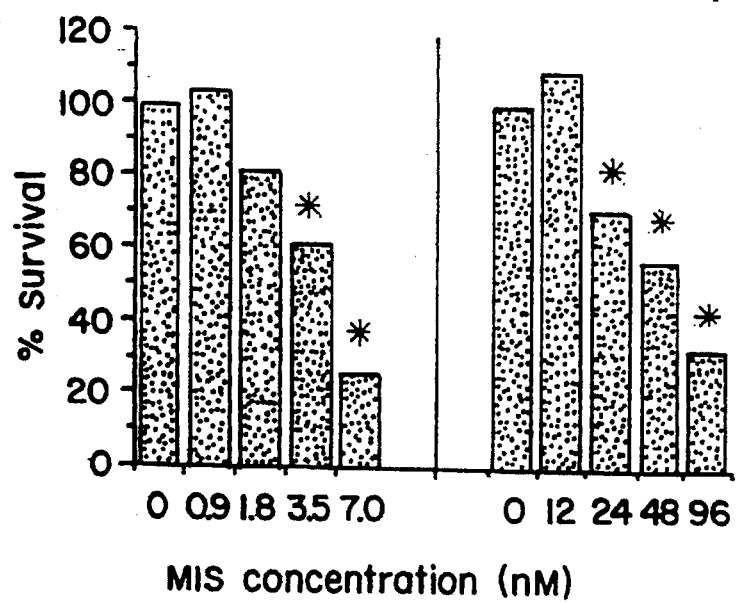
FIG. 3 shows dose dependent inhibition of A431 colony formation by MIS. The left side of the figure shows where MIS purified by dye affinity chromatography (DG-MIS) was tested in increasing doses using the liquid medium colony inhibition assay. Significant inhibition was seen at MIS concentrations of 3.5 and 7.0 nM. The fight side of the figure shows that IAP-MIS caused significant inhibition at concentrations of 24, 48 and 96 nM. The symbol "*" indicates p<0.05 when compared with controls.

The percent survival was 103.4%, 81.4%, 61.3% and 26.5% respectively, for DG-MIS concentrations of 0.9, 1.8, 3.5, and 7.0 nM. Significant inhibitions were seen with DG-MIS concentrations of 3.5 and 7.0 nM ($p<0.05$). The percent survival were 109.7%, 71.1%, 56.6%, and 33.3% respectively for IAP-MIS concentrations of 12, 24, 48, and 96 nM. Significant inhibitions were seen at IAP-MIS concentrations of 24, 48, and 96 nM (FIG. 3). DG-MIS thus was 10–14 times more potent than IAP-MIS.

D. Antibody Absorption of MIS

Figure 4:
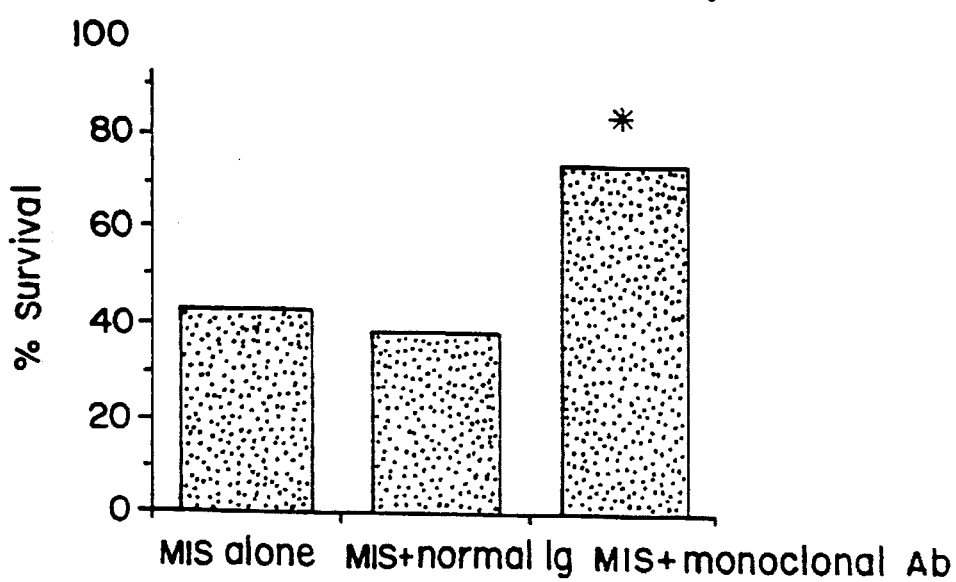
FIG. 4 shows antibody absorption of DG-MIS. The inhibitory effect of MIS of this degree of purity on A431 colony formation was significantly reduced after absorption with the MIS specific monoclonal antibody (6E11), but not after nonspecific absorption by normal IgG. The symbol "*" indicates p<0.05 when compared with MIS alone.

The MIS levels, measured by ELISA for MIS, were 9.0 nM for the positive control (MIS alone), 8.8 nM after normal IgG absorption (nonspecific) and 0.62 nM after the monoclonal antibody absorption (specific). All the wild type negative controls had an MIS level equal to 0. The percent survival was 42.9% for MIS alone, 38.0% for normal IgG (nonspecific absorption), and 74.2% for the monoclonal antibody (specific absorption). There was no significant nonspecific absorption of MIS activity (p>0.05 compared with negative control). The percent survival after the monoclonal antibody absorption was significantly higher than that of positive control (MIS alone) and normal IgG (FIG. 4).

E. The Salt Eluted Fraction (IAP-salt) Inhibits IAP-MIS

Figure 5:
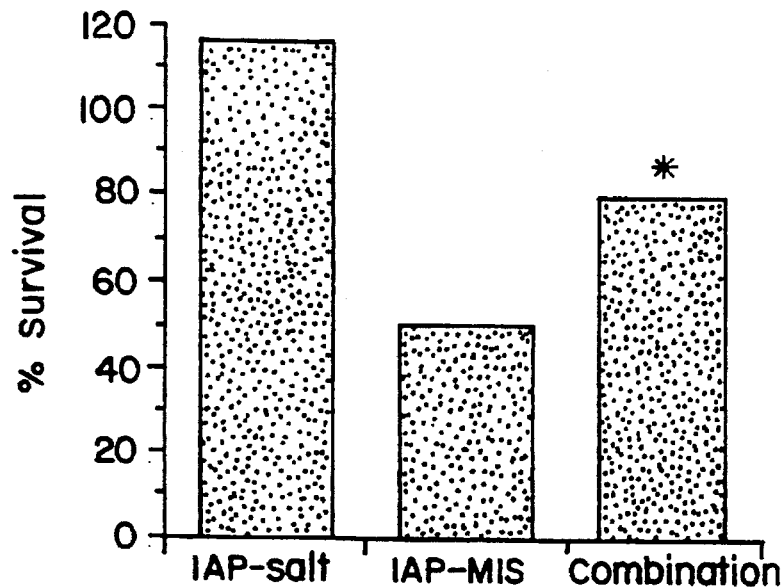
FIG. 5 shows the effects of various immunopurified fractions on A431 cells in the liquid colony inhibition assay. The IAP-MIS (50 nM), after salt and acid elution, inhibited colony growth, whereas the salt eluted fraction stimulated growth. When recombined, of these two preparations reduces MIS inhibitory effect. The percent survival of the combination was significantly higher than that of MIS alone. The symbol "*" indicates $p<0.05$ when compared with IAP-MIS alone, although the MIS concentrations were the same.

The percent survival of A431 cells was 51.3% for IAP-MIS alone (50 nM), 116.9% for IAP-salt alone and 81.6% for the combination of these two (MIS 50 nM). The difference between IAP-MIS alone and the combination of IAP-MIS/IAP-salt was significant (p<0.05) (FIG. 5). SDS gel electrophoresis was performed after reduction of IAP-salt and two separate preparations of IAP-MIS. Several bands of protein in the IAP-salt were seen in the region of 14–43 kDa, but were absent in the IAP-MIS.

F. Additive Effect of Cisplatin and MIS

Figure 6:
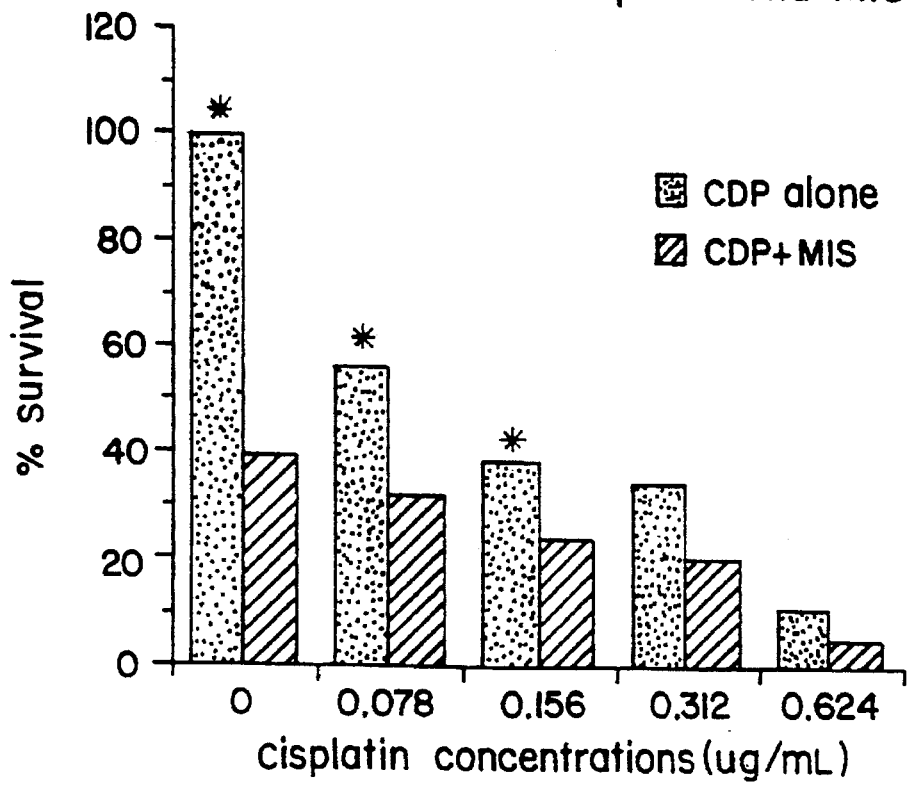
FIG. 6 shows the additive effect of cisplatin and DG-MIS. When cisplatin and MIS were tested on A431 cells in the liquid medium colony inhibition assay, their effects were additive at cisplatin concentrations of 0.078 and 0.156 mg/ml. The symbol "*" indicates $p<0.05$ when cisplatin plus MIS was compared with cisplatin alone.

The percent survival of A431 cells was 100%, 56.5%, 38.7%, 34.3% and 10.8% respectively for cisplatin concentrations of 0, 0.078, 0.156, 0.312 and 0.624 µg/ml. With the addition of 7 nM DG-MIS, the percent survival became 39.3%, 32.2%, 23.1%, 20.4% and 5.4%, respectively, for the same concentrations of cisplatin. The percent survival of cisplatin alone and cisplatin plus MIS was significantly different at the cisplatin concentrations of 0.078 and 0.156 µg/ml (FIG. 6).

G. Multicellular Spheroid Assay

Figure 7A:
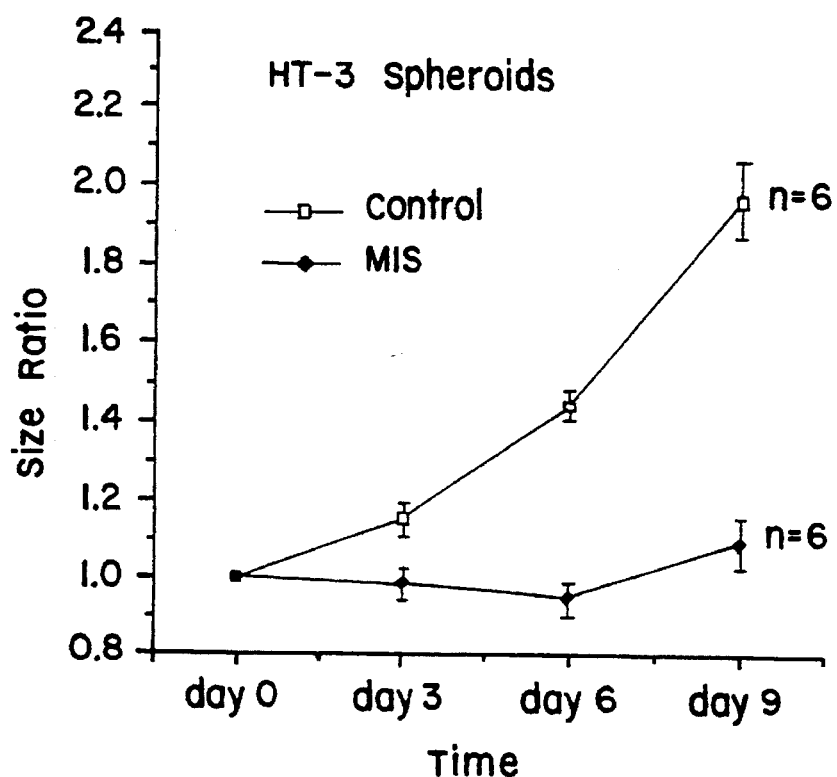
FIG. 7A shows the results of a spheroid assay. DG-MIS (7 nM) inhibited the growth of HT-3 spheroids when compared with control ($p<0.05$).
Figure 7B:
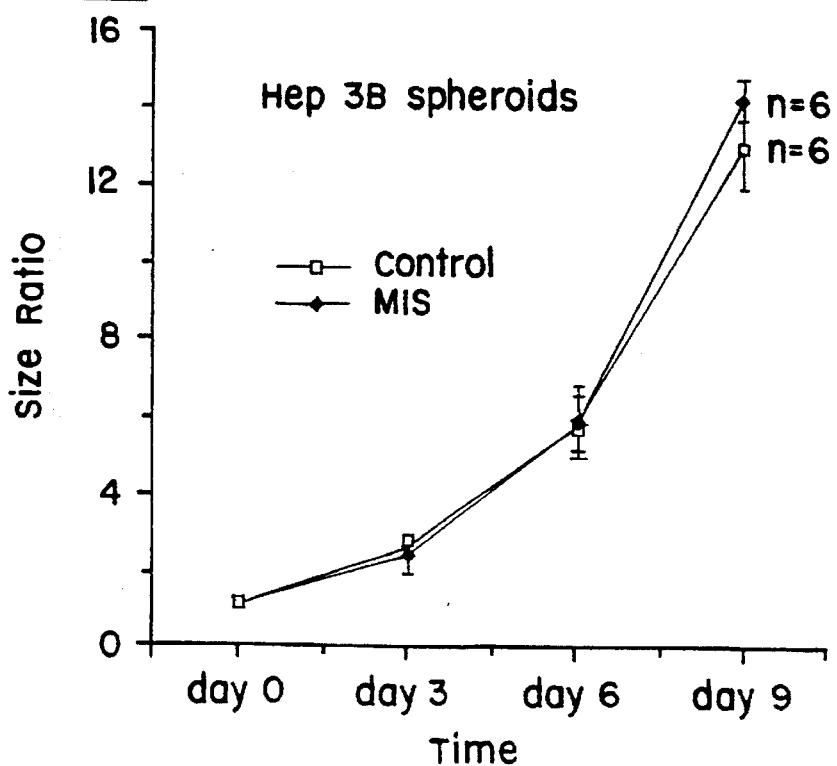
FIG. 7B shows the results of a spheroid assay. DG-MIS (7 nM) did not effect the growth of Hep 3B spheroids when compared with control ($p<0.05$).

The average size ratios of HT-3 spheroids in the control group (n=6) were 1.15±0.04, 1.44±0.02 and 151.96±0.11 at day 3, 6 and 9 respectively, while in the MIS group (n=6) they were 0.98±0.04, 0.94±0.04 and 1.08±0.06 (FIG. 7A). The average size ratios of Hep 3B spheroids in the control group (n=6) were 2.56±0.05, 5.64±0.53 and 13.07±1.09 respectively at day 3, 6 and 9, while in the MIS group (n=6), they were 2.36±0.25, 5.77±0.54 and 14.30±0.54. The growth of Hep 3B spheroids was faster and uninhibited by MIS (FIG. 7B).

H. Subrenal Capsule Assay

Figure 8A:
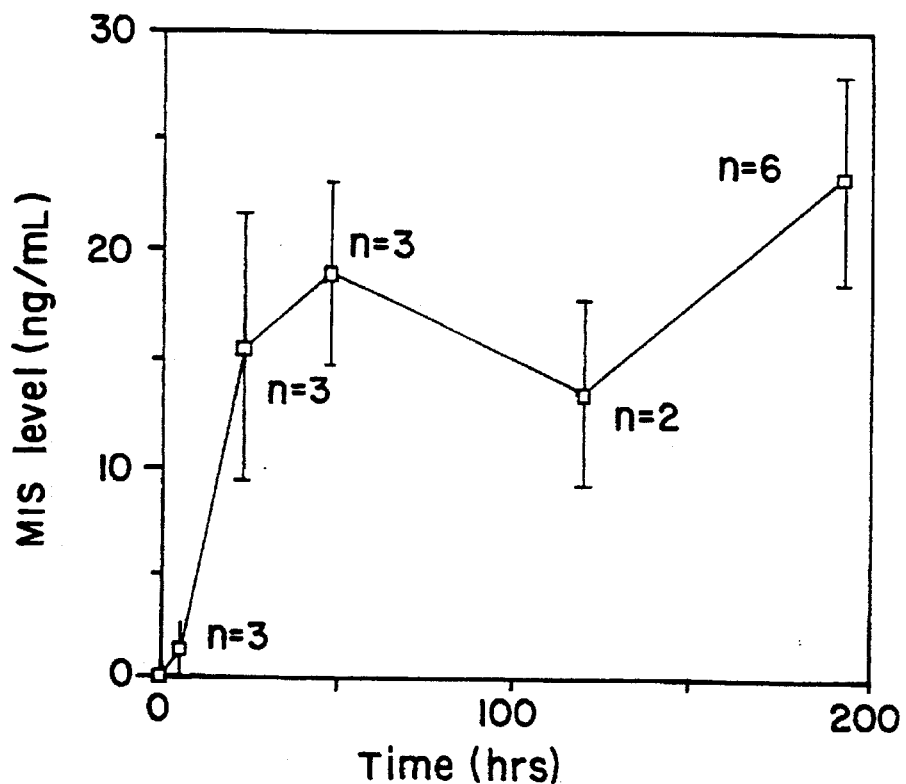
FIG. 8A shows MIS serum levels. Alzet pumps loaded with 33 μg MIS were implanted into CD-1 mice. A relatively constant level of MIS was achieved 24 hours after implantation.
Figure 8B:
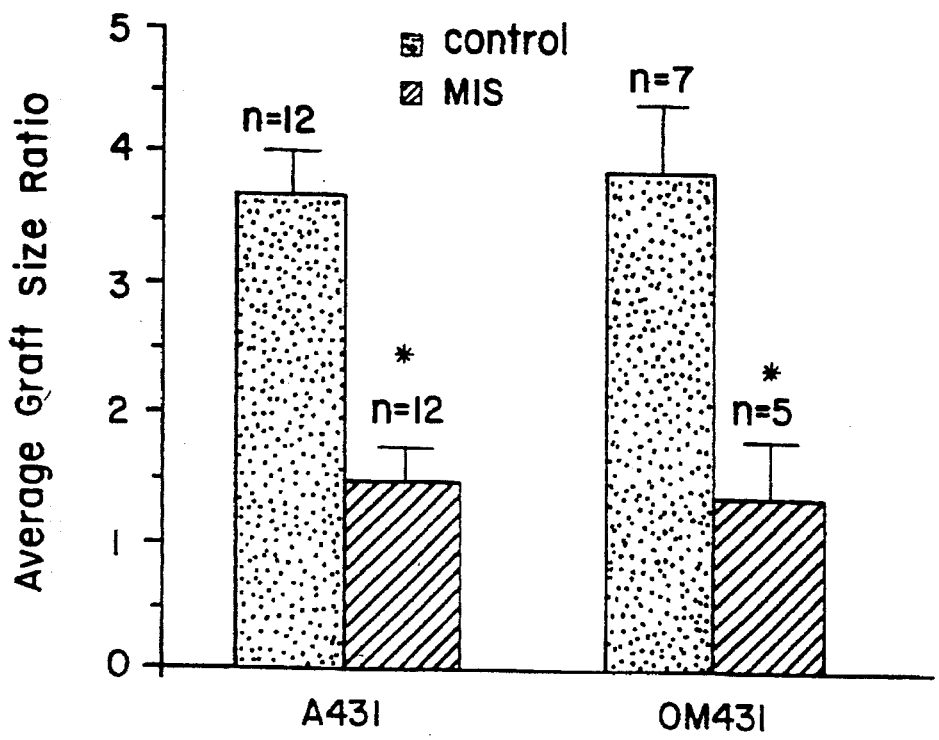
FIG. 8B shows inhibition of tumor growth in vivo by MIS. A431 and OM431 cells were implanted in the subrenal capsule space of CD-1 mice. The graft size ratios of both tumors were significantly inhibited in the MIS treated group. The symbol "*" indicates $p<0.05$ when compared with controls.

The MIS levels in mouse serum were relatively stable from 24 hours to the eighth day after the implantation of the MIS filled Alzet pumps (FIG. 8A). The average MIS level of 14 blood samples from day 2 to day 8 was 19.1±2.7 ng/ml (approximately 140 pM). The serum MIS levels of the control mice were undetectable. The graft size ratio of the implanted A431 tumor was 3.70±0.31 in the control group (n=12) vs 1.50±0.26 in the MIS group (n=12). The graft size ratio of the OM431 tumor was 3.93±0.49 in the control (n=7) vs 1.42±0.44 in the MIS group (n=5). The growth of the tumors in the MIS group was significantly lower than the control in both cell lines (p<0.05) (FIG. 8B).

III. Discussion

Recombinant human MIS (rhMIS) from the conditioned media of the amplified CHO cell line, purified by either serial ion exchange and dye affinity chromatography (DG-MIS) or immunoaffinity chromatography (IAP-MIS), was examined against various cell lines in a number of growth assays. Overall, the results of the liquid and semisolid assays were quite similar, with the exception of the HT-3 (cervical carcinoma) cell line which was inhibited by highly purified MIS in the semisolid assay but not in the liquid assay. The multicellular spheroid assay was used to recapitulate tumor microregions with cell-cell interactions and nutrient affected growth patterns. HT-3 cells formed satisfactory spheroids that were inhibited by MIS. No MIS effect was noted on the spheroid growth of Hep 3B (hepatocellular carcinoma). The availability of all three in vitro assays permits selection of optimal conditions for each tumor.

In evaluating MIS as an anticancer agent, it is important to consider its interaction with available chemotherapies. To evaluate this, MIS and cisplatin were tested alone and in various combinations. Since the inhibitory effects of MIS and cisplatin are additive, cisplatin doses could be lowered when given with MIS; therefore this biological modifier might function as an adjuvant in the multimodality treatment of selected human malignancies. The liquid colony inhibition and the spheroid assays can be used to test repeated doses of either MIS or MIS plus cytotoxic agents. However, asynchronous addition first of MIS, which best effects a proliferative cell population, then the cytotoxic agent, is preferable.

DG-MIS, although less purified, consistently showed inhibition of cell growth in vitro. The specificity of the MIS effect was demonstrated by blocking the inhibitory effect with an MIS monoclonal antibody.

Wallen et al. (Wallen et al., Cancer Res. 49:2005–2011 (1986)) reported only a minimal antiproliferative activity when an immunopurified MIS preparation was tested against a variety of established cell lines. In Example 1, the same poor response with IAP-MIS was observed before the salt elution step was added prior to elution with 1M acetic acid. In addition, the salt fraction eluted from the immunoaffinity column actually showed a growth stimulating effect in some cell lines. Electrophoresis of this salt fraction showed several bands in the region of 14–20 kDa, which are absent in the fraction subsequently eluted by 1M acetic acid. When the concentrated culture medium of untransfected wild-type CHO cells was subjected to the same purification process, the salt fraction, which also showed a stimulatory effect on A431 cells (FIGS. 1 and 2), revealed the presence of the same bands at 14–43 kDa, implying that these protein products of the untransfected CHO cells might act as growth stimulating factors to mask MIS effect. This finding is supported by the results shown in FIG. 5. When the dose responses to highly purified IAP-MIS and DG-MIS were compared, DG-MIS was shown to be 10-fold more potent than the more highly purified IAP-MIS.

The subrenal capsule assay was used to test the effect of MIS in vivo. By delivering MIS via an intraperitoneal constant infusion Alzet pump inserted at the time of tumor implantation, the growth of a vulvar epidermoid carcinoma cell line, A431, and an ocular melanoma line, OM431, were inhibited in vivo. In evaluating this assay, it is important that histology be documented for each different tumor, and the experiment completed before central necrosis occurs. Thus the assay was terminated on day 8, since longer duration led to variable cystic change. Such changes can vary the graft size ratio enough to make comparisons unreliable due to imbibition of fluid and cystic changes. By this careful analysis, the post implantation characteristics of each tumor cell line can be established and artifacts avoided. The in vivo effect in this subrenal assay is achieved at physiologic or picomolar concentrations. In vitro studies, on the other hand, require 50 to 500 fold higher levels, which may reflect failure of activation. No obvious toxicity to animals was observed.

EXAMPLE 2

I. Materials and Methods

A. Production and Purification of rhMIS

After cloning MIS cDNA and genomic DNA, dihydrofolate reductase deficient CHO cells were cotransfected with a linear construct of both the human MIS and the dihydrofolate reductase genes as in Example 1. The transfected CHO cells were amplified in Methotrexate and grown at 37° C. in alpha minimal essential medium without ribonucleosides and deoxyribonucleosides, supplemented with 10% bovine MIS-free female fetal calf serum (FCS). Immunoaffinity chromatography using an anti-human MIS monoclonal antibody was used to purify the rhMIS (90–95% pure) as in Example 1.

The biological activity of MIS was detected in vitro using the rat Müllerian duct regression organ culture assay as in Example 1. MIS concentrations were estimated using an enzyme-linked immunosorbent assay (ELISA) for MIS, and protein concentrations were measured as in Example 1.

B. Cell Lines

The human ocular melanoma cell lines, OM431, OM464, OM467, and OM482, were established in 1984 and kept in liquid nitrogen until early passage ampules were thawed for this study. They were maintained in the alpha modification of Eagle's medium supplemented with ribonucleosides and deoxyribonucleosides (α-MEM+) to which was added 10% female FCS and 1 gm/l L-glutamine. Before study, cells were serially subcultured, then trypsinized at 70–80% confluency. This proliferating cell population was then centrifuged at 1500 RPM for 5 minutes and resuspended with 10% female FCS supplemented medium. Cells were counted in a hemocytometer.

C. Semisolid Medium (Double Layer) Colony Inhibition Assay

The effect of rhMIS was tested using the conventional double layer agarose colony inhibition assay as in Example 1. The underlayer of the 35 mm culture dishes contained 1 ml of 0.6% agarose (Sigma, St. Louis, Mo.) in 10% female FCS supplemented α-MEM+. The overlayer consisted of 0.3% agarose in 10% female FCS supplemented a-MEM+, the cells to be tested (50,000 cells/ml for OM431; 25,000 cells/ml for OM464, OM467 and OM482), epidermal growth factor (EGF) 10 ng/ml (Sigma, St. Louis, Mo.) and either rhMIS or vehicle buffer as a negative control. The dishes were incubated in humid air with 5% $CO_2$ at 37° C. for 10–21 days. Colonies with more than 30 cells were counted with an inverted microscope (Nikon). The results are expressed as percent survival relative to a control group (number of colonies in the test group x 100/number of colonies in the control group).

D. Liquid Medium Colony Inhibition Assay

Single cell suspensions of OM431 were placed and grown in 24-well culture plates (Falcon, Oxnard, Calif., #3047) at a concentration of 8250 cells per well in 0.5 ml media (α-MEM+ with 10% female FCS and 50 ng/ml EGF) as in Example 1. After cell attachment, only those with good single cell dispersion without clumping were used for further study. Agents to be tested were added (50 microliters per well) and were tested in triplicate. The cells were incubated in humid air with 5% $CO_2$ at 37° C. Colonies which formed in 5–7 days were stained with Giemsa solution and those with more than 30 cells were counted by eye with an inverted microscope or the counting was automated using a computer based image analyzer.

E. Dose Dependent Inhibition of OM431 Cells by MIS

After dilution in vehicle buffer, MIS was tested in concentrations of 0.98, 9.8, 25.2, 50.4, 75.6, and 100.8 nM. The results were expressed as percent survival relative to the vehicle buffer control.

F. Multicellular Tumor Spheroids Assay

Multicellular tumor spheroids of OM467 and OM482 cells were produced as described in Example 1. In brief, $10^5$ cells of OM467 in 1 ml of 10% female FCS supplemented α-MEM+, were plated on top of 1.5 ml of 1% agarose in a 35×10 culture dish after thorough washing to remove residual trypsin, and incubated in humid air with 5% $CO_2$ at 37° C. for 2–5 days when spheroids usually formed. 0.5 ml of 1% agarose was then added to each well of a 24-well culture plate (Falcon, Oxnard, Calif., #3047). Individual spheroids of similar size (approximately 250 mm diameter) were selected under a dissecting microscope and transferred by micropipette each to a well containing 0.5 ml of 10% female FCS supplemented α-MEM+ on top of the agarose layer. The sizes of the spheroids on day 0 were measured by the longest diameter (L) and the diameter perpendicular to the longest one (W) and volume then expressed as (L×W× W). Six spheroid containing wells were treated either by rhMIS or vehicle buffer. Volumes were measured at regular intervals. The size ratio of each spheroid at different intervals was obtained by comparing it to the size of the same spheroid at day 0. The average size ratio of each group was plotted vs. time in a growth curve and compared to the other groups.

G. Subrenal Capsule Assay

Following the method described in Example 1, OM431 cells grew to graft size of 3.68±0.56; OM482 to 1.97±0.67; OM467 to 1.34±0.5; and OM464<1. Thereafter, $10^7$ OM431 cells were centrifuged at 1500 RPM for 5 minutes to form a pellet. 20 ml of fibrinogen (Sigma, St. Louis, Mo., 20 mg/ml dissolved in PBS pH 7.4) was added to the pellet, followed by 10 ml of thrombin (Sigma, St. Louis, Mo., 20 unit/ml dissolved in double-strength Dulbecco's modified essential medium). The mixture was incubated at 37° C. for 15 min. The cell clot thus formed was cut into approximately 50 fragments (1 $mm^3$, each containing approximately $10^5$ cells) in preparation for implantation.

MIS was delivered by an Alzet mini-osmotic pump (#2001, Alza, Palo Alto, Calif.) placed in the peritoneal cavity at the time of tumor implantation. These pumps have a fill volume of approximately 210 µl and release their contents at a rate of approximately 1 µl/hr for eight days of delivery time. The pumps were either filled with rhMIS or with vehicle buffer.

Virus and pathogen free female CD-1 mice (10 weeks old, average weight 35 g, Charles River Breeding Laboratory, Wilmington, Mass.) were given whole body irradiation of 640 rads by a Mark-I cesium-137 irradiator 16–24 hours before the experiment as in Example 1. Nude mice (8 weeks old, average weight 24 g, Edwin L. Steele Laboratory, Massachusetts General Hospital, Boston, Mass.) were also used. After inducing anesthesia with an intraperitoneal injection of 0.3 ml of 10% Pentobarbital (Abbott Laboratory, North Chicago, Ill.), an incision was made in the left flank of the mouse and the left kidney exteriorized. A subcapsular space was developed using a 19-gauge needle trocar. A cell clot was introduced into the space with a segment of 5-0 Nylon suture (approximately 1 mm in length), which was used both to calibrate ocular micrometer measurements and to localize the tumor. Twelve CD-1 mice and twenty nude mice were implanted with OM431 cell clots. The longest diameter (L1) of the implant, the diameter perpendicular to the longest diameter (W1), and the length of the suture were measured with the ocular micrometer of a dissecting microscope. The animals were either treated by rhMIS or vehicle buffer delivered by the Alzet pumps placed in the peritoneal cavity. The animals were sacrificed on the eighth day. Blood samples were obtained on the eighth day from the nude mice and serum MIS levels were measured by ELISA. The longest diameter (L2) of the tumor, the diameter perpendicular to the longest diameter (W2), and the length of the suture were measured blindly by two independent investigators. After calibration of the measurements, the graft size ratio was represented by (L2×W2×W2)/(L1×W1×W1). Histologic sections of the kidneys were also obtained and examined. Tumors with cystic change were excluded.

H. Statistical Analysis

The results of the liquid medium, semisolid medium colony inhibition, multicellular spheroid and subrenal capsule assays were tested by the Student t-test. $P<0.05$ was considered as statistically significant.

II. Results

Figure 9:
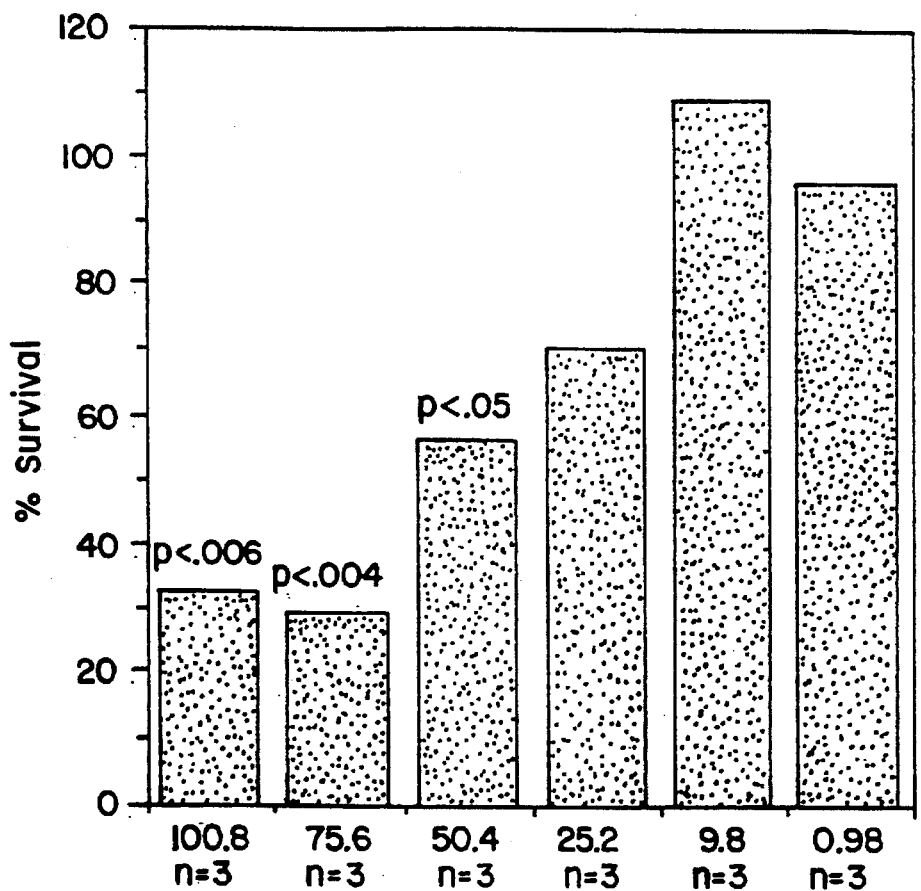
FIG. 9 shows dose dependent inhibition of OM431 colony formation by MIS in a liquid colony inhibition assay. The percent survival was 33%, 29.5%, 56.6%, 71%, 109.8%, and 96.8%, respectively, for MIS concentrations of 100.8, 75.6, 50.4, 25.2, 9.8, and 0.98 nM. Significant inhibitions were seen with MIS concentrations of 50.4 ($p<0.05$), 75.6 ($p<0.004$), and 100.8 ($p<0.006$) nM MIS.

A. Dose Dependent Inhibition of OM431 Colony Formation by MIS in the Liquid Colony Inhibition Assay Only OM431 cells achieved adequate growth with its ligand colony inhibition assay. The percent survival was 33%, 29.5%, 56.6%, 71%, 109.8%, and 96.8% respectively for MIS concentrations of 100.8, 75.6, 50.4, 25.2, 9.8, and 0.98 nM. Significant inhibitions were seen with MIS concentrations of 50.4 ($p<0.05$), 75.6 ($p<0.004$), and 100.8 ($p<0.006$) nM MIS (FIG. 9).

B. Semisolid Medium (Double Layer) Colony Inhibition Assay

Figure 10:
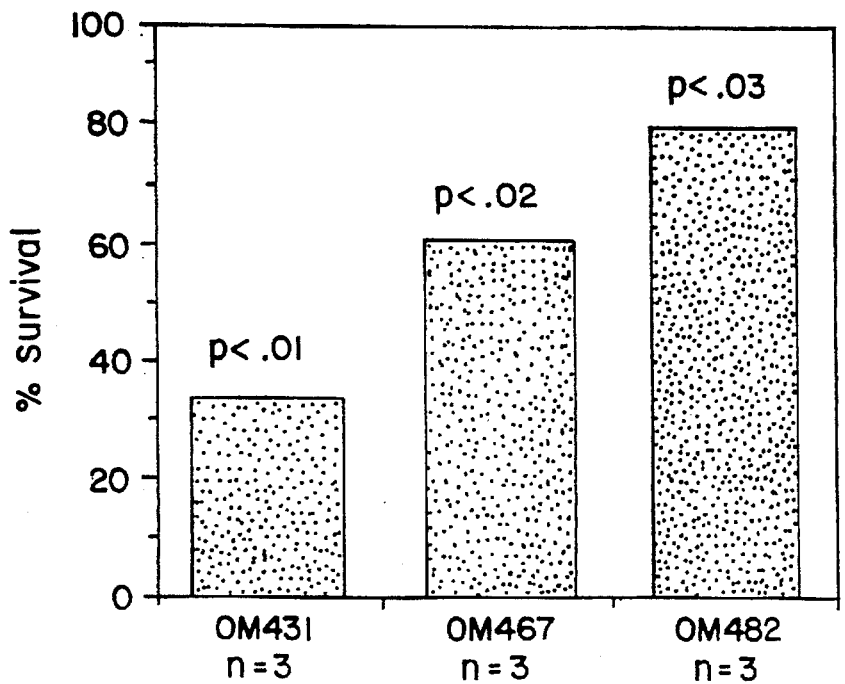
FIG. 10 shows the results of a semisolid medium (double layer) colony inhibition assay. All cell lines were significantly inhibited by rhMIS. The percent survival of the various cell lines was 34% for OM431 (in 30 nM MIS) ($p<0.01$), 61% for OM467 (in 150 nM MIS) ($p<0.02$), and 80% for OM482 (in 90 nM MIS) ($p<0.03$).

All cell lines, except OM434 which failed to grow colonies, were significantly inhibited by rhMIS. The percent survival of the various cell lines was 34% for OM431 (in 30 nM MIS) ($p<0.01$), 61% for OM467 (in 150 nM MIS) ($p<0.02$), and 80% for OM482 (in 90 nM MIS) ($p<0.03$) (FIG. 10).

C. Multicellular Spheroid Assay

Figure 11A:
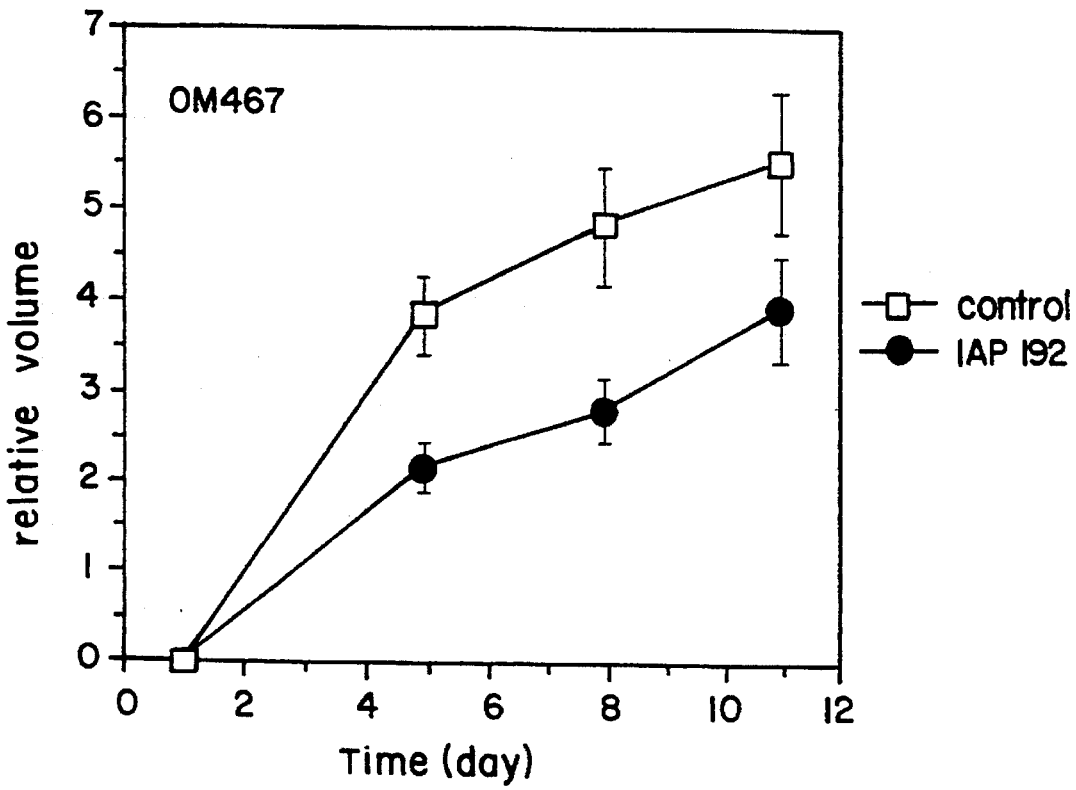
FIG. 11A shows the results of a multicellular spheroid assay of OM467 cells. The average graft size ratios of OM467 spheroids in the control group (n=6) were 3.85±0.43, 4.85±0.64 and 5.52±0.78 at day 5, 8 and 11, respectively. The average graft size ratios in the MIS group (n=6) were 2.17±0.26, 2.79±0.33 and 3.91±0.59, respectively. This difference was significant ($p<0.02$).
Figure 11B:
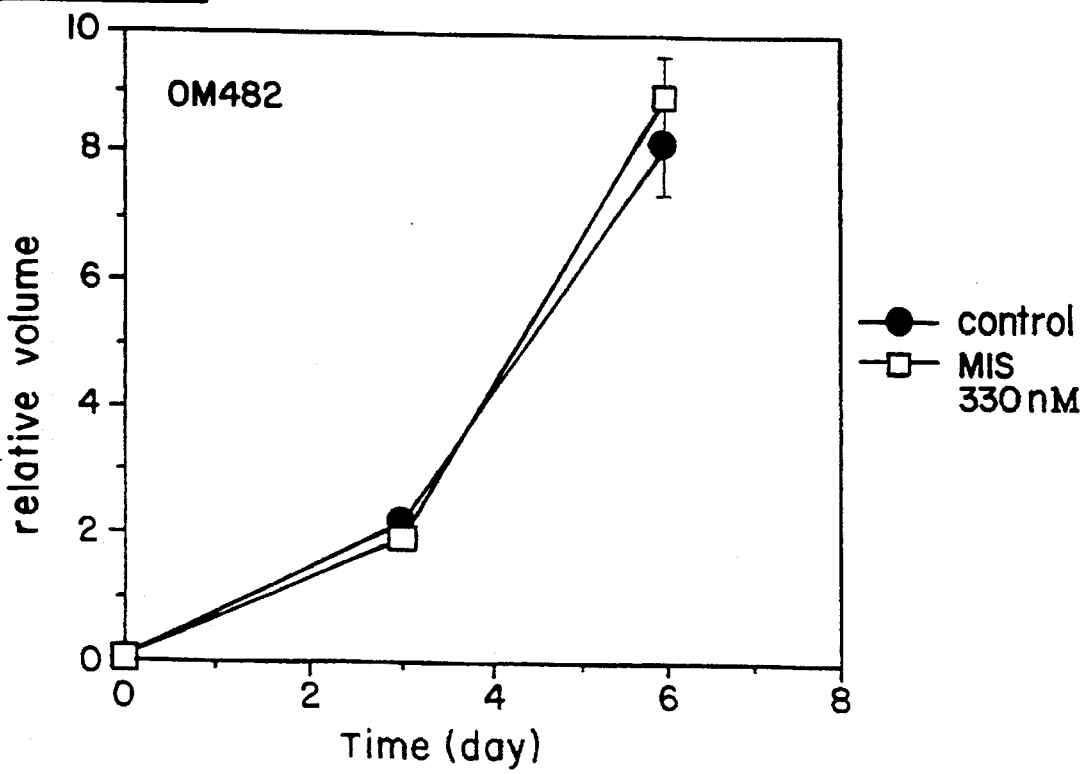
FIG. 11B shows the results of a multicellular spheroid assay of OM482 cells. The average graft size ratios of OM482 spheroids in the control group (n=10) were 2.18±0.17 and 8.22±0.81, respectively, at day 3 and 6. The average graft size ratios in the MIS group (n=10) were 1.93±0.14 and 9.0±0.67, respectively.

The average size ratios of OM 467 spheroids in the control group (n=6) were 3.85±0.43, 4.85±0.64 and 5.52±0.78 at day 5, 8 and 11, respectively, while in the MIS group (n=6) they were 2.17±0.26, 2.79±0.33 and 3.91±0.59. This difference was significant ($p<0.02$). The average size ratio of OM482 spheroids in the control group (n=10) were 2.18±0.17 and 8.22±0.81 respectively at day 3 and 6, while in the MIS group (n=10), they were 1.93±0.14 and 9.0±0.67 (FIGS. 11A & B). OM431 and OM464 failed to grow as spheroids.

D. Subrenal Capsule Assay

Figure 12A:
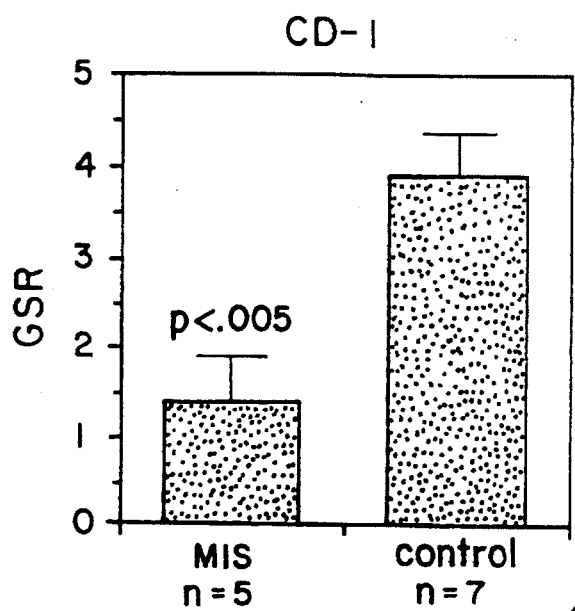
FIG. 12A shows the results of a subrenal capsule assay of CD-1 irradiated mice. The graft size ratio of the OM431 tumor was 3.93±0.49 in the control (n=7) compared to 1.42±0.44 in the MIS group (n=5). Each MIS treated mouse received 48.6 micrograms of MIS over the eight day assay. The growth of the tumors in each MIS group was significantly lower than the control ($p<0.005$).
Figure 12B:
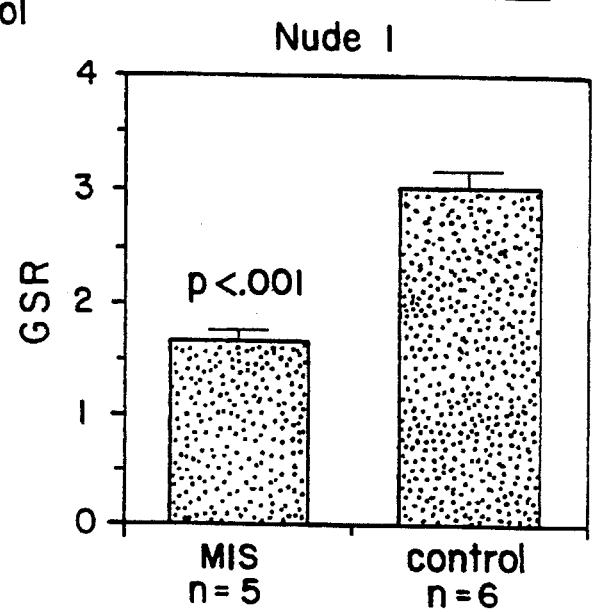
FIG. 12B shows the results of a subrenal capsule assay using nude mice. The graft size ratios of the OM431 tumors were significantly greater for the controls (3.02±0.17) compared to the MIS group (1.68±0.09). The MIS treated group received 44.7 micrograms MIS over eight days. The average MIS serum levels of the MIS treated mice on the eighth day of the nude mouse assays were 749 pM. The measured controls had MIS levels of less than 10 pM. The growth of the tumors in each MIS group was significantly lower than the control ($p<0.001$).
Figure 12C:
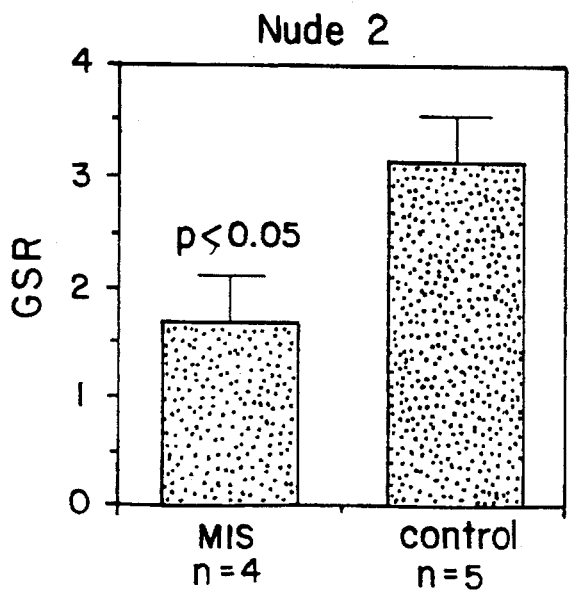
FIG. 12C shows the results of a subrenal capsule assay using nude mice. The graft size ratios of the OM431 tumors were significantly greater for the controls (3.14±0.40) compared to the MIS group (1.69±0.43). The MIS treated group received 130 micrograms MIS over eight days. The average MIS serum levels of the MIS treated mice on the eighth day of the nude mouse assay were 570 pM. The measured controls had MIS levels of less than 10 pM. The growth of the tumors in each MIS group was significantly lower than the control ($p<0.05$).

In the CD-1 irradiated mice, the graft size ratio of the OM431 tumor was 3.93±0.49 in the control (n=7) vs 1.42±0.44 ($p<0.005$) in the MIS group (n=5). Each MIS treated mouse received 48.6 micrograms of MIS over the eight day assay. In two assays using nude mice, with eleven controls and nine MIS treated mice, the graft size ratios of the OM431 tumors were significantly greater, 3.02±0.17 and 3.14±0.40, respectively, for the controls, vs 1.68±0.09 ($p<0.001$) and 1.69±0.43 ($p<0.005$) for the MIS group. In the first nude mouse assay, the MIS treated group received 44.7 micrograms MIS over eight days while in the second nude mouse assay, the MIS group received 130 micrograms. The average MIS serum levels of the MIS treated mice on the eighth day of the nude mouse assays were 749 and 570 pM respectively. The measured controls had MIS levels of less than 10 pM. The growth of the tumors in each MIS group was significantly lower than the control in all three assays ($p<0.05$) (FIGS. 12A–C).

III. Discussion

In Example 2, the effect of recombinant human MIS on three human ocular melanoma cell lines using three different in vitro clonogenic assays were examined. The reliable and reproducible double-layer inhibition assay was used with each cell line. Despite its rather lengthy incubation time (10–21 days), all the cell lines grew well in this assay. OM482, OM431 and OM467 were significantly inhibited. The liquid colony inhibition assay was used with the OM431 cell line. OM467 and OM482 failed to grow discrete colonies in this assay. When effective, as with OM431, this assay is rapid (5–7 days) and uses little sample. OM431 showed a clear dose response with inhibition of colony formation with rhMIS concentrations above 25 nM. The percent survival of OM431 correlated well between the two assays. The multicellular spheroid assay was used to recapitulate tumor microregions with cell-cell interactions and nutrient affected growth patterns. OM467 and 482 cell lines formed satisfactory spheroids. OM467 showed significant inhibition while the growth of OM482 was unaffected. OM431 failed to grow spheroids. The availability of all three in vitro assays permits selection of optimal conditions for each tumor.

The subrenal capsule assay was used to test the effect of MIS in vivo against OM431, since this line grew large enough to permit comparisons. By delivering MIS via an intraperitoneal constant infusion Alzet pump inserted at the time of tumor implantation, the growth of OM431 was inhibited in vivo. It is important in evaluating this assay that histology be documented for each different tumor, and the experiment completed while the tumors are still solid and before a lymphocytic infiltrate and/or central necrosis occurs. Thus, the assay was terminated on day 8 in the irradiated CD-1 mice since a longer duration of incubation led to variable histologic changes which can vary the graft size ratio enough to make comparisons unreliable due to imbibition of short lived fluid, inflammatory cell infiltration and cystic changes. To eliminate the potential pitfalls of radiation induced immunosuppression, nude mice were also used and similar tumor growth inhibition was seen. The same period of time was used when tumors were implanted in the nude mice. No obvious toxicity to animals was observed during the short course of this study. The in vivo effect in this subrenal assay is achieved at picomolar concentrations. In vitro studies, on the other hand, require 10 to 100 fold higher levels, suggesting a failure of cleavage and activation.

EXAMPLE 3

I. Materials and Methods

A. rhMIS purification rhMIS purification by immunoaffinity chromatography of conditioned medium of Chinese hamster ovary cells transfected with the human MIS gene has been described (Pepinsky et al., *J. Biol. Chem.* 263:18961–4 (1988)) and recently modified (Ragin, R. C., et al., submitted). Briefly, media were collected every 3–4 days from bioreactor cultures (Epstein et al., *In Vitro Cell. and Devel. Biol* 25:213–6

(1989)) and stored at −20° C. until use. A 5-ml immunoaffinity column was constructed using approximately 50 mg protein-A-Sepharose (Sigma Chemical Co., St. Louis, Mo.) purified mouse monoclonal antihuman rhMIS antibody (Hudson et al., *J. Clin. Endocrinol. Metab.* 70: 16–22 (1990)) covalently attached to Affigel-10 agarose resin (Bio-Rad Laboratories, Richmond, Calif.). The column was equilibrated with 100 ml 20 mM HEPES, pH 7.4 and 200 ml concentrated medium loaded after filtration through Whatman No. 4 paper (Clifton, N.J.) at 1 column vol/h at 4° C. After loading, the column was washed with 20 mM HEPES, pH 7.4, until the absorbance at 280 nm returned to baseline (60–100 ml).

rhMIS was eluted using 1M acetic acid in 20 mM HEPES, pH 3.0, after a 1-column vol. preelution wash containing 0.5 m NaCl, 1 mM EDTA, 0.001% Nonidet P-40 (Sigma Chemical Co.), and 20 mM HEPES, pH 7.4. The majority of the rhMIS eluted in a single 2-ml fraction, which was immediately neutralized with NaOH to a pH between 7.0–7.4. The acid-eluted immunoaffinity-purified (IAP) fractions were dialyzed overnight against 0.02M HEPES and 0.001% Nonidet P-40, pH 7.4. The resulting samples were analyzed for total protein by the Bradford method (Bradford, M. M., *Anal. Biochem.* 72:248–254 (1976)) and for rhMIS concentrations by an enzyme-linked immunosorbant assay (Hudson et al., *J. Clin. Endocrinol. Metab.* 70:16–22 (1990)). They were further examined by polyacrylamide gel electrophoresis (Weber et al., *J. Biol. Chem.* 244:4406–4412 (1969)), and activity was determined in an in vitro Müllerian duct regression bioassay and an antiproliferative assay using human A431 vulvar carcinoma cells (see blow).

B. Purification of the carboxy-terminus of rhMIS

IAP rhMIS (1.1–1.5 mg in 2.5 ml 20 mM HEPES buffer, pH 7.4) was incubated with plasmin (EC 3.4.21.7 Sigma Chemical Co.) at a ratio of 20–25:1 rhMIS to plasmin (wt/wt) for 2 hours at room temperature, as previously described (Pepinsky et al., *J. Biol. Chem.* 263:18961–4 (1988)). The preparation was then placed onto a 21.5×16-cm P-100 polyacrylamide column (Bio-Rad Laboratories, Richmond, Calif.) equilibrated at 4° C. with 1.0M acetic acid in 20 mM HEPES at pH 3.0. Protein was eluted in 0.54 ml fractions at a flow rate of approximately 2.0 ml/hour. Ten microliter aliquots were analyzed for protein by the Bradford method (Bradford, M. M., *Anal. Biochem.* 72:248–254 (1976)). Two peaks of protein, termed A and B, elute from this column. These peaks were pooled separately, frozen in liquid nitrogen, and concentrated by lyophilization in a Savant Speed-Vac apparatus (Hicksville, N.Y.). The resulting pools were dissolved in either 20 mM HEPES, pH 7.4 or 0.3M sodium phosphate, pH 7.4, so that a final protein concentration of 1 mg/ml was achieved. Elution buffer in volumes similar to those of the pools was also lyophilized and dissolved in buffer, as described above, to serve as controls for the rhMIS bioassays.

C. rhMIS bioassay

The standard organ culture bioassay for MIS was performed as previously described (Donahoe et al., *Biol. Reprod.* 16:238–243 (1977); MacLaughlin et al., *Methods in Enzymology* 198:358–369 (1991)). Briefly, 141 2-day-old female fetal rat urogenital ridges were placed on agar-coated stainless steel grids above fortified CMRL 1066 (Gibco/Bethesda Research Laboratories, Gaithersburg, Md.) medium containing female fetal, and therefore MIS-free, calf serum (Necklaws et al., *Endocrinology* 118:791–796 (1986) and testosterone at $10^{-9}$M to enhance the Wolffian duct for direct comparison of the Müllerian duct in each tissue section. rhMIS protein samples of 0.5–8.0 μg each or buffer controls were added in serum containing CMRL medium after sterile filtration in that solution through a 0.22 μm Millex GV membrane.

Control studies using carboxy-terminal rhMIS radiolabeled with $^{125}$I by a standard technique (Hunter, R., *Proc. Soc. Exp. Biol. Med.* 133:989–992 (1970)) demonstrated no loss of the protein to this filter. After incubation for three days in humidified 5% $CO_2$ at 37° C., the specimens were fixed in 15% formalin and embedded in paraffin, and 8-μm sections of the cephalic end were stained with hematoxylin and eosin. The sections were then ranked from grade 0 (no regression) to grade 5 (complete regression) by two experienced observers. One unit of activity is defined as that causing a one grade increase in Müllerian duct regression. Data were compared by Student's t test for significant differences among groups.

D. Antiproliferation assay

The A431 cell line, derived from a squamous cell carcinoma of the vulva was maintained in Dulbecco's Modified Eagle's Medium (DMEM) containing 10% MIS-free female calf serum (FCS). The cells, which have an approximately 22-hour doubling time, were grown to confluency and maintained for an additional 24 hours. A431 cell cultures passaged in this manner are slowed in their transition through the cell cycle and are predominantly found in the $G_1$ phase, as confirmed by flow cytometric analysis. The cells were trypsinized, washed with DMEM in 10% FCS, counted, and diluted to a final seeding concentration of approximately 200,000 cells/35-mm culture dish in a total volume of 1.5 ml medium. This medium contains 15 mM HEPES to buffer against the acidification that occurs with the addition of the carboxy-terminus. Various concentrations of carboxy-terminal rhMIS, holo rhMIS, or appropriate buffer controls were added in duplicate, once at the time of plating or three times, at plating and 24 and 48 hours postplating. Controls in DMEM and 10% FCS were examined in triplicate. The cultures were incubated at 37° C. in a 95% $O_2$—5% $CO_2$ atmosphere. Microscopic inspection and control cell counts were performed every 24 hours for three days. All counts were performed using a Coulter counter (Model $Z_f$, Hialeah, Fla.), and data are presented as the percentage of cells in the buffer or rhMIS carboxy-terminus-treated groups compared to that in the untreated controls ±1 sd. Significant differences among the treatment groups were analyzed by Student's t test.

E. rhMIS carboxy-terminus-specific antibody preparation

Epitope-specific rabbit polyclonal antibodies were raised to a region of the rhMIS molecule carboxy-terminal to the monobasic consensus cleavage site at position 427 and recently characterized (Pepinsky et al., *J. Biol. Chem.* 263:18961–4 (1988); Ragin, et al., submitted). Synthetic peptide corresponding to residues 470–482 (WPQSDRNPRYGNH) (SEQ. ID. NO.5) rhMIS, constructed from the amino acid sequence of human rhMIS (Cate et al., *Cell* 45:685–698 (1986)) by fluorenylmethyl chloroformate carboxyl chemistry, was used as antigen. Before use as an antigen, the synthetic peptide was subjected to compositional and primary sequence analyses to confirm its structure. This sequence was chosen for its conserved homology among human, bovine, and rat MIS, its difference from other members of the supergene family, and its antigenicity and surface probability, as predicted by the sequence analysis software package of the Genetics Computer Group (University of Wisconsin, version 5), using the criteria outlined by Chou and Fasman (Chou et al., *Adv. Enzymol. Relat. Areas. Mol. Biol.* 47:45–148 (1978)) and Wolfe et al., *Comput. Appl. Biosci.* 4:187–191 (1988)).

Following an institutional Review Board-approved protocol, New Zealand White rabbits were injected into the exposed popliteal lymph nodes with complete Fruend's adjuvant containing 25–50 µg of the peptide conjugated 1:1 with keyhole limpet hemocyanin (Calbiochem, San Diego, Calif.) by 0.25% gluteraldehyde cross-linking. Animals were boosted by sc injection on the back, 4–6 weeks later, with 20–30 µg unconjugated peptide in incomplete Fruend's adjuvant and bled one month later through an ear vein; the serum was stored at –20° C. Polyclonal antiserum was purified by 50% ammonium sulfate precipitation, followed by Protein-A-Sepharose chromatography.

F. Electrophoresis

Polyacrylamide gel electrophoresis (Weber et al., *J. Biol. Chem.* 244:4406–4412 (1969); Laemmli, U.K., *Nature* 227:680–685 (1970)) was carried out using 15% homogeneous minigels (1.5×80×75 mm) overlaid with a 5% polyacrylamide stacking gel, and 2- to 5-µg protein samples were run at 110-V and 30-mamp constant current at room temperature. Proteins in the gels were stained with 0.1% Coomassie brilliant blue R250 (Sigma Chemical Co.) in 50% methanol-10% acetic acid for 1 hour before destaining in 50% methanol—10% acetic acid. As appropriate, samples were reduced using 0.75M 2-mercaptoethanol with heating to boiling for 10 minutes before the electrophoresis run. Prestained low molecular weight standards were obtained from Bio-Rad.

For Western analysis (Towbin et al., *Proc. Natl. Acad. Sci. U.S.A.* 76:4350–4354 (1979), polyacrylamide gels were incubated in transfer buffer (25 mM Tris and 0.2M glycine in methanol) before electrophoretic transfer to Immobilon-PVDF (Milligen Corp., Burlington, Mass.) sheets for 18 hours at 150-mamp constant current at 4° C. Unreacted protein-binding sites on the membranes were then blocked by incubation with 3% (wt/vol) BSA for 30 minutes at room temperature with shaking. Thereafter, the blots were incubated with a 1:500-fold dilution of rabbit polyclonal anti-rhMIS carboxy-terminal peptide antiserum for 2 hours and washed with 0.05M Tris-Cl and 0.15M NaCl before the addition of a 1:1000 dilution of goat anti-rabbit horseradish peroxidase conjugate (Bio-Rad). Antibody complexes were visualized by the addition of Bio-Rad color reagent (4-chloro-1-naphthol) for 30 minutes, before quenching the reaction with water.

II. Results

Figure 13:
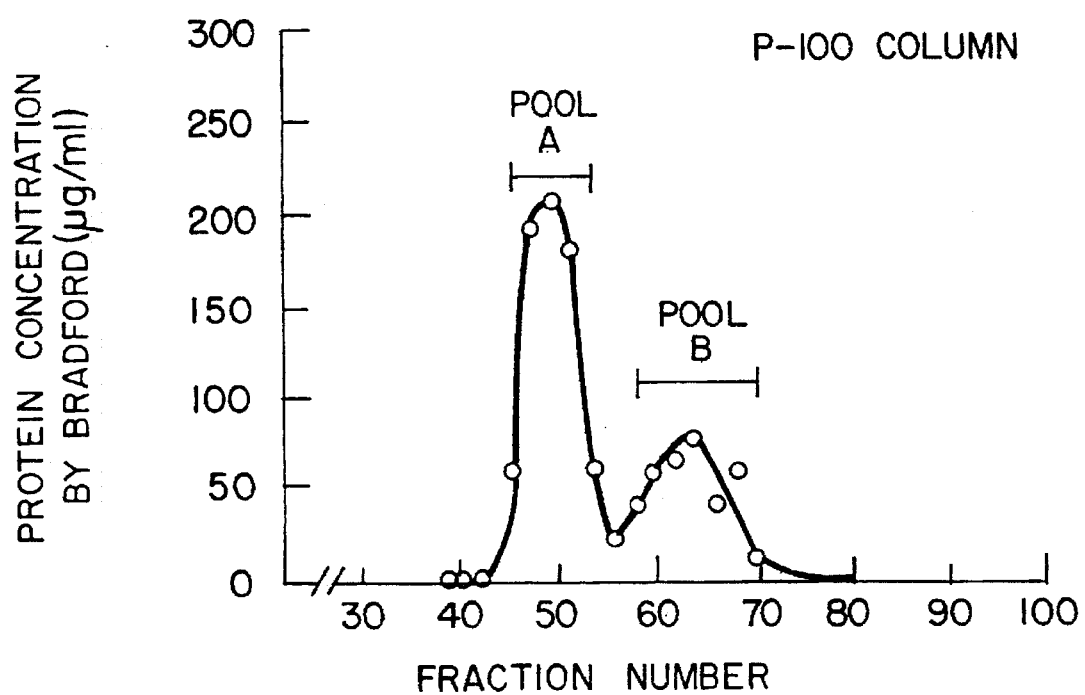
FIG. 13. A representative P-100 column chromatogram of a plasmin-cleaved rhMIS preparation. The protein content of each 0.54-ml fraction is given on the ordinate, and the fraction number on the abscissa. The positions of the pools for amino- and carboxy-terminal fragments of rhMIS are indicated by the brackets.
Figure 14:
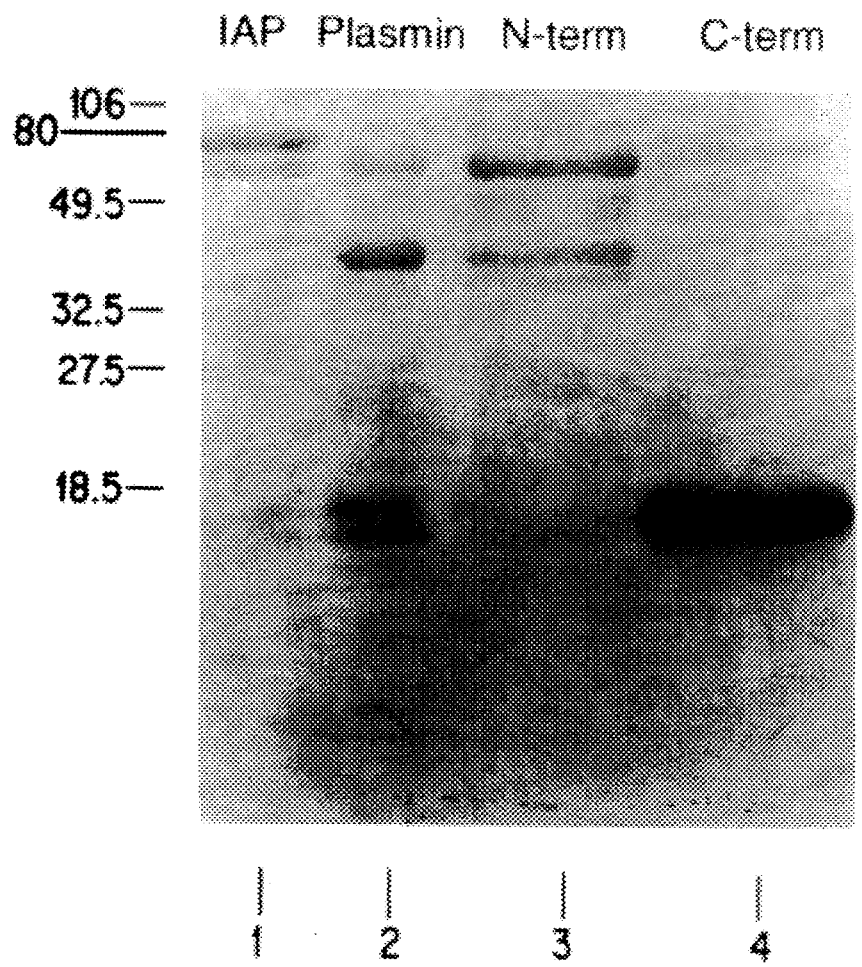
FIG. 14. This figure shows the electrophoretic separation of rhMIS under reducing conditions before (lane 1, IAP) and after treatment with plasmin (lane 2, Plasmin). Treatment with plasmin results in the characteristic depletion of 70-kDa rhMIS monomer and the appearance of 55-, 34-, and 12.5- to 14-kDa bands. In addition, the protein fragments separated by the P-100 column are shown. Pool A (lane 3, N-term) contains proteins of 34–55 kDa, while pool B (lane 4, C-term) reveals the presence of essentially only bands of 12.5–14 kDa. The positions of the prestained mol wt markers are given at the left.
Figure 15:
FIG. 15. A Western analysis of the intact rhMIS starting material (lane 1, IAP) and the pool A (lane 2, N-term) and pool B (lane 3, C-term) proteins. In this gel, run under reducing conditions, the polyclonal carboxy-terminal specific antibody essentially only reacts with the 12.5- to 14-kDa bands in pool B and the intact monomer of rhMIS (IAP), but not the proteins in pool A, the amino-terminal domain.

A representative P-100 column elution profile of plasmin-cleaved rhMIS is shown in FIG. 13. Two protein peaks, termed A and B, are observed. The later eluting species (pool B) consists chiefly of a single band running just below the 18.5-kDa molecular weight standard in the Coomassie blue-stained polyacrylamide gel of pooled A (N-term) or B (C-term) fractions analyzed after disulfide bond reduction (FIG. 14). The electrophoretic migration patterns generated for intact rhMIS (IAP) and rhMIS incubated with plasmin (Plasmin) are given for comparison. Note that a small degree of cleavage of rhMIS is detected in the IAP sample and that plasmin treatment completely depletes the 70-kDa intact monomer and generates the corresponding lower molecular weight species. The pool B protein, which migrates as a 25-kDa band under nonreducting conditions (data not shown), is recognized by the anti-rhMIS-carboxy-terminal antibody on Western analysis of the reduced proteins (FIG. 15). As expected, the peptide antibody binds to the intact rhMIS 70-kDa monomer (IAP, lane 1) and the low molecular weight pool B fragments (C-term, lane 3), but not to the 34- to 55-kDa molecular weight species that elute in fraction A from the P-100 column (N-term, lane 2). These results indicate that the pool B 12- to 14-kDa species is the carboxy-terminal rhMIS. The bioactivity of these isolated pools was tested in the standard MIS 14.5-day-old fetal rat urogenital ridge bioassay. In 10 trials with 10 different preparations, the carboxy-terminal rhMIS domain exhibited a high degree of Müllerian duct regression activity, as did the intact molecules, although the fragment was approximately 5-fold less active on a molar basis (Table 1).

TABLE 1

| Mean biological activity in the Müllerian duct regression assay | | | |
|---|---|---|---|
| | 5 µg | 1 µg | 0.5 µg |
| Intact rhMIS | 4.5 ± 0.2 (9) | 2.6 ± 0.7 (4) | 0.8 ± 0.3 (2) |
| C-Terminus | 3.5 ± 0.4 (10) | 1.9 ± 0.5 (9) | 1.5 ± 0.6 (4) |
| N-Terminus | 0.8 ± 0.4 (8) | 0.2 ± 0.1 (5) | 0.0 ± 0.0 (2) |

Data are the mean ± SEM; the number of determinations is given in parenthesis

At every dose tested, holo and carboxy-terminal rhMIS were not significantly different from one another, but both were different from the amino-terminus at the highest dose (P<0.05). Amino-terminal fragments had little or no effect at every dose tested.

To examine the antiproliferative activity of rhMIS and its plasmin-generated carboxy-terminal domain, duplicate cultures of A431 cells were treated with 5, 10, or 20 µg of the protein. A431 cells that received 20 µg carboxy-terminal rhMIS once at the time of plating exhibited 42.5% inhibition relative to the untreated controls after 72 hours. Similar doses of intact IAP rhMIS produced variable results, from 0% to approximately 34% inhibition (n=5). Daily addition of the carboxy-terminal fragment for three days, however, produced significant inhibition (P<0.05) of proliferation of approximately 75% with the 20 µg dose (FIG. 16) relative to that in untreated controls. The carboxy-terminal domain of rhMIS was also significantly different from the corresponding pH buffer control, which slightly inhibited cell proliferation.

III. Discussion

The results presented in this study support the conclusion that to be biologically active, rhMIS, like other members of its supergene family, must be proteolytically processed. Furthermore, the ability of rhMIS to cause regression of the fetal Müllerian duct in vitro and to inhibit human tumor cell proliferation in monolayer culture appears to reside in the carboxy-terminal 25-kDa dimeric domain of the molecule. For these experiments, the carboxy-terminal region of rhMIS was generated by plasmin cleavage, followed by P-100 chromatography. The identity of the protein produced as the carboxy-terminal rhMIS dimer was based on several observations. Namely, it has already been confirmed by sequence analysis that plasmin treatment of IAP rhMIS, the source for all subsequent purifications in this study, generates the carboxy-terminal fragment (Ragin, R. C., et al., submitted) (Pepinsky et al., *J. Biol. Chem.* 263:18961–4 (1988)). The current studies employed similar chromatographic techniques to separate the carboxy-terminal dimer from other rhMIS domains, and the protein isolated crossreacted with the polyclonal antibody raised against a synthetic peptide whose sequence is contained in this region (Cate et al., *Cell* 45:685-698 (1986)). Current modifications, however, produce an isolated fragment that is biologically active, in contrast to earlier attempts that produced inactive rhMIS cleavage products (Pepinsky et al., *J. Biol. Chem.* 263:18961-4 (1988)). The specificity of the carboxy-terminal polyclonal antibody was demonstrated by its adsorption with holo-rhMIS in previous immunohistochemical studies (Kuroda et al., *Endocrinology* 127:1825-1832 (1990). Since intact rhMIS, purified to homogeneity by immunoaffinity chromatography (Ragin, R. C., et al., submitted), will regress fetal rat Müllerian ducts and a noncleavable mutant of the rhMIS molecule will not (Cate et al., In: Sporn MB, Roberts AB (eds.) *Handbook of Experimental Pharmacology*, Springer-Verlag, New York (Vol. 2:179-210 (1990), it follows that the tissues of the urogenital ridge may possess the plasmin-like enzymes (or plasmin itself) needed to activate the protein. Results from our previous studies show that partially purified bovine and human MIS inhibit the growth of certain human tumor cell lines in vitro and in vivo (Donahoe et al., *Science* 205:913-915 (1979); Fuller et al., *J. Clin. Endocrinol. Metab.* 54:1051-1055 (1982); Fuller et al., *Gynecol. Oncol.* 22:135-148 (1985); Chin, et al., *Cancer Res.* 51:2101-2106 (1991); Parry et al., *Cancer Res.*, in press), but this activity decreased as the degree of purity of MIS increased with purification (Wallen et al., *Cancer Res.* 49:2005-2011 (1986)). This problem was partially resolved by the removal of a contaminating MIS inhibitor (Chin et al., *Cancer Res.* 51:2101-2106 (1991)), but antiproliferative activity in culture remained preparation dependent. As data showing the biological activity of the plasmin-generated carboxy-terminal domain of rhMIS in the regression assay were developed, our suspicions were confirmed that tumor cells in culture may lack the ability to activate the latent form of MIS, thus yielding false negative results. The inconsistency of the antiproliferative activity may have been the result of variable degrees of proteolytic processing of the rhMIS as it is secreted from the clonal cell line now used to produce the protein. Electrophoretic analysis of the recombinant protein always shows evidence of molecular weight species smaller than those predicted from the primary structure (Cate et al., *Cell* 45:685-698 (1986).

The data reported here indicate that, like Müllerian duct regression, inhibition of A431 cell growth can be demonstrated with the carboxy-terminal domain of rhMIS. Since holo rhMIS caused variable results in A431 cell inhibition assays, it is likely that A431 cells may not process intact rhMIS to an active form. The finding that the 20 µg/day dose given over three days resulted in the same number of cells as that originally plated suggests that the carboxy-terminal domain prevented cells from entering the S phase of the cell cycle. In fact, $G_1$ blockade by rhMIS has been documented by FACS analysis when IAP preparations have been active in the monolayer assay (Hudson et al., unpublished results). It is of interest that transforming growth factor-β, a member of the same gene family as MIS, has been shown to block $G_1$-S phase transition (Laiho et al., *Cell* 62:175-185 (1990)). In addition, Rb, a known tumor suppressor gene, blocks cells in early $G_1$ (Goodrich et al., *Cell* 67:293-302 (1991)). Alternatively, the rhMIS-C preparations may interfere with cell adhesion, thus reducing the number of cells at the end of the experiment.

Sequence analysis of the bovine, human, and rat MIS genes reveals nearly exact match homology for the amino acids in the carboxy-terminal 25 kDa dimer domain for all three species. The amino-terminal regions, that is the domains up-stream from the plasmin cleavage site, are considerably less conserved. It is interesting, therefore, that the natural biological activity of MIS as a regressor of the anlagen to the female reproductive tract in male embryos can be mapped to the most evolutionarily conserved region of the molecule.

EXAMPLE 4

Introduction

To examine the effects of the Müllerian Inhibiting Substance (MIS) gene, a negative regulatory gene, on in vitro and in vivo tumor growth characteristics, Chinese hamster ovary (CHO) cells were transfected with the MIS gene and compared to mutant or nontransfected cells. Müllerian Inhibiting Substance is a member of an enlarging gene family that includes the transforming growth factor-βs (Derynck, R., et al., *Nature* 316:701-705 (1985)), inhibins (Mason, A. J., et al., *Nature* 318:659-663 (1985)), activin (Ling, N., et al., *Nature* 321:779-782 (1986); Vale, W., et al., *Nature* 321:776-779 (1986)), decapentaplegia protein of Drosophila (Padgett, R. W., et al., *Nature* 325:81-84 (1987)), Xenopus Vgl (Weeks, D. L., et al., *Cell* 51:861-867 (1987)), and a series of bone morphogenesis factors (Wozney, J. M., et al., *Science* 242:1528-1534 (1988)). Members of this gene family express structurally related proteins involved in growth regulation and differentiation. Synthesized by the Sertoli cells of the fetal testis (Blanchard, M., et al., *Peditr. Res.* 8:968-971 (1974)), MIS is a 140 kDa glycoprotein homodimer (Picard, J. Y., et al., *Mol. Cell. Endocrinol.* 34:23 (1984); Budzik, G. P., et al., *Cell* 34:307-314 (1983); Budzik, G. P., et al., "A Possible Purification of Müllerian Inhibiting Substance and a Model of Its Mechanism of Action," in Developmental Mechanisms: Normal and Abnormal, Alan R. Liss, New York (1985), pp. 207-223) that is responsible in the male fetus for regression of the Müllerian duct (Jost, A., *Arch. Anat. Microsc. Morphol. Exp.* 36:271-315 (1947)) which in the female fetus, normally develops into the uterus, fallopian tubes, and upper third of the vagina. Since MIS inhibits growth of M üllerian duct cells during development, a similar effect on transformed cells derived from these tissues was anticipated. Thus, partially purified bovine MIS was tested and found to inhibit growth of established Müllerian-derived tumor cell lines in vitro (Donahoe, P. K., et al., *Science* 205:913-915 (1979), Fuller, A. F., et al., *J. Clin. Endocrinol. Metab.* 54:1051-1055 (1982)) and in vivo (Donahoe, P. K., et al., *Ann. Surg.* 194:472-480 (1981)), and highly purified bovine MIS inhibited colony growth of a large number of primary Müllerian-derived cancers obtained directly from patients (Fuller, A. F., et al., *Gynecol. Oncol.* 22:135-148 (1985)).

The human gene for MIS was subsequently isolated and the recombinant protein (rhMIS) expressed in CHO cells (Cate, R. L., et al. *Cell* 45:685-698 (1986)). Although the purified protein is bioactive, causing regression of the M üllerian duct of the 14.5 day fetal rat in a semi-quantitative organ culture assay (Donahoe, P. K., et al., *J. Surg. Res.* 23:141-148 (1977)), initial studies investigating the antiproliferative effect of this recombinant product showed minimal inhibition (Wallen, J. W., et al., *Cancer Res.* 49:2005-2011 (1989)). More recently, however, the addition of a pre-elution high salt wash step, prior to elution from an anti-MIS monoclonal immunoaffinity column with 1M acetic acid (pH 3) (Ragin, R. C., et al., *Protein Expression and Purification* 3(3):236-245 (1992)), has resulted in rhMIS preparations with more consistent antiproliferative activity against a variety of human tumors of Müllerian duct origin (Chin, T., et al., *Cancer Res.* 51:2101–2106 (1991)). Similar but unexpected growth inhibition was observed against a human ocular melanoma cell line (Parry, R. L., et al., *Cancer Res.* 52:1182–6 (1992)).

Dihydrofolate reductase (DHFR) deficient CHO cells (Chasin, L., et al., *Proc. Natl. Acad. Sci. U.S.A.* 77:4216–4220 (1980)) were found to grow in anchorage dependent and independent conditions in vitro. We also found that they formed substantial tumors when implanted beneath the murine renal capsule, and grew lung nodules following tail vein injection into genetically immunodeficient mice. When the growth of "wild-type" CHO cells (CHO-WT) was compared to CHO cells transfected with a gene for human MIS (B9) or with a mutated gene which produces a noncleavable, inactive form of human MIS (L9) the cell line transfected with the MIS gene had both impaired proliferation and less metastatic potential. OM431 cells transfected with the MIS gene also grew less well in vitro and were substantially inhibited in vivo. In addition, when highly purified exogenous recombinant human MIS was delivered via intraperitoneal osmotic pumps, metastases from ocular melanoma cells were significantly reduced, correlating the observed effect in transfected cells with that caused by the exogenously introduced gene product, MIS.

Materials And Methods

Cell Lines. CHO cells deficient in DHFR (Chasin, L., et al., *Proc. Natl. Acad. Sci. U.S.A.* 77:4216–4220 (1980)), and designated as wild type (CHO-WT), were used to express the human MIS gene. A 4.5 kb Afl II genomic fragment containing the entire MIS coding region was inserted into an expression vector carrying the SV40 early promoter. This plasmid (pBG311.hmis) was co-transfected with a plasmid (pAdD26) (Kaufman, R. J., et al., *Mol. Cell. Biol.* 2:1304–1319 (1982)) containing the enhancerless mouse DHFR complementary DNA into CHO-WT cells, and the MIS gene copy number subsequently increased with methotrexate selection (Cate, R. L., et al. *Cell* 45:685–698 (1986), Wallen, J. W., et al., *Cancer Res.* 49:2005–2011 (1989); Cate et al., in *Handbook of Experimental Pharmacology*, Vol. 95/II, Peptide Growth Factors and Their Receptors II, pp. 179–210 (1990)). This cell line, designated B9, produced approximately 3.0 µg rhMIS/ml/24 h, as measured by a previously described MIS ELISA (Wallen, J. W., et al., *Cancer Res.* 49:2005–2011 (1989); Hudson, P. L., et al., *J. Clin. Endocrinol. Metab.* 70:16–22 (1990)). B9 cultures contained 30 nM methotrexate in addition. A third CHO cell line, designated L9, was similarly created by transfection of a mutated human MIS gene, which produces a noncleavable protein with arginine #427 changed to threonine (Cate et al., in *Handbook of Experimental Pharmacology*, Vol. 95/II, Peptide Growth Factors and Their Receptors II, pp. 179–210 (1990)). The altered protein was inactive (Cate et al., in *Handbook of Experimental Pharmacology*, Vol. 95/II, Peptide Growth Factors and Their Receptors II, pp. 179–210 (1990)) in the urogenital ridge organic culture bioassay (Donahoe, P. K., et al., *J. Surg. Res.* 23:141–148 (1977)). Although each cell line produces an equal amount of protein.

The OM431 cell line, established in vitro from a primary tumor specimen obtained at enucleation (Albert, D. M., et al., *Inv. Ophth. Vis. Sci.* 25:1284–1299 (1984)), was confirmed by light and electron microscopy and chromosome analysis to be a human ocular melanoma with Callender (Callender, G. R., *Trans. Am. Acad. Ophth. Otol.* 36:131 (1931)) epithelial morphology. This cell line was transfected with the pc DNA I/neo. hmis plasmid vector.

Transfection of pcDNAI/neo.hmis. MIS cDNA (2036 bp) was obtained from the vector, pD1 (Cate, R. L., et al., "Müllerian Inhibiting Substance," in *Handbook of Experimental Pharmacology*, Vol. 95/II, Peptide Growth Factors and their Receptors II, Sporn and Roberts, eds., Springer-Verlag, New York, pp. 179–210 (1990)), created which had been cut from the pBG312, by incubating for one hour at 37C with Hind III and Not I in buffer C (Promega). This insert was then ligated for 16 hours at 18C to the stable eukaryotic expression vector pcDNA I/NEO (7.1 Kb, Invitrogen) that had previously been cut with the same enzymes. Both the vector and the insert containing vector were run on and cut from 1% agarose gels, transfected into *E. coli* using electroporation (2.47 kV, 25 uf, 400 ohms) and the cells plated overnight on 1% agar plates containing 20 ug/ml Kanamycin. Colonies were selected and grown overnight in LB broth containing 20 ug/ml Kanamycin. A mini-prep of each colony, again using Hind III and Not I, revealed clones transfected with vector alone or the vector plus insert. Selected clones were grown overnight in 1 L LB broth (20 ug/ml Kanamycin) produced adequate amounts of the plasmid for stable transfection of OM431 cells using calcium phosphate and G418 selection. Presence of the MIS cDNA in the OM431 cell line was confirmed by ELISA which detected approximately 3 ugm rhMIS/ml/24 hr in the culture media.

The cell lines were free of adventitious bovine viruses and mycoplasma and were used within 60 generations of original plating. Each cell line was carried in the alpha modification of minimal essential media without nucleosides (α-MEM-), but with added glucose, glutamine, sodium pyruvate, amikacin, and 10% MIS-free female fetal calf serum (FCS).

Cell Line and Media Analyses. Doubling times were determined by plating $5 \times 10^4$ cells in 10–12 replicate 60 mm diameter culture plates. After 10–12 h, two dishes were counted every 48 h. The cell numbers were averaged, and the number of doublings achieved calculated using the following equation:

$$\text{\# Doublings Achieved} = \frac{\ln (\text{final density/initial density})}{\ln 2}$$

"Doubling time" was calculated by dividing the time in culture (hours) by the number of doublings achieved.

Serum-free media was obtained from 72-h monolayer cultures of the transfected and parent CHO and OM431 cell lines for total protein and rhMIS measurement, as well as Western analysis. Protein quantitation was performed by the method of Bradford (Bradford, M. M., et al., *Anal. Biochem.* 72:248–254 (1976)), while MIS concentrations were measured by ELISA (Hudson, P. L., et al., *J. Clin. Endocrinol. Metab.* 70:16–22 (1990)). MIS was then purified from each media sample for Western analysis (Towbin, H., et al., *Proc. Natl. Acad. Sci. U.S.A.* 76:4350–4354 (1979)) by lentil-lectin extraction as previously described using a polyclonal anti-rhMIS antibody (MGH-1; 1:1000) (Ragin, R. C., et al., *Protein Expression and Purification* 3(3):236–245 (1992)). 100–300 ng of MIS can be detected per lane by this method.

Northern Analysis for MIS. Northern analysis of CHO-WT, -B9, and -L9 cells as well as OM431 transfected cells, both from monolayer culture and pulmonary metastases, was performed to evaluate MIS expression in vitro and in vivo. One 175 cm² flask of confluent cells of each type (72 hours after subculture), as well as pulmonary tissue excised from one animal of each group 20–30 days after tail vein injection and snap frozen in liquid nitrogen, were used for this study. Total RNA was extracted by a modification of the method of Chirgwin (Chirgwin, J. M., et al., *Biochemistry* 18:5294–5299 (1979)) using guanidinium thiocyanate/lithium chloride; RNA quantitation was by spectrophotometric analysis and ethidium bromide staining of test gels. Ten ug of total RNA were loaded in each lane of a 1.5% Morpholinopropanesulfonic acid-formaldehyde agarose gel, electrophoresed at 5 V/cm, transferred to Biotrans nylon membrane (ICN Biomedicals, Irvine, Calif.) by capillary action in 25 mM sodium phosphate, and then fixed by UV irradiation. The membrane was prehybridized in plaque screen buffer then hybridized with a random priming (Feinberg, A. P., et al., *Anal. Biochem.* 137:266–267 (1984)) $^{32}$P-labeled full length human MIS complementary DNA probe as previously described (Kuroda, Lee). Overnight hybridization was performed with $10^6$ cpm/ml in plaque screen buffer containing 0.1 mg/ml tRNA. All hybridizations and washes were done at 65° C.; 75 nM NaCl/7.5 mM Na citrate/0.5% SDS was the most stringent wash. Autoradiographic exposures were for 6 and 60 h.

Purification of rHMIS. Recombinant human MIS was purified using an immunoaffinity chromatography method (Ragin, R. C., et al., *Protein Expression and Purification* 3(3):236–245 (1992)) adapted from previous protocols (Shima, H., et al., *Hybridoma* 3:201–214 (1984); Pepinsky, R. B., et al., *J. Biol. Chem.* 263:18961–18964 (1988)). Briefly, the conditioned medium of the B9 cell line was loaded onto a 5 ml immunoaffinity column constructed with protein-A-Sepharose (Sigma) purified mouse monoclonal antibody, raised to gel purified rhMIS (Hudson, P. L., et al., *J. Clin. Endocrinol. Metab.* 70:16–22 (1990)), which was covalently attached to Affigel-10 agarose resin (BioRad Lab.). The column was washed with 1 column volume of high salt buffer (0.5M NaCl, 1 mM EDTA, 0.001% nonidet P-40 (NP-40, Sigma), 20 mM HEPES, pH 7.4), prior to elution with 1M acetic acid in 20 mM HEPES, pH 3.0. The MIS containing fractions were immediately neutralized with NaOH, dialyzed overnight versus 20 mM HEPES, 0.001% NP-40, pH 7.4, and then analyzed for total protein by the method of Bradford (Bradford, M. M., et al., *Anal. Biochem.* 72:248–254 (1976)), and for rhMIS concentrations by ELISA (Hudson, P. L., et al., *J. Clin. Endocrinol. Metab.* 70:16–22 (1990)). The fractions were further analyzed by polyacrylamide gel electrophoresis and western analysis is above.

Agar Inhibition Assay. Each cell line (CHO-WT, -B9, -L9, and OM431-OM431.MIS, -pcDNA I/neo.hmis) was tested in triplicate in an agarose double layer colony inhibition assay (Fuller, A. F., et al., *J. Clin. Endocrinol. Metab.* 54:1051–1055 (1982); Fuller, A. F., et al., *Gynecol. Oncol.* 22:135–148 (1985); Chin, T., et al., *Cancer Res.* 51:2101–2106 (1991)). The underlayer of 35 mm culture plates consisted of 1 ml of 0.6% agarose (Sigma) in 10% female FCS-supplemented α-MEM with nucleosides (α-MEM+). The overlayer consisted of 0.3% agarose in 10% female FCS supplemented α-MEM+, the cells (25,000 cells/ml), 10 ng/ml epidermal growth factor (Sigma), and either MIS (28.5 μg/ml) or buffer alone. The plates were incubated in humid air with 5% $CO_2$ at 37° C. for 10–21 days. Colonies with more than 30 cells were then counted with an inverted microscope (Nikon).

Multicellular Tumor Spheroid Assay. Multicellular tumor spheroids of CHO-WT, -B9, -L9 cells were produced by the method of Yuhas et al. (Yuhas, J. M., et al., *Cancer Res.* 37:3639–3643 (1977)). After thorough washing to remove residual trypsin, $10^5$ cells of each line in 1 ml of 10% female FCS-supplemented α-MEM+ were plated above 1.5 ml of 1% agarose in a 35 mm culture plate and incubated in humid air with 5% $CO_2$ at 37° C. for 2–5 days, when spheroids usually formed. One-half mL of 1% agarose, overlayered with 0.5 ml of 10% female FCS supplemented α-MEM+, was then placed in each well of a 24-well culture plate (Falcon, #3047, Oxnard, Calif.). Individual spheroids of similar size (approximately 250 mm diameter) were selected from the 35 mm plate under a dissecting microscope and transferred by micropipette, each to a separate well. Spheroid volumes were determined on day zero and at regular intervals by measuring the longest diameter (L), and the diameter perpendicular to the longest one (W), and expressing the relative volume as (L×W×W). The relative volume of each spheroid was obtained by comparing its size on day 9 to its starting volume.

Subrenal Capsule Assay. Following the method of Bogden (Bogden, A. Z., et al., *Exp. Cell. Biol.* 47:281–293 (1979)) as subsequently modified by Fingert (Fingert, H. J., et al., *Cancer Res.* 47:3824–3829 (1987)), the three CHO cell lines and the two OM431 cell lines were tested for growth in vivo in a murine subrenal capsule assay. Ten million cells from each line were centrifuged at 1500 rpm for 5 min to form a pellet. Fifteen μl of fibrinogen (Sigma, 20 mg/ml, dissolved in phosphate-buffered saline, pH 7.4), were added to the pellet, followed by 8 μl of thrombin (Sigma, 20 unit/ml, dissolved in double-strength Dulbecco's modification of minimal essential medium). This mixture was incubated at 37° C. for 15 min. The cell clot thus formed was cut into approximately 50 fragments (1 $mm^3$–$2×10^5$ cells) in preparation for implantation. Selected fragments were dissolved and cells counted to confirm uniformity of cell counts.

Female nude mice (nu) (Pantelouris, E. M., *Nature* 217:370–371 (1968)) (8 weeks old, average weight 24 g, Edwin L. Steel Laboratory, Massachusetts General Hospital, Boston, Mass.) were used. All animals were cared for under NIH approved guidelines established by the Massachusetts General Hospital. After inducing anesthesia with an intraperitoneal injection of 0.3 ml of 10% pentobarbital (Abbott Laboratory, North Chicago, Ill.), a subcapsular space was developed in the left kidney with a 19-gauge needle trocar. A cell clot was then introduced with a 1 mm segment of 5-0 nylon suture, which was used both to calibrate implant measurements and to localize the tumor. The longest diameter ($L_1$) of the implant, the diameter perpendicular to the longest diameter ($W_1$), and the length of the suture were measured with the ocular micrometer of a dissecting microscope. Each of the cell lines was implanted into five animals and allowed to grow for eight days, at which time the same measurements were repeated to calculate the graft size ratio $(L_2×W_2×W_2)/(L_1×W_1×W_1)$. Histology was reviewed to assure that the implanted tumor was viable and lacked both an inflammatory infiltrate and central necrosis.

Metastases Assay. CHO-WT, -B9 (as well as clones 4 and 7), -L9 cells, OM431-WT, and OM431-pcDNA I/neo.hmis ($10^6$) were suspended in 0.25 ml of 10% female FCS supplemented α-MEM+ and injected via 27 gauge needles into the tail veins of severe combined immunodeficient (SCID) mice (n=10 per cell line), which are both B and T cell deficient (Custer, R. P., et al., *Am. J. Path.* 120:464–477 (1985); Hendrickson, E. A., et al., *Proc. Natl. Acad. Sci U.S.A.* 88:4061–4065 (1991)), selected because similar injections of OM431 cells had failed to produce metastases within 8–10 weeks in T cell deficient nude mice and triple deficient mice lacking T, B, and NK cells (Zietman, A. L., et al., *Int. J. Cancer* 47:755–759 (1991)). The mice were sacrificed at 21 days, the heart and lungs removed en bloc, the lungs inflated and preserved in Bouins' solution, and the total number of visible surface lung metastases counted 24 hours later. Lung tissue was oriented and cut in the coronal plant in 8 μm sections. Length of survival of a second group of SCID mice (n=10 per cell line) after tail vein injection of these cell lines was also determined.

OM431 human ocular melanoma cells (untransfected) ($10^6$) were suspended in 0.25 ml media and injected into the tail veins of two groups of SCID mice. In the first experiment, ten SCID mice had eight-day Alzet mini osmotic pumps (model #2001, Alza Corp. Palo Alto, Calif.) placed within their peritoneal cavities 24 h prior to the tail vein injections, with half of the pumps containing purified rhMIS (67.8 μg) and half containing buffer only (200 μl 20 mM HEPES, pH 7.4). The pumps were removed at nine days. After the animals were sacrificed at six weeks, lungs were prepared and metastases counted as above. In a second larger group of OM431 injected SCID mice, the first osmotic pump was replaced with a second pump on day eight (total MIS delivered—92 μg). Lungs were again removed at six weeks, cut in 8 m sections, and reviewed histologically, since surface metastases were not yet visible. The central coronal section of the lung from each animal was selected and scanned using AppleScan with a Macintosh IIcx computer. Image analysis was performed using the software program "Image" (ver. 1.36) to determine the average area of visible metastases and the percent total lung area taken up by metastatic growth. "Image" is a public domain, digital image processing and analysis program for the Macintosh computer.

Statistics. Statistical analysis were performed using a Macintosh computer and "MYSTAT", a software package distributed by SYSTAT, Inc., Values for colony counts, number of metastases, relative pulmonary tumor area, and length of survival are expressed as the means ± standard error (SE). Independent Student's t tests were used to determine the levels of statistical significance (p values).

Results

Figure 19:
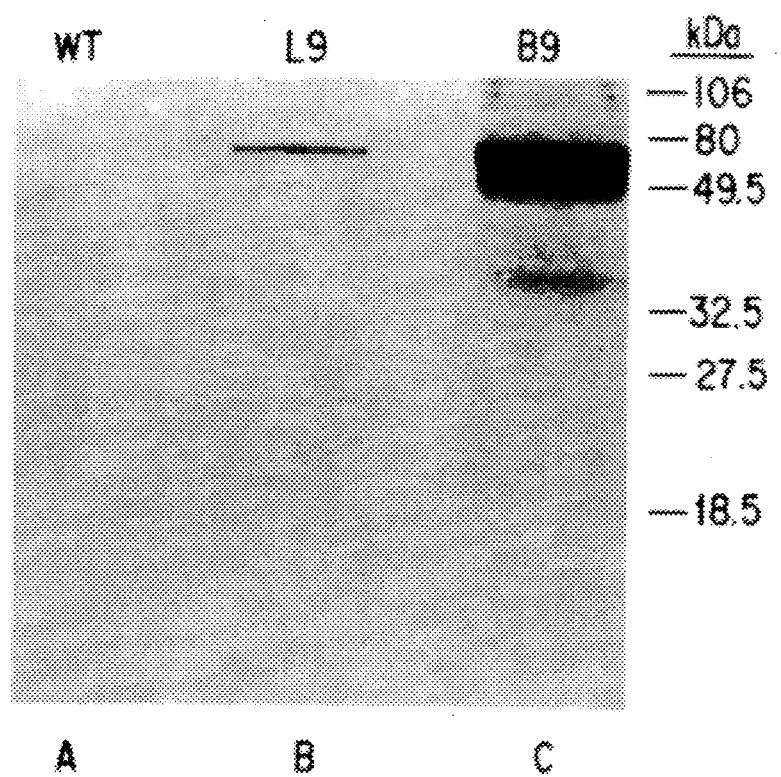
FIG. 19. Western analysis of CHO-WT, B9, and L9 cell culture media. MIS was purified from serum-free CHO-WT (lane A), L9 (lane B), and B9 (lane C) media samples by lentil-lectin extraction, and anti-holo-rhMIS primary antibody (MGH-1) was subsequently used for Western analysis. The predominant 70 and 55 kDa bands in B9 media represent holo- and amino-terminal rhMIS, while the less abundant 70 kDa L9 band corresponds to noncleavable holo-MIS.
Figure 20:
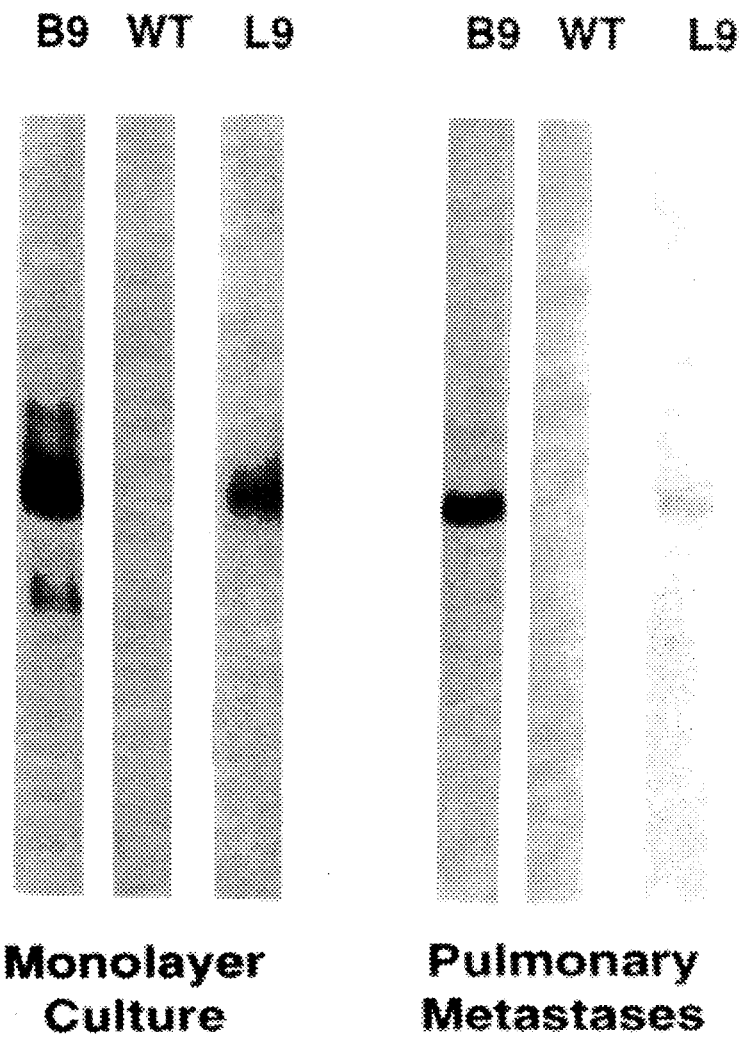
FIG. 20. Northern analysis of CHO-WT, B9, and L9 cells and pulmonary metastases. Total RNA was extracted from CHO-WT, B9, and L9 cells in monolayer culture and from metastases-containing lungs after tail vein injections of SCID mice. MIS mRNA is detectable in both cells and metastases of the B9 and L9 lines, although less abundant in the latter cell lineage. Note the absence of detectable message in CHO-WT cells and metastases. (Exposure time 6 h for B9, CHO-WT; 60 h for L9).

Cell Line Analysis. The doubling time for each of the three CHO cell lines in this study was 16 hours in monolayer culture. The protein concentrations for CHO-WT, B9, and L9 media samples after 3 days in culture were 200, 146, and 104 ug/ml, respectively, while MIS levels were 21 μg/ml for B9 media and undetectable in L9 and CHO-WT media. Western analysis demonstrated strong 70 and 55 kDa MIS protein bands in B9 extracted media, corresponding to holo- and amino-terminal rhMIS, and a less intense 70 kDa band in L9 media (FIG. 19). This latter band corresponds to noncleavable "mutant" holo-MIS. There was no detectable MIS in the CHO-WT extracted media. Northern analysis of B9 cells and their pulmonary metastases after tail vein injection demonstrated an abundant MIS mRNA transcript of approximately 2.0 kilobases (FIG. 20). L9 cells and their pulmonary metastases, meanwhile, produced an identical, but less abundant MIS transcript, no transcription of MIS was detected in CHO-WT cells or pulmonary metastases.

Figure 21:
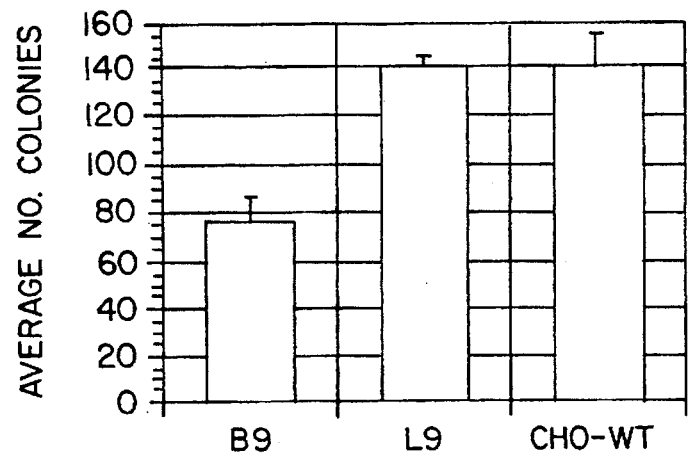
FIG. 21. The three CHO cell lines were tested in triplicate for their ability to form colonies in a double-layer agarose colony inhibition assay. The average number of colonies produced by MIS transfected B9 cells was 76±11, compared to 139±6.3 for L9 cells (p=0.005) and 140±5.5 for CHO-WT cells (p=0.003).
Figure 22:
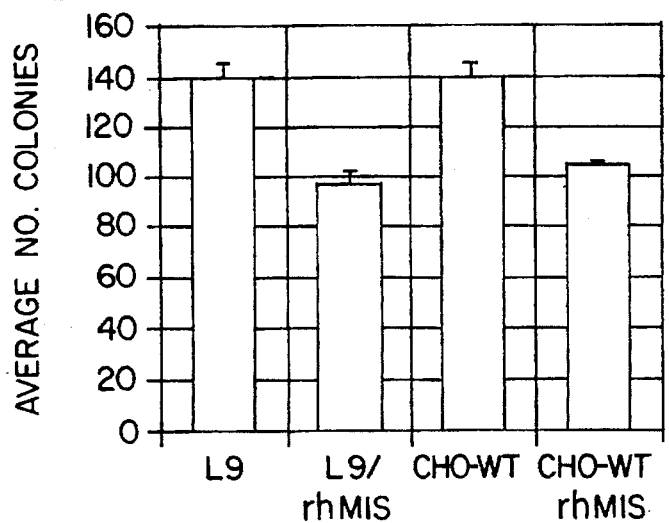
FIG. 22. The L9 and CHO-WT cell lines were tested in triplicate for their ability to grow in the presence of exogenous rhMIS in a double-layer agarose colony inhibition assay. When 28.5 ug rhMIS/ml was used in this assay, L9 cells grew 98±3.5 colonies and CHO-WT cells formed 103±0.8 colonies. This reduction in colony formation compared to treatment with buffer alone was statistically significant for both the L9 (p=0.005) and CHO-WT (p=0.003) lines.

Agar Inhibition Assay. B9, L9, and CHO-WT cells were tested in triplicate for their ability to form anchorage independent colonies in a double-layer agarose colony inhibition assay. The B9 cell line grew 76±11 colonies, while L9 grew 139±6.3 (p=0.005), and CHO-WT grew 140±5.5 colonies (p=0.003) (FIG. 21). When exogenous rhMIS (28.5 ug/ml, ~200 nM) was added to B9, L9 and CHO-WT cells in this assay, B9 grew 89±1.5 colonies, L9 grew 98±3.5 colonies and wild type grew 103±0.8 colonies (FIG. 22). This reduction in colony formation compared to treatment with buffer alone was statistically significant for the L9 and CHO-WT cell lines (p=0.005 and 0.003, respectively).

Multicellular Tumor Spheroid Assay. When tested for its ability to form anchorage independent multicellular tumor spheroids, the B9 cell line produced only loose cellular aggregates. No discrete tumor colonies formed that could be transferred to a 24-well plate. The L9 and CHO-WT lines, on the other hand, produced large spheroids. There was no statistical difference between the relative volumes of spheroids formed by L9 and CHO-WT cells at 9 days.

Figure 23:
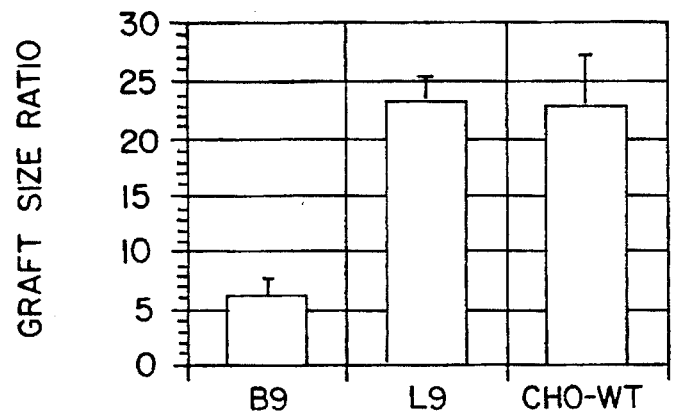
FIG. 23. The in vivo growth of CHO-WT, B9, and L9 cell lines was evaluated in a murine subrenal capsule assay. Eight days after implantation beneath the murine renal capsule, the graft size ratios (GSR) were 6.04±1.77 (n=5) for B9 cells, 23.2±2.01 (n=5) for L9 cells (p=0.001), and 22.8±4.26 (n=5) for CHO-WT cells (p=0.007).

Subrenal Capsule Assay. When placed in a clot under the murine renal capsule, B9, L9, and CHO-WT cells all formed measurable tumors. After eight days, the graph size ratios (GSR) were 22.8±4.26 (n=5) for the CHO-WT line, 23.2±2.01 (n=5) for the L9 line, and 6.04±1.77 (n=5) for the B9 line (FIG. 23). The differences between B9 and L9, and B9 and CHO-WT were significant (p=0.001 and 0.007, respectively).

Figure 24A:
FIGS. 24A and 24B. Pulmonary metastases following tail vein injection of B9, L9, or CHO-WT cells into severe combined immunodeficient mice. A) Surface metastases averaged 18±3.9 in B9-injected animals (first row), while L9-injected animals (second row) developed 53±6.8 metastases (p=0.001) and CHO-WT-injected animals (third row) developed 81±14 metastases (p=0.001). B) Representative coronal sections of mid-lung from these animals show the relatively smaller cross-sectional area occupied by B9 tumors (9.44%±1.70), compared to L9 (53.75%±7.18) and CHO-WT (50.84%±6.07) tumors. This difference between B9 and L9 tumors (p=0.000) and B9 and CHO-WT tumors (p=0.000) was highly significant.
Figure 24B:
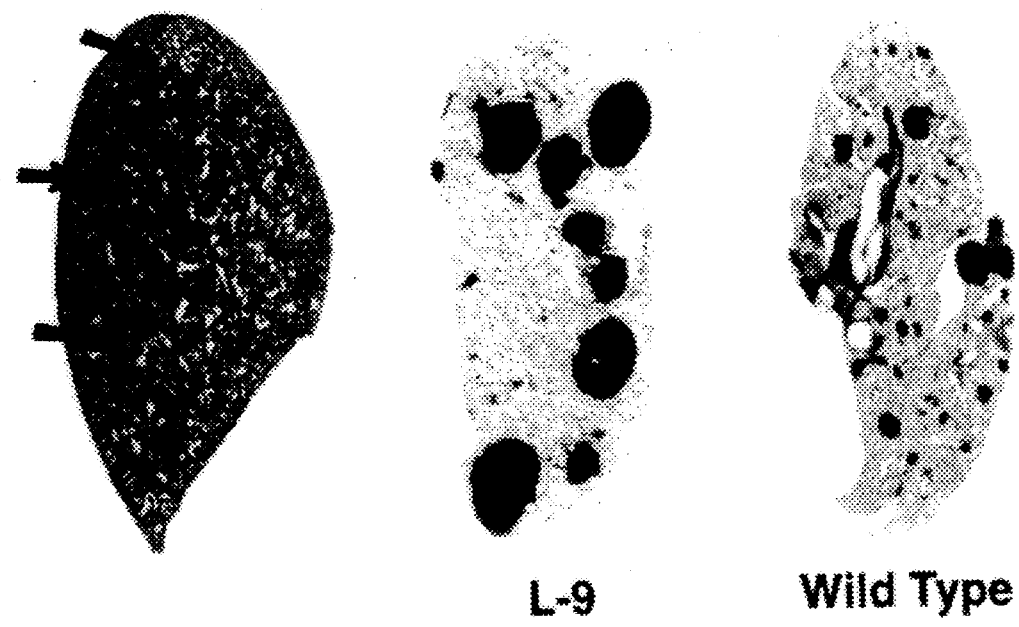

Metastases Assay. Following tail vein injection of $10^6$ cells of the CHO-WT, B9, and L9 lines into severe-combined immunodeficient (SCID) mice, lung metastases were noted—but found to be different—in all three groups by 20 days. The number of surface metastases in animals injected with B9 cells was 18±3.9 (SE) (n=7), while L9 cells produced 53±6.8 (n=7) (p=0.001) and CHO-WT cells produced 81±14 (n=6) (p=0.001) (FIG. 24A). The L9 cell line also produced metastases in the adrenals, the chest wall, and the peri-iliac and peri-aortic regions. Histologic examination of pulmonary sections from these mice, meanwhile, revealed a large number of very small B9 tumor nodules in numbers not significantly different from those of the much larger L9 and CHO-WT metastases. However, when tumor area as a percent of total lung area was evaluated in a central coronal cross-section (FIG. 24B) for each mouse, the B9-injected animals had a relative tumor area of only 9.44%±1.70, compared to 53.75%±7.18 for L9 animals (p=0.000), and 50.84%±6.07 for CHO-WT animals (p=0.000). There was no statistical difference between L9 and CHO-WT relative tumor areas (p=0.73). A similar pattern was observed in the lengths of survival for a second set of injected animals; SCID mice injected with B9 cells survived for 42.6±0.8 days, compared to 23.4±0.6 days for CHO-WT animals (n=10) and 25.0±2.1 days for L9 animals (n=10) (p=0.000) for both groups).

Figure 25A:
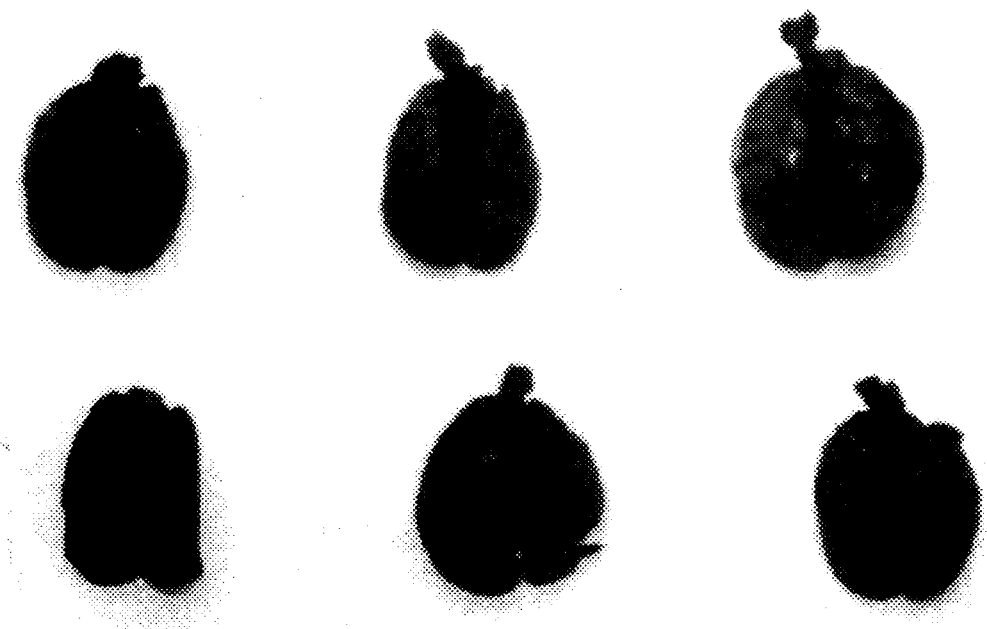
FIGS. 25A and 25B. Pulmonary metastases following tail vein injection of OM431 cells into severe combined immunodeficient mice. A) Lungs from animals treated with rhMIS (second row) via an Alzet pump within the peritoneal cavity for 8 days showed a smaller number of surface metastases at six weeks (4.6±2.9) than buffer-treated controls (37±17; p=0.09). B) The cross-sectional area occupied by metastatic OM431 tumors at 6 weeks in the mid-lung of animals treated with rhMIS for 16 days (2.05±0.53%) was significantly less (p=0.01) than the relative area of lung metastases in buffer-treated controls (18.99±5.75%).

To confirm that the reduced number of metastases seen in the B9-injected mice was caused by MIS, animals injected with OM431 human ocular melanoma cells were treated with exogenous rhMIS. In the first smaller group of animals treated for 8 days, mice (n=5) receiving rhMIS (67.8 μg total dose) had 4.6±2.9 surface lung metastases at 6 weeks, while animals receiving buffer alone (n=4) had 37±17 surface metastases (p=0.09) (FIG. 25A). The percent total lung area taken up by metastatic growth in a central coronal 8 μm section of a lung for each animal was 3.89% ±0.76 for the rhMIS treated group and 9.94%±0.16 for the buffer treated group (p=0.058).

Figure 25B:
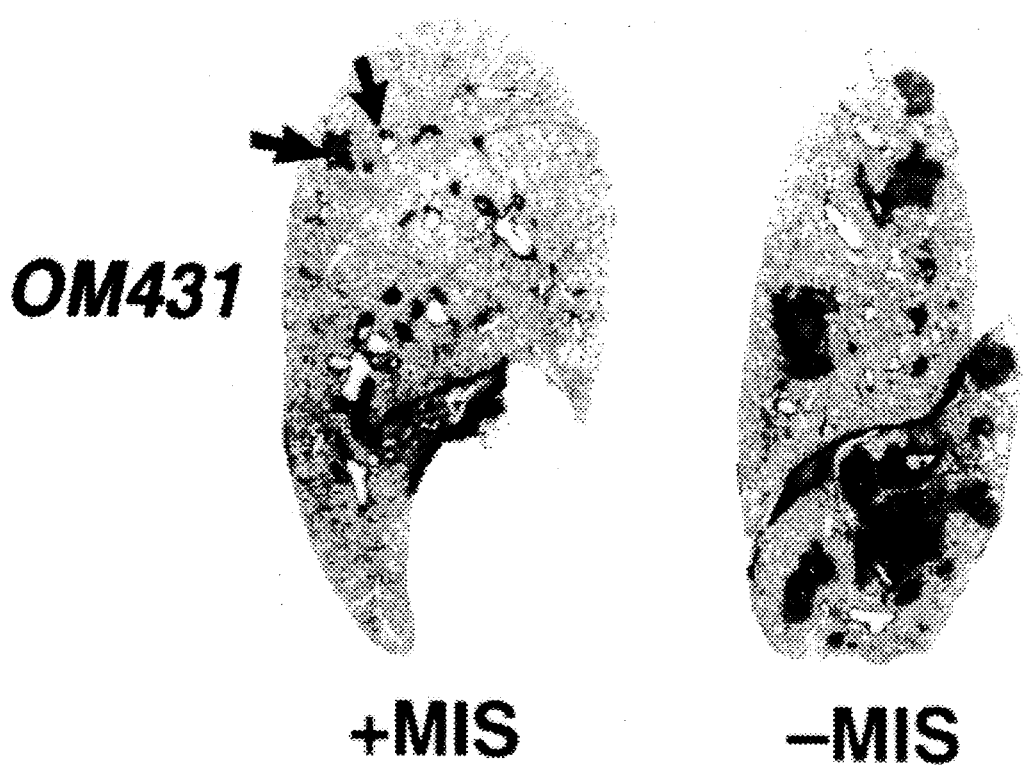

In the second larger group of mice treated with exogenous rhMIS for 16 days, the number of metastases in rhMIS (92 μg total dose) treated animals (n=10), as determined by histologic review of similar doronal sections, was 15.4±3.8, compared to 26.4±6.4 for buffer treated animals (n=10) (p=0.21). Since the metastases observed in the MIS-treated animals were very small, the relative lung areas occupied by tumor were also calculated. The percent total lung area taken up by metastatic growth in a central coronal 8 μm section of a lung for each animal was 2.05±0.53 for the rhMIS treated group, compared to 18.99±5.75% of the buffer treated group (p=0.01) (FIG. 25B).

Figure 26:
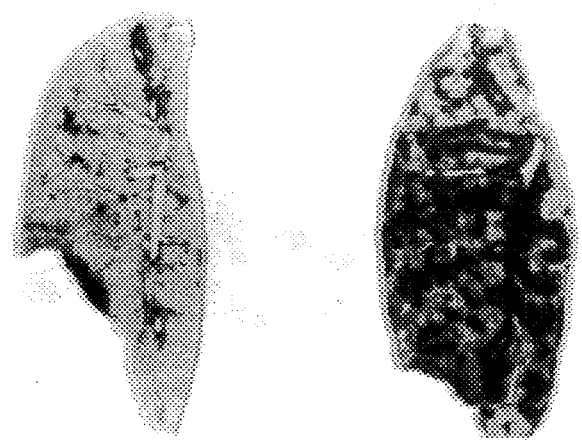
FIG. 26. Pulmonary metastases following tail vein injection of $10^6$ OM431 cells, transfected with the gene for MIS (left), and $10^6$ OM431 wild-type cells (right), into severe combined immunodeficient mice. Representative coronal sections of mid-lung from these animals show the relatively smaller cross-sectional area occupied by OM431 cells transletted with the MIS gene (14.14±7.78[sd]%), compared to wild-type OM431 (35.83±8.10[sd]%). The difference between MIS-transfected and wild type cells (p=0.000) was highly significant.

When the MIS gene construct was transfected into the ocular melanoma cell line, and $10^6$ cloned cells injected into the tail vein of SCID mice, the tumors were much smaller than observed after injection of wild type OM431 cells. The percent total lung area taken up by metastatic growth in a central coronal section of a lung for each animal was 14.14±7.78% for the MIS transfected cells, compared to 35.83±8.10% for the wild type OM 431 cells (p=0.000) (FIG. 26).

Discussion

Differentiating agents which modulate the growth of malignant cells are being evaluated as therapeutic anti-tumor agents. Exogenous Müllerian Inhibiting Substance inhibits the growth of a number of human carcinoma cell lines and primary human tumors both in vitro and in vivo (Donahoe, P. K., et al., Science 205:913–915 (1979); Fuller, A. F., et al., J. Clin. Endocrinol. Metab. 54:1051–1055 (1982); Donahoe, P. K., et al., Ann. Surg. 194:472–480 (1981); Chin, T., et al., Cancer Res. 51:2101–2106 (1991); Parry, R. L., et al., Cancer Res. 52:1182–6 (1992)), but the efficacy of highly purified recombinant human holo MIS appears to be dependent on the degree of cleavage and release of the smaller C-terminal active domain (MacLauglin D. T., et al., Endocrinology 131(1):291–296 (1992)). Experiments were therefore designed to determine whether transfecting the MIS gene into a eukaryotic cell line could more consistently alter in vitro and in vivo tumor growth characteristics, both to confirm the results seen with selected preparations of exogenous rhMIS and in anticipation of future targeted gene therapy.

An expression vector carrying the SV40 early promoter and genomic MIS was co-transfected with a plasmid containing an enhancerless mouse DHFR cDNA (Kaufman, R. J., et al., Mol. Cell. Biol. 2:1304–1319 (1982)) into a DHFR-deficient CHO cell line (Chasin, L., et al., Proc. Natl. Acad. Sci. U.S.A. 77:4216–4220 (1980)). Clones were selected and amplified with increasing doses of methotrexate to produce the MIS expressing cell line, B9 (Cate et al., in Handbook of Experimental Pharmacology, Vol. 95/II, Peptide Growth Factors and Their Receptors II, pp. 179–210 (1990)). Constructs identical to these, except for containing a mutated form of the human MIS gene with threonine substituted at arginine #427 were also transfected into this CHO cell line. This third cell line, designated L9, produced an MIS protein that is protected from cleavage and is therefore biologically inactive in the standard MIS organ culture assay (Cate et al., in Handbook of Experimental Pharmacology, Vol. 95/II, Peptide Growth Factors and Their Receptors II, pp. 179–210 (1990)).

Anchorage independent cell growth has been correlated with cell tumorigenicity and experimental metastatic potential (Mancianti, M. L., et al., Carcinog. Compr. Surv. 11:369–86 (1989); Li, L., et al., J. Natl. Cancer Inst. 81:1406–1412 (1989); Paraskeva, C., et al., Anticancer Res. 10:1189–1200 (1990)). The DHFR-deficient CHO-WT cell line used in these experiments grew well as colonies in both agarose and multicellular tumor spheroid assays, reflecting a certain degree of anchorage autonomy. The non-cleavable mutant MIS cell line, L9, grew equally well in these assays, indicating that transfection with the plasmid vectors did not significantly alter in vitro cell growth characteristics. Although we could not achieve comparable transcription (FIG. 20) or translation (FIG. 19) of the non-cleavable mutant, the L9 line provides a reasonable vector control for comparison with B9. Colony growth of the MIS transfected B9 cell line, however, was significantly inhibited in agarose, and B9 cells failed to form multicellular tumor spheroids. Purified rhMIS added exogenously similarly inhibited colony formation of CHO-WT and L9 cells dispersed in agarose, but had no additional inhibitory affect on B9 colony formation. All three cell lines had identical in vitro anchorage dependant doubling times in monolayer culture.

To compare the in vivo growth characteristics of these three cells lines, tumor cell growth beneath the renal capsule and the development of lung metastases after tail vein injection were evaluated. The subrenal capsule assay permits the introduction into a nutrient rich environment of a known number of cells whose contained growth can be accurately measured. Cells injected via the tail vein, meanwhile, are given direct access to the circulation. This experimental metastases assay, which examines the ability of cells to travel in the circulation and implant at a specific site (Smyth, M. J., et al., Cancer Res. 51:310–317 (1991); Sharkey, R. M., et al., J. Natl. Cancer Inst. 83:627–632 (1991)), as been found to correlate well with in vitro anchorage-independent growth (Li, L., et al., J. Natl. Cancer Inst. 81:1406–1412 (1989)). The in vivo growth of the MIS transfected B9 cell line was significantly inhibited when compared to the more luxuriant growth of L9 and CHO-WT lines (FIGS. 23 and 24), thus mirroring the MIS induced inhibition exhibited in anchorage independent in vitro assays.

The genetic events that induce or suppress the tumor metastatic process are incompletely understood. Recent investigations correlated reductions in pulmonary metastases after tail vein injections with the presence of the nm23 gene (Leone, A., et al., Cell 65:25–35 (1991)) and the RB gene Huang et al., Science 242:1563–1566 (1988); Bookstein, R., et al., Science 247:712–715 (1990)). Transfection of the MIS gene into the CHO cell line resulted in a similar reduction of surface pulmonary metastases (FIG. 24A). Histologic analysis, meanwhile, showed a large number of very small tumor nodules throughout the lungs (FIG. 24B) in numbers similar to those of the much larger L9 and CHO-WT metastases. The growth of B9 metastatic tumors relative to L9 and CHO-WT tumors was clearly inhibited, however, and survival of B9-injected animals was prolonged. It appears, therefore, that the transfected MIS gene, while markedly inhibiting cell growth, may affect less significantly the ability of the cell to implant.

To test the hypothesis that the MIS gene was responsible for inhibiting metastases of B9 cells, exogenous rhMIS was delivered intraperitoneally before injection of human ocular melanoma cells, whose growth has been shown to be inhibited by MIS in vitro and in vivo (Parry, R. L., et al., Cancer Res. 52:1182–6 (1992)). Reductions in the number of surface metastases and the percent of total lung area involved with tumor were observed in animals treated with rhMIS via intraperitoneal Alzet pumps (FIGS. 25A and 25B). Serum MIS levels were not measured during pump delivery to avoid loss of the animals during this lengthy experiment; however, serum levels achieved in recent studies when similar amounts of MIS were delivered via Alzet pumps were 0.5–0.7 nM (Parry, R. L., et al., Cancer Res. 52:1182–6 (1992)). The 400 fold higher concentrations required to produce in vitro effects (200 nM, see colony inhibition assay) may be related to more efficient molecular processing, in vivo, to produce a cleaved, biologically active form of the molecule (MacLauglin D. T., et al., Endocrinology 131(1):291–296 (1992)) (or that the lung possesses an endogenous enzyme capable of cleaving the MIS). The fact that the metastases of OM431 cells transfected with the MIS gene were markedly suppressed when compared to metastases of wild type untransfected OM431 cells provides important additional evidence for the growth inhibitory effect of MIS on the non Müllerian ocular melanomas.

The results of the ocular melanoma tail vein assay have potential clinical ramifications that are actively being investigated in our laboratory. It will be critical to determine if MIS inhibits a cell's ability to break off and migrate from the original tumor, to invade the circulation and implant, or to grow after implantation. Control of cell growth by treatment with rhMIS would certainly be of benefit in the treatment of localized ocular melanoma, but if fragmentation, invasion, or implantation are also affected, the near 100% mortality associated with metastatic disease (Char, D. H., *Am. J. Oph.* 86:76–80 (1978)) could be improved as well.

In summary, the biological modifier Müllerian Inhibiting Substance has the ability to inhibit cell growth and metastases in vitro and in vivo. Its effect can be produced by either the addition of exogenous rhMIS or transfection of the human MIS gene. The availability of cell lines engineered to produce processed, secreted, and biologically active or inactive MIS is currently permitted us to screen for critical "downstream" effects of this hormone, such as changes in cell surface and adhesion molecules, growth factors and their receptors, oncogene and tumor suppressor genes, and essential cell cycle factors. It is not clear, however, whether MIS is secreted from the transfected cell, with inhibition mediated via a receptor-transduced second messenger, or whether intracellular trafficking and nuclear translocation of MIS or MIS fragments occurs (Catlin, E. A., Müllerian Inhibiting Substance Binding Protein Localization. *Developmental Dynamics* (formerly *Am J. Anat.*), 1992, in press). Further studies involving mutations which prevent secretion from the cell may answer this question. Finally, we feel that targeted gene therapy of certain human tumors with the MIS gene deserves intensive investigation.

EXAMPLE 5

Materials and Reagents

Epidermal Growth Factor (EGF), tissue culture grade, was purchased from Sigma Chemical Co. (St. Louis, Mo.) as a lyophilized powder extracted from the submaxillary glands of male mice (Savage et al., *J. Biol. Chem.* 247:7609 (1972)). It was reconstituted in sterile pyrogen-free distilled water to a final concentration of 100 µg/ml, sub-aliquoted and stored at –70° C. γ-interferon was purchased from Amgen Biologicals (Thousand Oaks, Calif.), as a lyophilized powder and dissolved in sterile pyrogen-free water to a final concentration of 1000 units/ml *E. coli* endotoxin (Rudbach, et al., *J. Clin. Microbiol.* 3:21–25 (1976)). Human recombinant MIS (Cate et al., *Cell* 45:685–698 (1986)) was purified using a recent adaptation (Pepinsky et al., *J. Biol. Chem.* 263:18961 (1988)) of previously described methods of immunoaffinity purification (Shima, H., et al., *Hybridoma* 3:201–214 (1984); Vigier, B. et al., *Endocrinol.* 114:1315–1320 (1984).

EXAMPLE 6

Growth of Cells

CHO cells, transfected with the gene for human MIS, and amplified by Methotrexate selection (Cate et al., *Cold Spring Harbor Symposium on Quantitative Biology* vol. LI, (1986)) were grown to confluence in four liter bioreactors on stainless steel coils in alpha-Modified Eagle's Medium, supplemented with 10% fetal calf serum, Streptomycin, Gentamicin, L-Glutamine, and Pyruvate. After reaching equilibrium the medium was collected every 3–4 days, then concentrated 20% on a Minitan ultrafilter (Millipore) with a 30,000 d molecular weight cutoff membrane and stored at –70° C.

EXAMPLE 7

Purification of MIS

For purification of MIS, media were thawed and filtered through Whatman #4 filter paper to remove debris. The filtrate was then loaded, at 1 column volume/hour, on a 5 ml immunoaffinity column consisting of 32 mg of an anti-human MIS monoclonal antibody. Suitable antibodies, and methods for using them to purify MIS are disclosed in Donahoe, P. K., U.S. Pat. No. 4,487,833, herein incorporated by reference. The antibody was covalently attached to Affigel-10 agarose resin (BioRad), and equilibrated in PBS. After loading, the column was washed with Phosphate Buffered Saline (PBS) until the absorbance at 280 nm returned to baseline, then eluted with 0.015M $Na_2PO_4$, 0.15M NaCl, 2M $NH_4SCN$, pH 6.3. Fractions containing optimal MIS protein, as measured by $A_{280}$, an enzyme-linked immunoad sorbant assay (ELISA) for MIS, and western blot analysis after electrophoresis (Cate et al., *Cold Spring Harbor Symposium on Quantitative Biology* vol. LI, (1986)) were desalted on a Sephadex G-25 column (PD-10, Pharmacia) equilibrated and run in 0.02M HEPES, 0.015M NaCl, 10% Glucose, pH 7.4, and optimal fractions collected, pooled, aliquoted, and stored at –70° C. for future use (Pepinsky et al., *J. Biol. Chem.* 263:18961 (1988)). Bands which cross blotted with a polyclonal antibody to MIS represented 95% of the preparation. The predominant bands at 70 and 55 Kd representing an estimated 30% of the preparation had the predicted amino acid composition and $NH^2$ terminal sequence of human MIS (Cate et al., *Cell* 45:685–698 (1986); Pepinsky et al., *J. Biol. Chem.* 263:18961 (1988)). The immunoaffinity purified rMIS preparations (IAP 38 and 50) used in these experiments were found to have protein concentrations of 335 µg/ml and 399 µg/ml as determined by Bradford analysis (Bradford, M. M., *Anal. Biochem.* 72:248–254 (1976)). At a 1/80 dilution, both were found to cause maximal or 5+ regression of the M üllerian duct in an organ culture bioassay (Donahoe, P. K. et al., *J. Sura. Res.* 23:141 (1977); Donahoe et al., *Biol. Repro.* 16:238 (1977)) and to have a final MIS concentration of 300–400 µg/ml by ELISA. The estimation of MIS in the predominant 70 and 55 Kd bands was 170–200 µg/ml.

EXAMPLE 8

Animals and Fibroblasts Preparation

C57BL/6 (H2b) mice acquired from Jackson labs were mated in a virus free environment; the presence of a vaginal plug was taken as day 0 of pregnancy. Pregnant females were sacrificed and the fetuses harvested under sterile conditions by cesarean section on day 18 of gestation, then decapitated and minced, and the homogenate for each fetus passed through a 6 cc syringe without needle into a sterile 100 ml media bottle with 10 ml of media made 0.25% with trypsin on a stir plate at room temperature for 1 hour. Two pregnant dams with approximately 10 fetuses/dam provide sufficient cells for 20–30 flasks. The trypsin was deactivated by the addition of 10 ml of fetal calf serum and the suspension strained through a sterile funnel containing gauze to remove large particulate matter. The solution was then subdivided into 50 ml conical tubes with 7 ml of media and spun for 5 min. at 2000 9 in a desktop centrifuge, after which the supernatant was discarded and the pellets recovered, pooled and resuspended in 25 ml of media (Dulbecco's modified Eagle's media, 10% fetal calf serum, 0.01M Hepes, pH 7.4, 10,000 units penicillin and streptomycin). Cells were counted in a hemocytometer and viability determined by trypan blue exclusion. 75 cc tissue culture flasks were then seeded at a concentration of $4 \times 10^6$ viable cells (primary fibroblasts) prior to incubation at 37° C. in 5% $CO_2$ with saturated humidity for 24 hours, when media was changed. The cells were then allowed to grow to confluency (6 days). Each flask was treated with 5 ml of 0.25% trypsin-EDTA for 5 minutes at 37° C., followed by inactivation with 5 ml of 10% fetal calf serum. Cells were pooled, centrifuged for 5 min. at 2000 g, and the pellets harvested and after testing viability, resuspended in media at a concentration of $4 \times 10^6$ cells (secondary fibroblasts) in 25 cc per 75 cc flask. The media was changed at 24 hours to remove suspended cells and the adherent cells (secondary fibroblasts) grown to confluency for approximately 48 hours when 10 cc of media was aspirated and 10 cc new media added. The cells were allowed to continue their growth, and 2 days later various growth factors or lymphokines at the following concentrations were added to each flask, alone or in combination: X-interferon (250 IU/ml, 500 IU/ml and 1000 IU/ml), epidermal growth factor (EGF) 1 µg/ml, human recombinant Müllerian Inhibiting Substance (MIS) 1–1.25 µg/ml, and endotoxin 16 pg/ml. The experiment was terminated 48 hours after addition of the growth factors/lymphokines when viability was again tested with trypan blue.

EXAMPLE 9

RNA Isolation and Northern Analysis

Total RNA was prepared by extracting secondary fetal fibroblasts with guanidinium thiocyanate with β-mercaptoethanol according to the method of Chirgwin, J. M., et al. (*Biochemistry* 18:5294 (1979)). The concentration of all RNA samples was determined spectrophotometrically and by electrophoresis on a 2% agarose test gel stained with ethidium bromide to confirm that equivalent amounts of RNA would be loaded on subsequent gels.

Samples of total RNA (10 mg) were heated to 55° C. for 15 minutes in 50% deionized-formamide. 2.2M formaldehyde in 5× running buffer (0.02M morpholinopropane-sulfonic acid, pH 7.0, 50 mM sodium acetate, 5 mM EDTA, pH 8.0), placed on ice, then fractionated by electrophoresis (100 V, 4 hrs.) on a 1.0% agarose gel consisting 2.2M formaldehyde in 1× running buffer. The gel was washed in 25 mM $Na_3PO_4$, pH 6.3, for 20 minutes 3 times, transferred to Gene Screen (New England Nuclear) overnight in the same buffer, and the RNA then u.v. crosslinked to the filter.

Filters were prehybridized at 65° C. for 1 hour in 0.2% polyvinylpyrrolidone (MW=40,000), 0.2% Ficoll (MW=400,000), 0.2% bovine serum albumin, 0.05M Tris HCl, pH 7.5, 1M NaCl, 0.1% sodium pyrophosphate, 1% sodium dodecyl sulfate with 0.1 mg/ml yeast transfer RNA (tRNA). Hybridization was carried out in the same buffer with 0.1 mg/ml yeast tRNA and 10% dextran sulfate at 65° C. overnight. Filters were washed 2 times in hybridization buffer, then once with 1× SSC (0.15M NaCl/0.01M Na citrate), and twice with 0.5× SSC/0.05% SDS, all at 65° C.

A cDNA probe was selected to analyze for the presence of Class I mRNA. The Class I probe was a nick translated 2.3 kb Bam fragment which contained the 4th exon encoding the 3rd external domain of the $H-2K^b$ gene and hybridized to all Class I genes (Weiss E. et al., *EMBO J.* 2:453 (1983)). The filters were placed on Kodak X-AR film and the autoradiograms were developed in 48 hours. Rehybridization was carried out after washing filters in 0.005M Tris HCl, pH 8.0, 0.0002M $Na_2EDTA$, 0.5% sodium pyrophosphate, 0.002% polyvinyl-pyrrolidone, 0.002% bovine serum albumin, 0.002% Ficoll at 65°–70° C. for 2–3 hours with constant agitation. Filters were placed on film for 2–6 hours to confirm that the previous label was adequately washed off.

EXAMPLE 10

Roles of MIS and EGF in MHC mRNA Expression

These studies demonstrate that the growth factor EGF down-regulates the expression of Class I MHC mRNA transcripts in fetal tissue and conversely that the fetal inhibitor MIS up-regulates the same expression. Although it is known that tumor necrosis factor, endotoxin, and lymphokines may up-regulate Class I, this function has never been attributed to fetal growth inhibitors like MIS.

Growth inhibitors like MIS and growth factors such as EGF may exert their control over embryonic growth through a common pathway such as MHC. Class I MHC, ubiquitously expressed on the surface of all cells, was first referred to as "transplantation antigen", since it was permissive in the recognition of non-self, by participation in the presentation of associated processed antigen for recognition by cytotoxic T-cells.

Responses to different allografted or xenografted MHC molecules are brisk and devastating, and result in activation of cytotoxic T cells and cell lysis. It has not previously been recognized that responses to levels of autologous MHC within the same organisms might be different, and that this ubiquitous surface protein might serve a function in a more basal capacity. One aspect of the present invention is that MHC antigens act as a chemostat to precisely modulate growth, with high levels of expression resulting in or correlating with periods of slow or no growth, and low levels of expression resulting in or correlating with proliferative growth or migration. Over expression might lead to atresia in the embryo or neonate as opposed to the more proliferative autoimmune response seen in the adult; under expression could lead to controlled growth in the embryo and immature organism, and to uncontrolled growth in the form of neoplasia in the older organism. MIS is cleaved at a monobasic consensus cleavage site at amino acid 427 into an N-terminal and a C-terminal fragment which are then held in noncovalent dissociation (Pepinsky et al., *J. Biol. Chem.* 263:18961 (1988)). Some mechanism for complete dissociation, as seems to be required for TGF-B, may also be required for MIS to exert its biologic activity in the MIS organ culture assay which detects hullerian duct regression (Donahoe et al., *J. Surg. Res.* 23:141 (1977)). The large numbers of mixed mesenchymal and epithelial cells present in the early secondary fetal fibroblast preparation may provide the necessary cleavage enzymes to activate MIS in vitro to produce this response, namely up-regulation of hHC. Of the heterogeneous group of cells comprising secondary fetal fibroblasts, it is not known which proportion of the cell population responds to MIS. Cell separation techniques are underway both to determine whether the mRNA is translated into protein and to identify and immortalize those cell types which bind MIS. We suspect that these cells are fibroblasts, but can not yet rule out that a small population of lymphocytes or dendritic like cells may not be initiating this response.

Other growth factors such as insulin, insulin like growth factors, NGF, or FGF; and growth inhibitors such as tumor necrosis factor which is known to up-regulate Class I in other systems; TGF-B and inhibin, with known homology to MIS; and other lymphokines in addition to γ-interferon, may also function in this system.

Up-regulation of MHC mRNA has not been demonstrated with other substances like MIS which are known to be growth inhibitors or fetal inhibitors. Since gonadal steroids are thought to alter immunity, and are known to affect MIS, i.e., estrogen inhibits (Hutson et al., *J. Ped. Surg.* 17:953–959 (1982)) and testosterone and progesterone enhances MIS (Ikawa et al., *Gen. Comm. Endocrinol.* 87:88–102 (1985)) at the receptor level, these steroids may act to modulate the Class I mRNA effect.

Gel shift analysis can be done to determine if a specific transacting nuclear protein under the influence of MIS or EGF or ocogene much as myc, fos, or jun binds to the enhancer region of the MHC genes, to further understand factors which control growth in this fetal system.

It is possible that the modulation of MHC expression is a highly regulated initiator of cell killing which may play an important role in growth control and fetal development by participating in the internal milieu of embryonic tissue remodelling where extensive "programmed cell death" occurs, rather than being limited only to cell killing in response to foreign stimuli.

It is customary to ascribe to the T cell antigen receptor repertoire the role of tolerance which infers complete all or none negative selection and thus lack of reactivity to self components of MHC due to clonal deletion. It is, however, one aspect of the present invention that a more graded recognition of self MHC, either naked or linked to processed antigen, acting as a chemostate to signal a response with lymphokines, is another important mechanism to control growth and development.

EXAMPLE 11

Expression of MHC Antigens in Mature and Immature Tissues

Immature and mature kidney and testis were studied in three ways, (1) a functional assay of graft survival of tissues implanted beneath the kidney capsule of congenic hosts, (2) measurement of Class I and II histocompatibility antigens mRNA, using cDNA or oligonucleotide probes and northern analysis, both during ontogeny and after implantation, and at the same time, (3) detection of MHC Class I and II protein by immunohistochemical techniques.

A. RNA isolation and mRNA analysis of fetal, newborn, and grafted tissue

C57BL/6 female mice were mated with C57BL/6 males and the presence of a vaginal plug was taken as day 0 of pregnancy. Pregnant females were sacrificed and fetuses were obtained by Caesarean section on days 14 and 18 of gestation. Some pregnancies went to term and animals were selected at one and six days of age. Kidneys were excised from 14-day and 18-day fetuses, 1-day and 6-day postnatal animals, as well as the mothers. Testes were excised from the 18-day fetuses, 1-day postnatal animals, and adult males. All tissues were flash frozen and stored in liquid nitrogen for RNA determinations.

Total RNA was prepared from adult kidney (230 mg, 1.5 kidneys), adult testis (190 mg, 2 testes), and pooled tissue of 6-day postnatal kidney (300 mg, 13 kidneys), 1-day postnatal kidney (300 mg, 37 kidneys), 1-day postnatal testis (160 mg, 400 testes), 18-day fetal kidney (290 mg, 50 kidneys), 18-day fetal testis (160 mg, 410 testes), and 14-day fetal kidney (360 mg, 1000 kidneys), using guanidinium thiocyanate (Chirgwin J. M. et al., *Biochemistry* 18:5294 (1979)). The concentration of all RNA samples was determined spectrophotometrically and by electrophoresis on a 2% agarose test gel stained with ethidium bromide to confirm that equivalent amounts of RHA would be loaded on subsequent gels. Samples of total RNA (10 mg) were heated to 55° C. for 15 minutes in 50% deionized formamide, 2.2M formaldehyde, and 5× running buffer (0.2M morpholinopropanesulfonic acid, pH 7.0, 50 mM sodium acetate, 5 mM EDTA, pH 8.0), placed on ice, then fractionated by electrophoresis (100 V, 4 hrs.) on a 1.0% agarose gel containing 2.2M formaldehyde in 1× running buffer. The gel was washed in 25 mM $Na_3PO_4$, pH 6.3, for 20 minutes 3 times, transferred to Gene Screen (New England Nuclear) overnight in the same buffer (Maniatis T. et al., In: *Molecular Cloning: A Laboratory Manual*, Cold Spring Harbor Laboratory, Cold Spring Harbor, N.Y., (1982)), and the RNA then UV crosslinked to the filter. Filters were pre-hybridized at 65° C. for 1 hour in 0.2% polyvinylpyrrolidone (MW= 40,000), 0.2% Ficoll (MW=400,000), 0.2% bovine serum albumin, 0.05M Tris HCl, pH 7.5, 1M NaCl, 0.1% sodium pyrophosphate, 1% sodium dodecyl sulfate with 0.1 mg/ml yeast transfer RNA (tRNA). Hybridization was carded out in the same buffer with 0.1 mg/ml yeast tRNA and 10% dextran sulfate at 65° C. overnight. Filters were washed 2 times in hybridization buffer, then once with 1x SSC (0.15M NaCl/ 0.015M Na citrate), and twice with 0.5× SSC/0.5% SDS, all at 65° C.

Probes were selected to analyze for the presence of Class I, and Class II MHC mRNA. The Class I probe was a nick-translated 2.3 kb BamHI fragment containing the 4th exon encoding the 3rd external domain of the $H-2K^b$ gene, and hybridizes to all Class I genes (Weiss, E., et al., *EMBO J.* 2:453 (1983)). The Class II probe was a nick-translated 1.6 kb Bam-Hind III fragment, containing the 3rd exon encoding the 2nd external domain of the β-chain of the I- $A_{,β}$ gene (Larhammar D. et al., *Cell* 34:179 (1983)). The filters were placed on Kodak X-AR film and the autoradiograms were developed in 48 hours. Re-hybridization was carried out after washing filters in 0.005M Tris HCl, pH 8.0, 0.0002M $Na_2EDTA$, 0.05% sodium pyrophosphate, 0.002% polyvinyl-pyrrolidone, 0.002% bovine serum albumin, 0.002% Ficoll, at 65°–70° C. for 2–3 hrs with constant agitation. Filters were placed on film for 24 hours to confirm that the previous label was adequately washed off.

B. Morphometic and histologic analysis of grafted tissue

A functional assay of graft survival in congenic mice was based upon methods of tissue implantation, internal graft measurement, and morphometric and histologic assessment adapted from techniques used previously for developmental (Donahoe P. K., et al., *J. Ped. Surg.* 19:863 (1984)), ontologic (Fingert, H., et al., *Canc. Res.* 47:3824 (1987)), and immunologic (Foglia R. P. et al., *Annals of Surgery* 204:402 (1986); Foglia, R. P., et al., *J. Ped. Surg.* 21:608 (1986); Statter M. B. et al., *J. Urol.* 139:204 (1988)) studies in allogeneic rodents. Mouse donor tissue consisted of C57BL/6 adult, 18-day fetal, and 14-day fetal kidney; and adult, 1-day postnatal, and 18-day fetal testis. Excised kidneys or testes were placed in Dulbecco's Modified Eagle's Medium at 4° C., and divided under a dissecting microscope into 1 mm fragments. Adult recipient B10.A mice were anesthetized and the graft tissue was inserted under the left kidney capsule with a 16-gauge trocar. The long(L) and short(W) axes of the grafts were measured at 10× magnification, at a standard focal distance using a microscope equipped with a calibrated eyepiece, where 10 ocular micrometer units equal 1 mm (Foglia, R. P., et al., *Annals of Surgery* 204:402 (1986); Foglia, R. P., et al., *J. Ped. Surg.* 21:608 (1986)). Kidney and testis grafts from congenic mice after 7 and 10 days of implantation, respectively, were again measured for change in size and architecture, and lymphocytic infiltrate evaluated (FIG. 1) as previously reported for outbred rats (Foglia R. P. et al., *Annals of Surgery* 204:402 (1986); Foglia, R. P., et al., *J. Ped. Surg.* 21:608 (1986); Starter, M. B., et al., *J. Urol.* 139:204 (1988)). These intervals were chosen to equate the degree of lymphocytic infiltrate at a time before rejection is complete. Syngeneic grafts were used to control for the effects of tissue manipulation on graft size ratio and histology. B10.A 18-day and 14-day fetal renal, and adult and 18-day fetal testicular grafts were implanted for 7 days and 10 days beneath the renal capsule of adult recipient B10.A mice, and evaluated for change in size, architecture, and lymphocytic infiltrate.

The data for graft size ratio and the bioassays of graft architecture and lymphocytic infiltrate were summarized as mean±standard deviation. A logarithmic transformation (log10) was performed on the graft size ratios. An analysis of variance was used to compare the means of the groups for each variable (i.e. graft size ratio logarithmically transformed, graft architecture, and graft infiltrate). Tests of significance of these means involves simultaneous Bonferroni t-tests, in which an overall significance level of 0.05 is preserved by performing each individual test at a level of significance equal to 0.05 divided by the number of determinations made. Two-sample t-tests were used to compare the sizes attained by the respective sets of grafts. The architecture and infiltrate data were tested against the constant value, 1, which was assigned to grafts that demonstrated no evidence of rejection.

EXAMPLE 12

Implantation Studies

Analysis of Donor and Recipient Specific mRNA Expression

Class I and Class II transcripts were studied in kidney and testis grafts after implantation. Total RNA was prepared from 14-day fetal renal grafts (n =205) implanted for 7 days, 18-day fetal renal grafts (n=115) implanted for 5 days, 18-day fetal testis grafts (n=113) implanted for 10 days, and 18-day fetal testis grafts (n=94) implanted for 20 days. Since both Class I and II transcripts can be induced by products of infiltrating lymphocytes (notably γ-interferon) (Revel, M., et al., *TIBS* 11:166 (1986)), and in an attempt to equate the degree of passenger lymphocytes, grafts that demonstrated a similar degree of lymphocytic infiltrate were chosen for comparison. Samples of total RNA were fractionated by electrophoresis and subsequently transferred to Gene Screen as described above. Filters were prehybridized at 45° C. for 1 hour in hybridization buffer (5% SDS, 100 mM NaCl, 50 mM Pipes, pH 6.8, 50 mM Na phosphate, 1 mM EDTA). Hybridization was carried out in the same buffer at 45° C. overnight. Filters were washed 2 times in hybridization buffer, then once with 3.2M tetramethylammonium chloride (TMACL), 1% SDS, all at 45° C., and then once with 3.2M TMACL, 1% SDS at 49° C.

Anti sense oligonucleotide probes specific for the respective b and k haplotypes of the Class I H-2K and Class IIIa genes were chosen to distinguish the contribution of donor and recipient transcripts to the observed signal. The Class I donor specific probe 5'-CCAGAGATCACCTGAATAGT-3' hybridizes to exon 3 (SEQ ID NO:6) of H-2K$^b$, and the recipient specific probe 5'-CCGTACATCCGTTGGAACGT-3' hybridizes to exon 3 (SEQ ID NO:7) of H-2K$^k$. The Class II donor specific probe 5'-AGCTTGCCAATTGGCCAAAC-3' (SEQ ID NO:8) hybridizes to exon 2 of A$_β$b, and the recipient specific probe 5'-ATCTTCTCAGTTGAGCAAAC-3' (SEQ ID NO:9) hybridizes to exon 2 of A$_β$k (Benoist, C. O. et al., *Cell* 34:167 (1983)).

EXAMPLE 13

Immunohistochemistry: Ontogeny and Transplantation Studies

Fetal and adult fresh and transplanted tissue were excised, rinsed in OCT compound (Ames Co., Division of Miles Laboratory, Elkhart, Ind.), and frozen in liquid nitrogen for up to 2 weeks. Eight micron sections cut on a cryostat precooled to −20° C. were mounted on 1% gelatin coated glass slides then air dried for 30 minutes in preparation for antibody localization of MHC antigen. The sections were fixed in 100% acetone for 4 minutes, washed three times in Tris buffered saline (TBS) for 30 minutes, incubated in 1% hydrogen peroxide in 50% methanol for 30 minutes to quench the endogenous peroxidase activity, and again washed three times in TBS for 15 minute, all at 4° C. After blocking with serum for 20 minutes in a moist chamber, the specimens were then blotted and covered for 45 minutes at room temperature with primary antibody (1:1000) biotinylated by the method of Hsu, S.M., et al. (*Amer. J. Clin. Path.* 75:734 (1981)).

After three washes in TBS each for 3 minutes at 4° C. the sections were incubated at room temperature with VECTASTAIN-ABC reagent (avidin DH and biotinylated Horseradish peroxidase H) for 30 minutes followed by washing, treated with diaminobenzidine 0.05% in Tris HCl and 0.01% hydrogen peroxide for 7 minutes at room temperature, then stained with Harris' alum hematoxylin for 5 seconds. After eight rinses with distilled water, the tissue was dehydrated in alcohols, cleared in xylene, and mounted in Permount. The Class II antibody used was a rat monoclonal raised to murine Ia antigen (M5/114) (Bhattacharya, A., et al., *J. Immunol.* 127:2488 (1981)) (Hybritech Inc., San Diego, Calif.) supplied as 100 µg of an ammonium sulfate fraction in 0.5 ml PBS and used at an optimal dilution of 1:100. The Class I antibody was a rat monoclonal raised to murine H2 montypic antigen (M1/42)20 (Hybritech Inc. San Diego, Calif.) supplied as 100 µg of an ammonium sulfate fraction in 0.5 ml PBS and used at a dilution of 1:100. These antibodies are class specific for a variety of inbred mice strains and apparently recognize conformational determinants present on the native Class I or II molecules (Bhattacharya, A., et al., *J. Immunol.* 127:2488 (1981); Stallcup, K. C., et al., *J. Immunol.* 127:923 (1981)).

EXAMPLE 14

Ontogeny of Expression of Class I and Class II Transcripts

Class I and II mRNA levels were much higher in kidney than in testis, and Class I mRNA was higher than Class II mRNA for each tissue. Both started at very low levels in the younger fetus and increased with age. This is observed when total kidney RNA is hybridized to the Class I H-2K$^b$ probe. The densitometry levels of adult Class I transcript, when compared to 6-day postnatal, 1-day postnatal, 18-day fetal, and 14-day fetal renal Class I transcripts were approximately 80:50:18:9:1. Hybridization of the same mRNA to the Class II I-a A$_β$b probe also revealed a higher level of expression of Class II transcripts in the adult kidney when compared to that expressed in postnatal and fetal kidney. The relative level of adult Class II transcript, when compared to 6-day postnatal, 1-day postnatal, 18-day fetal, and 14-day fetal renal Class II transcripts were 33:12:7:6:1.

Likewise, the hybridization of total testis RNA to the Class I probe showed increasing levels of Class I transcripts through ontogeny, though in all cases the kidney levels were significantly greater than those found for testis of the corresponding developmental stage. The relative levels of adult Class I transcripts when compared to postnatal and 18-day fetal testicular Class I transcripts were 7:2:1. The level of Class I transcripts observed in the adult kidney, however, was about 13× greater than that observed in the adult testis which suggests that the level of Class I transcripts from 18 day kidney was approximately an order of magnitude higher than that of testes from the same stage of development. Hybridization to the Class II probe also revealed much lower levels of Class II transcripts in the adult, postnatal, and fetal testis than those observed in the adult kidney. The adult kidney showed a level of Class II transcripts 16× greater than the level in the adult testis. The relative levels of adult Class II transcripts when compared to 1-day postnatal and 18-day fetal testicular Class II transcripts were 2:1:1.

EXAMPLE 15

Morphometric and Histologic Analysis of Grafted Tissue

A. Congenic Allogeneic Grafts

When C57BL/6 tissue was implanted under the renal capsule of adult B10.A mice, younger fetal kidney grafts grew considerably, whereas older fetal kidney grafts grew less and showed a progressive increase in lymphocytic infiltration and loss of architecture. Thus, 14-day fetal renal grafts attain a larger graft size ratio than do 18-day grafts implanted for the same 7 day interval (FIG. 27A).

Histologically, the 14-day fetal renal grafts showed mild deterioration in architecture (FIG. 27B) and a moderate lymphocytic infiltrate (FIG. 27C), whereas the 18-day grafts showed greater deterioration in architecture (FIG. 27B) and a slightly greater lymphocytic infiltrate (FIG. 27C). In contrast, adult renal grafts (n=14) did not grow and showed complete loss of renal parenchymal elements and a dense lymphocytic infiltrate throughout the graft. Older fetal and even neonatal testis implants grew as well as the younger fetal renal grafts (FIG. 27A) and showed surprisingly little loss of architecture (FIG. 27B) or lymphocytic infiltrate (FIG. 27C) in contrast to the results seen in the kidney. Adult testis grafts (n=19), like renal grafts failed to grow; they had no recognizable architecture and were densely infiltrated with lymphocytes.

B. Syngeneic grafts

Syngeneic B10.A grafts, implanted beneath the renal capsule of B10.A adult recipients for 7 days, were used to control for the effects of tissue manipulation on graft size ratio and histology. The 14-day and 18-day fetal renal and 18-day fetal testicular syngeneic grafts grew to about the same size as the 14-day and 18-day fetal renal and testicular congenic C57BL/6 grafts implanted beneath the renal capsule of B10.A adult recipients. Histologically, however, the fetal renal and testicular syngeneic grafts show excellent architecture (1±0) and no lymphocytic infiltrate (1±0) with no significant difference noted from the constant value of 1. Adult renal and testicular syngeneic grafts, as expected, did not increase in size. Histologically, there was retention of parenchymal elements and no lymphocytic infiltrate. These findings indicate that tissue manipulation had little effect on graft survival.

EXAMPLE 16

Expression of Class I and Class II Transcripts in Allogeneic Grafts after Implantation When kidney and testis grafts were studied after implantation for Class I and Class II mRNA transcripts hybridization with the donor specific H-2K$^b$ probe showed levels of Class I transcripts in the young implanted kidney and testis grafts that markedly exceeded the level observed in both the adult and fetal renal and testicular donor tissue prior to implantation indicating a high degree of induction (several orders of magnitude). Hybridization to the recipient specific Class I probe showed levels of H-2K$^k$ transcripts in the implanted kidney that were much greater than the level observed in the ungrafted recipient B10.A adult renal tissue.

Hybridization with the donor specific A$_\beta$b probe showed levels of class II transcripts in the young implanted kidney and testis grafts that were much greater than the level observed in the adult and fetal renal, and testicular donor tissue prior to implantation. Finally, as observed with the recipient specific Class I probe, hybridization to the recipient specific Class II probe revealed an induction of A$_\beta$k transcripts in the kidney and testis grafts to levels that exceed the level observed in the recipient B10.A renal tissue. Thus, grafting of fetal tissue results in a large induction of Class I and Class II mRNA from both the donor graft and the recipient kidney although these fetal grafts are not strongly rejected.

EXAMPLE 17

Immunohistochemistry

To determine whether the mRNA levels reflected the induction of Class I protein, antigen expression was assessed by immuno-histochemistry before and after implantation. Immunohisto-chemical staining in the kidney was barely detectable in the fetus, but increased with age; staining in the testis remained low throughout ontogeny in the fetus, neonate, and adult. These studies indicated that during ontogeny the level of protein reflected the level of consitutive mRNA. After implantation, surprisingly, the large induction of MHC mRNA was not reflected by a corresponding increase in protein.

A. Ontogeny of Class I and II protein in the kidney

Staining of Class I and II proteins in 18-day fetal, 3-day postnatal, and adult kidney progressively increased from negligible amounts in the fetal kidney to high levels in the adult kidney. In the 18-day fetal specimen, the little Class I present was primarily located in the medullary tubules and interstitium; the glomeruli did not stain for this antigen. The 3-day postnatal kidney had a similar pattern of distribution but slightly more prominent staining when compared to the fetal tissue. The adult renal tissue showed more intense and diffuse Class I staining of both cortical and medullary tubules and interstitial cells; the glomeruli again did not stain. Class II protein expression also increased throughout ontogeny and its pattern of distribution was similar; however, the staining was far less intense. The brain, used as a negative control, failed to stain for either Class I or Class II surface protein.

B. Class I and II proteins in the kidney after implantation

Surprisingly, the kidney protein as stained by immunohistochemistry, did not follow the pattern observed for mRNA. Five days after implantation of 18-day fetal kidney the implant showed only trace levels of Class I protein, which was virtually unchanged from that seen in the original pregrafted 18 day fetal tissue, indicating no induction of Class I protein. In contrast to the fetal kidney, the adult kidney grafted for two days was atrophic but showed an intense amount of diffuse Class I surface protein staining, far in excess of that observed in the recipient adult renal tissue. The Class II protein staining after grafting fetal tissue was minimal, again indicating no induction of Class II protein. Adult kidney grafted for two days showed an intense amount of Class II surface protein, in excess of that seen in the recipient adult renal tissue. C. Class I and II proteins in testes before and after implantation The testis Class I and II protein, as detected by immunohistochemical staining, was very weak at all stages of development, but appeared to increase slightly throughout ontogeny. The minimal staining seen is localized to the interstitium and not the seminiferous tubules. The testicular tissue after implantation showed a slight increased staining of both Class I and Class II proteins in both the fetal and adult grafts. The staining, however, was very light and never exceeded the low levels seen in the positive control adult renal tissue into which the graft has been implanted. The induction manifested at the mRHA level was not observed in the protein. Adult testis grafts never acheived the intensity of staining seen in adult kidney implants.

EXAMPLE 18

Fetal Tissue as Initiator in Immune Response

In an attempt to understand the factors which allow the fetus to escape rejection although half of its antigenic endowment is paternal, we focused on fetal tissue as the donor or initiating arm of the immune response. Two fetal tissues which were shown in outbred allograft experiments to survive moderately (fetal kidney (Foglia, R. P., et al., *Annals of Surgery* 204:402 (1986); Foglia, R. P., et al., *J. Ped.* 21:608 (1986)) or extremely well (fetal or neonatal testis (Statler, M. B., et al., *J. Urol.* 139:204 (1988)), were studied in H-2 congenic mice using subrenal capsule implants. Survival in this functional transplantation assay was correlated with constituitive and induced expression of major histocompatibility complex (MHC) Class I and II mRNA or protein at increasing ages both before and after transplantation. Testis and kidney were compared to see if the mechanisms of regulation in developing tissues would be tissue specific or universal, with the expectation that some insight might be gained into the sites at which one could intervene therapeutically to regulate the MHC. Using northern analysis, we have shown differences between the testis and kidney at all ages in the constituitive expression of Class I and Class II transcripts. Adult mouse kidney has higher levels of Class I and Class II mRNA transcripts than the adult mouse testis. We also showed a progressive increase during ontogeny from very low levels of mRNA in fetal testis and kidney from the later third of gestation, to much higher levels of mRNA in the adult. When correlated graft survival, we observed that those tissues with low expression of MHC transcripts enjoyed better survival. The mouse testis at all ages survived longer with less rejection damage than did the kidney. The low levels of Class II proteins observed in both fetal and postnatal testicular tissue could result in a delay of infiltration of the T- helper cells necessary to initiate a cytotoxic T-cell response (Zinkernagel, R. M., et al., *Adv. Immunol.* 27:51 (1979)), and the low levels of Class I protein observed may result in reduced activity of cytotoxic T-cells (Hayry, P., *Transplantation* 38:1 (1984)). It is possible that these two organs have different populations of passenger lymphocyctes that increase with ontogeny, and that this could account for the differences in mRNA and survival.

We also measured Class I and Class II mRNA in surviving grafts after implantation. Donor specific Class I and II transcripts were induced to levels far exceeding those observed in the adult donor tissue prior to grafting (Armstrong, H. E., et al., *J. Exper. Med.* 165:891 (1987)) in 14-day fetal renal grafts implanted for 7 days, 18-day fetal renal grafts implanted for 5 days, and 18-day fetal testis grafts implanted for 10 and 20 days. These times were chosen in order to attempt to equate the degree of lymphocytic infiltrate and passenger lymphocytes (Lafferty, K. J., et al., *Ann. Rev. Immunol.* 1:143 (1983)). The induction of donor specific mRNA was thought to be due to the infiltration of recipient T-cells into the donor grafts and subsequent lymphokine induction. Thus, graft survival in the face of this degree of mRNA induction was unexpected. We obtained some understanding of the reason for graft survival when we attempted to detect the expression of mature protein by immunohistochemistry. Ontogeny studies of various ages showed low levels of immunostaining for fetal kidney and testis Class I protein, which increased with age and peaked in the adult. Class II constituitive antigen likewise increased with age, but never reached the intensity seen with Class I, thus correlating with the lower levels and the trends seen for mRNA production in the developing testis and confirming the preponderence of Class I over Class II for both organs. When fetal kidney was implanted beneath the subrenal capsule of the H-2 congenic host, we expected to see intense staining for MHC protein that paralleled the dramatic induction of mRNA seen on Northern analysis. Surprisingly, MHC proteins were not recognized by immunohistochemical techniques. The class specific monoclonal antibodies, however, recognized Class I and II proteins in the adult recipient kidneys into which the grafts were inserted and which served as a positive control. Survival of these allotransplants (FIG. 27) thus correlates with the deficiency of Class I and II protein expression, and indicates that some early post-transcriptional event, possibly either translation, association of polypeptide chains, or proper folding of the protein, has failed to take place to complete the process of protein maturation. Since these histochemical techniques should allow detection of both intracellular and extracellular native protein (Bhattacharya, A., et al., *J. Immunol.* 127:2488 (1981); Stallcup K. C. et al., *J. Immunol.* 127:923 (1981)), these results imply a very early block in the processing of the protein. The artifact of proteolysis can be ruled out in the grafted fetal tissue since the adult kidney implanted into the adult host stained intensely, despite a more marked lymphocytic infiltrate and rejection response. The differential induction between mRNA and protein for Class I and II in transplanted tissue is real and not due to a differential sensitivity of Northern analysis for mRNA and immunohistochemistry for protein. As can be observed in Class I and II mRNA for the adult host (B10.A) kidney, was very low compared to that of induced implanted fetal grafts; the fetal grafts however did not stain for Class I and Class II protein, whereas the host kidney stained quite well. Thus, fetal kidney and testis respond to induction signals at the mRNA level, but not at the level of MHC protein expression.

Ontogeny studies that correlate prolonged graft survival with low expression of Class I and II mRNA or protein, may be able to predict which organs might enjoy a favored status as immunopriviledged donor tissue. Immature tissue has a lower constituitive level of MHC, and like adult tissue, it can be induced to express high levels of mRNA. Unlike the adult, however, MHC protein is not induced. An understanding of the mechanism by which specific fetal and neonatal tissues escape rejection permits one to devise therapeutic strategies for prolonging survival of adult tissue grafts.

These studies suggest that modulation of donor tissue MHC expression can be used to prolong transplanted grafts, in addition to the currently used modulation of recipients' immune response, and lead to the concept of reducing the MHC burden of the donor tissue as an important part of immunotherapy.

Growth factors such as EGF, TGF-a and PDGF, and inhibitory factors such as Müllerian Inhibiting Substance (MIS) and TGF-b, which are important growth modulators in the fetus, can be expected to modulate expression of MHC transcripts or proteins. With respect to tumor tissues, it has been shown for example, that certain malignant tumors have markedly reduced or nondectable levels of Class I mRNA when compared to their normal cellular counterparts (Tanaka, K., et al., *Science* 228:26 (1985)). The lessons learned from a study of how the fetus regulates expression of MHC thus have broader applications to transplantation biology, tumor immunology, and reproductive immunology. In particular, it appears that fetal and newborn testis, like the brain (Gibson, M. J., et al., *Science* 225:4665 (1984)), is immunopriviledged, not only as a recipient, but as a donor, and thus is useful in clinical transplantation.

EXAMPLE 19

Preparation of Anti-Human MIS Monoclonal Antibody

The ability to measure MIS is clinically important in assessing the usefulness of MIS in treating malignancies (Fuller et al., *J. Clin Endo. Metab.* 54:2051 (1982)) and in determining the nature of MIS' role in fetal and postnatal development. In moving towards the definition of MIS action, mono and polyclonal antibodies have been produced. We now have the capability to measure human MIS values. Measurement and quantitation of MIS can now be used as a yardstick against which to measure normal fetal as well as postnatal sexual development. Abnormal serum findings of MIS may aid in the diagnosis of silent sexual congenital abnormalities as well as in understanding other pathophysiologic processes. In cases of under production of MIS potential therapeutic supplementary measures could be installed. In more severe situations such as absent production or receptor deficits, a greater understanding will be attained which will further developmental research and eventually lessen the patient's burden.

A. Immunization and Fusion protocols

MIS was purified from conditioned media from a dihydrofolate reductase (DHFR) deficient Chinese hamster ovary (CHO) cell line (Chasin) transfected with a colinear construct of the MIS and DHFR genes (Cate et al., *Cell* 45:685–698 (1986); Cate et al., *Cold Spring Harbor Symposium on Quantitative Biology* vol. LI, (1986)). The media was concentrated and purified sequentially by serial ion exchange and carbohydrate affinity chromatography (Budzik et al., *Cell* 21:909 (1980)), and later by immunoaffinity chromatography (Mudgett-Hunter, M., *J. Immunol.* 128:1327 (1982); Shima, H., et al., *Hybridoma* 3:201–214 (1984); Vigier et al. *Endocrinol.* 114:1315–1320 (1984); Pepinsky et al., *J. Biol. Chem.* 263:18961 (1988)). Monoclonal antibodies directed against recombinant human MIS were obtained by cell fusion techniques as described by Kohler (Kohler, G. *Immunological Met.* 2:285–298 (1981), and Donahoe (Donahoe, P. K., U.S. Pat. No. 4,487,833). Polyclonal antibodies were raised by popliteal lymph node immunization in rabbits.

Ten week old (n=5), female A/J mice (Jackson Labs) were immunized with an intraperitoneal injection of 5 μg human MIS mixed 1:1 with complete Freund's adjuvant (Difco Labs). The MIS used after purification by carbohydrate affinity was biologically active in an organ culture assay where 1–2 μg caused regression of the Müllerian duct. Three weeks later the mice received booster injections of the same dose of MIS mixed 1:1 in incomplete Freund's adjuvant (Difco Labs). After ten days the mice were bled from the retrobulbar sinus with Natelson capillary tubes (Monoject Scientific) and the serum anti-MIS antibody titer was assessed semi-quantitatively by EI 15A. Conventionally purified MIS was first bound to polyvinyl chloride microtiter plates (Falcon); serially diluted sera from MIS injected and uninjected mice were then added. Colorimetric conversion of 3,3',5,5' tetramethyl Benzidine TMB (ICN ImmunoBiologicals) by a goat anti-mouse IgG (H&L) horseradish peroxidase conjugate (New England Nuclear) indicated an antigen specific immune response. Spleen cells from the mouse producing the highest titer of antibody in this screening ELISA assay were selected for fusion. $S_p2/$ 0-Ag 14 hypoxanthine guanine deficient mouse myeloma cells were cycled through 20 μg/ml 8-azaguanine (Sigma) in Dulbecco's Modified Eagle's Medium DMEM containing 4.5 g/L glucose (Hazelton Labs) to assure azaguanine resistance and absence of reversion. After determining a doubling time of 12 hours, the cells were maintained at a concentration of $1\times10^5$ cells/ml and cycled so that the cells were in an exponential phase of growth prior to fusion.

Spleen cells $1\times10^8$ from injected mice with the highest titer of anti-MIS antibody were mixed with $2\times10^2$ Sp2/0 myeloma cells and centrifuged at 400× g for 7 minutes. After aspiration of the supernatant, 1.5 ml of serum free DMEM containing 41% W:V polyethylene glycol (PEG mw 1450, American Type Culture Collection) was added to the cell pellet. The mixture was pipetted for 1.5 minutes and then centrifuged for 10 minutes at room temperature in serum free DMEM to minimize PEG toxicity. The cells were resuspended in HAT-DMEM selective media containing 20% fetal calf serum (Hybridoma screened, Microbiological Associates Bioproducts), 200 mM L-Glutamine, Hypoxanthine $10^{-2}$ M (H), Aminopterin $4\times10^{-5}$ M (A), Thymidine $1.6\times10^{-3}$ M (T), and Penicillin/Streptomycin 2000 U/2 mg/ml (all from Sigma). The cells were then transferred to ten 96 well tissue culture plates (Falcon) which had been plated previously with a macrophage feeder layer (10,000 cells/well) obtained from 6 age matched female A/J mice by peritoneal lavage with 5 ml of cold 11.6% sterile sucrose.

The plates were placed in a 37° C. incubator in an atmosphere of 6.5% $CO_2$ in air and left undisturbed for 7 days, after which the media was replaced with HT-DMEM. Fifteen days later, hybridoma media that gave an absolute optical density value two times that of the media control as assessed by ELISA were considered positive. The hybridoma cells producing anti-MIS antibody were simultaneously expanded to the 24 well level and subcloned by limiting dilution. Mixed populations of hybridomas were frozen during incremental expansion to safe-guard against overgrowth by non-producers. Previous experience indicated improved viability after thawing if the total number of cells had been increased to $1\times10^5$ prior to freezing and storage in liquid nitrogen. Two monoclonals, M10.6 and 6E11, were developed for use in detecting MIS from various sources.

B. Immunoglobulin Class and Chain Identification

Immunoglobulin heavy and light chains were identified by using the ZYMED MonoAb-ID EIA Kit. Purified MIS bound to microtiter plates was incubated with purified antibody for 1 hr at 37° C., following which class and chain specific horseradish peroxidase conjugated antibodies were added. ABTS(2,2-azino-di [3-ethyl benzthiazoline sulfonic acid]) was used as a substrate for color development. Polyclonal Antisera Polyclonal antisera to human recombinant MIS were raised in female New Zealand White rabbits by popliteal lymph node injection. Evans blue dye was injected via the footpad of New Zealand White female rabbits to enable visualization of the popliteal lymphatics. One hour after injection, bilateral incisions were made to expose the popliteal lymph nodes into which 20 μg of electro-eluted MIS (140K band) mixed 1:1 with complete Freund's adjuvant was injected per rabbit. Four weeks later the rabbits were given a subcutaneous booster injection on the back of 25 μg MIS in incomplete Freund's adjuvant. Four weeks later the rabbits were bled via the ear vein and titers of anti-MIS antibody were determined by ELISA using a goat anti-rabbit horseradish peroxidase conjugate. Three rabbits: 103, 104 and 848, developed anti-MIS tilers of $1/1000$ or greater as determined by ELISA.

C. Monoclonal Antibody Production

Hybridoma cells were amplified in roller bottles in Alpha Modified Eagles Media supplemented with 5% female fetal calf serum (Metrix Co, Dubuque, Iowa) to a population of $10^6$ cells/ml which produced within 48–72 hours four liters of media containing approximately 50 μg/ml of antibody, yielding 200 mg from a 4 liter fermentor. Hybridomas were also amplified as ascites in 10 week old CAF-1 mice primed 2 weeks earlier by intraperitoneal injections of 0.5 ml Pristane (Pfaltz & Bauer, Inc.). $5 \times 10^5$ hybridoma cells (M10 or 6E11) were injected intraperitoneally yielding approximately 5 ml of accumulated ascitic fluid per mouse 7–10 days later with antibody concentrations in the range of 2–10 mg/ml.

D. Antibody Purification

Antibody was precipitated from ascites, media or blood by treatment with 50% $(NH_4)_2SO_4$ for 4 hours at 4° C. After centrifugation at 8000 RPM in a Beckman J2 centrifuge for 20 minutes, the pellet was resuspended in PBS at pH 8.2 in $1/50$th the original volume and dialyzed. The antibody solution was applied slowly to a 5 ml Protein A Sepharose CL-4B (Sigma) column at 1 column volume/hour. Bound antibody was eluted with 0.1M citrate in PBS pH 3.5, then dialyzed against PBS, pH 7.4 containing 0.03% sodium azide as a preservative.

EXAMPLE 20

ELISA Measurement of Human MIS

A. Bioassay

A graded organ culture assay was used to detect MIS. The monoclonal antibody M10.6 or 6E11 or a non-specific antibody was combined at a 3:1 ratio with MIS, at a concentration (2–3 μg) which caused 3–4 plus regression of the Müllerian ducts, for an overnight incubation at 4C on a rotary shaker. Each mixture was added, after sterile filtration, to the media beneath the mullerian duct in the organ culture bioassay. Three days later Müllerian duct regression was assessed histologically.

B. Affinity Constants

MIS was radiolabelled via the chloramine T Iodination method (Greenwood, et al., *Biochem. J.* 89:114 (1963); Hutson et al., *J. Ped.* 17:953–959 (1982)). Purified antibody, M10.6 or 6E11 was first bound to Falcon polyvinyl chloride microliter plates. After the plates were blocked with female fetal calf serum, the tagged MIS was added. Determination of the affinity constants was done by measuring bound and unbound radiolabelled MIS.

C. Enzyme Linked Immunoassay of Human MIS

25 μg/ml of purified monoclonal antibody (M10 or 6E11) in a 0.05M $NaHCO_3/Na_2CO_3$ pH 9.6 buffer was applied to each well of 96 well Immulon II plate (Dynatech) and incubated overnight at room temperature. The wells were then rinsed with 4 volumes of phosphate buffered saline (PBS). Blocking buffer, 5% female fetal calf serum in PBS, was then added for 2 hours at room temperature. The plates were washed with 4 volumes of PBS, following which unknowns or samples of MIS diluted to provide a standard curve in blocking buffer were applied to the wells and incubated overnight at 4° C. for optimal binding. The wells were then washed with 4 volumes of PBS, and polyclonal antibody (whole serum) at a $1/1000$ dilution in blocking buffer was added for 1 hour at room temperature. Excess antibody was washed off with 4 volumes of PBS containing 0.05% Tween 20 (J. T. Baker Chemical Co.). Mouse anti-rabbit horseradish peroxidase (Jackson Immunoresearch Labs, Inc.) diluted $1/5000$ in blocking buffer was applied for 1 hour at 4° C. as a recorder conjugate. After washing with 4 volumes of PBS/0.05% Tween 20, the substrates; 42 mM tetramethyl benzidine in DMSO (both Sigma) diluted $1/100$ in 0.1M citrate buffer, pH 9.6, 50 μM $H_2O_2$, was added. The reaction was permitted to proceed for exactly 12.5 minutes and was stopped by the addition of 2N $H_2SO_4$. Absorbance was measured at 450 nm and plotted against protein dilutions.

EXAMPLE 21

Use of the ELISA for Human MIS

Approximately one month after the primary immunization, serum antibody levels were assessed. Mice showing the highest anti-MIS response were selected for fusion. Rabbits were also immunized with human MIS. The animals were bled via their ear veins monthly to assess their anti-MIS titer. Immunization produced rabbit titers of approximately $1/1000$.

Two monoclonal antibodies (M10.6 and 6E11) directed against recombinant human MIS were produced as described above for use in a sandwich type of Elisa. Using class and chain specific enzyme linked antibody conjugates it was determined that M10.6 was an IgG1 and 6E11 was an IgG2a, both antibodies use Kappa light chains.

Affinity constants of the two antibodies were assessed with radiolabelled MIS binding experiments. M10.6 was found to have a higher affinity than 6E11 (M10.6, Ka=$10^{-12}$M, 6E11, Ka=$10^{-9}$M) but a lower capacitance as assessed by Scatchard plots. The antibodies recognize separate epitopes located on the amino and carboxy terminal fragments. An N terminal fragment was generated by site directed mutagenesis in which a stop codon was introduced at position 427, the site of probable monobasic cleavage. M10.6 recognized the N terminal fragment generated from transfected CHO cells. The C terminal fragment was generated by acid hydrolysis of whole MIS and eluted from an M10.6 affinity column. 6E11 recognized the C terminus at greatly reduced sensitivity but not the N terminal fragment.

Since microtiter plates are notorious for binding antibody poorly we compared commercially available microtiter plates. We found that Immulon II plates bound more antibody than others. A range from 12.5 μg to 100 μg/ml of first antibody was assessed to determine the optimal concentration for binding MIS. Twenty-five micrograms of either monoclonal antibody was found to be optimal. A 5% female fetal calf serum was used as a blocking and diluting buffer. Even at 100% strength, (i.e. undiluted female fetal calf serum), neither antibody identified MIS in the serum. A standard preparation of immunoaffinity purified MIS was used to establish a standard curve ranging from 0 to 20 nanograms per mililiter. Pooled cord serum from newborn females was used as a negative control due to the near zero MIS value found in it. All standard points were diluted by automated techniques and aliquoted at −80° C. Polyclonal rabbit antisera (848 or MGH-1) were used as whole serum. That concentration or titer which gave a maximal recognition of MIS, in this case 1/1000, was chosen for use in the assay. Depending on which monoclonal antibody was used, different horseradish peroxidase conjugates were chosen as indicator third antibodies. When using M10.6 a goat anti-rabbit conjugate worked optimally at a 1/500 dilution. 6E11 was found to cross react with different lots of goat anti-rabbit conjugates and a donkey anti-rabbit conjugate. A mouse anti-rabbit conjugate which had been absorbed against mouse and human serum recognized with specificity and could be used with 6E11 optimally at a 1/5000 dilution. Lengths of incubation times were assessed and abbreviated if possible. The tetramethyl benzidine substrate concentration was constant at 42 mM in DMSO diluted 1/100 in sodium acetate buffer (0.1M), pH titrated to 4.9 with citric acid followed by the addition of 12 μmoles of 30% $H_2O_2$. Substrate reaction time was exactly 12.5 minutes immediately followed by addition of 2N $H_2SO_4$. The assay can detect picomolar quantities of MIS.

Having established the sensitivity and reproducibility of the standard curve we next looked at potential cross reactivity to other growth factors and gonadotropins to define specificity. TGFB-1 and B-2 have considerable amino acid homology with the C terminal end of MIS and are considered to be representatives of the same gene family. We found no cross reactivity of 6E11 with TGF-B1 or 2, or FSH or LH, tested at 300 fold molar excess. To further address cross reactivity of the polyclonal antibody for TGF-B, FSH, or LH a similar plate ELISA was done. Although the analytical method was less sensitive the polyclonal antibody recognized MIS but not TGF-B or the gonadotropins.

This ELISA, initially established to measure human serum MIS, was first used to monitor the quantity of the MIS protein produced by a Chinese Hamster Ovary cell line which had been transfected with the human MIS gene or various mutant constructs, and to later adapted to assess MIS levels from various clinical sources. These included serum from human umbilical cord blood; serum from premature and normal newborns and those with congenital abnormalities; serum from older normal infants and children and from those with congenital anomalies, as well as serum from normal adults; female serum collected during various stages of the menstrual cycle, ovarian follicular fluid collected during various stages of In Vitro fertilization protocols; and serum of a patient with a rare Sertoli cell MIS producing tumor. The samples were collected and immediately placed on ice during transport to the laboratory where they were stored at −80° C. until assay.

The assay permitted a determination of the range of MIS concentrations in newborn male and female sera (9–74 ng/ml in males (average of 27 individuals); 0–2 ng/ml in females (average of 12 individuals)). The assay clearly delineated male cord serum with high MIS levels from female serum in which MIS was barely detectable. Similarly serum collected from premature infants in the pediatric ICU showed elevated levels for MIS in the males and undetectable levels in the females. The MIS levels fall gradually after birth in male children and begin to rise slowly to a much lower level in the prepubescent female, to reach adult male and female levels of MIS in the 5 ng range.

An adult female patient with a sex cord or Sertoli cell tumor was first examined pre-operatively for the presence of MIS in February of 1987. A large abdominal mass as well as neck mass was excised. A pre-operative level of MIS was found to be 3.2 μg/ml. The patient underwent 3 surgical procedures to remove the tumor mass. There was a significant serum drop after the first procedure. MIS level continued to drop after the second procedure. MIS concentration correlated with tumor mass and this provided a tumor marker in this case, and thus provided a biochemical marker in this difficult case of a malignant but slow growing tumor.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

Having now fully described this invention, it will be appreciated by those skilled in the art that the same can be performed within a wide range of equivalent parameters of composition, concentrations, modes of administration, and conditions without departing from the spirit or scope of the invention or of any embodiment thereof.

---

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 327 base pairs
        ( B ) TYPE: nucleic acid
        ( C ) STRANDEDNESS: both
        ( D ) TOPOLOGY: both ( i x ) FEATURE:
    ( A ) NAME/KEY: CDS
    ( B ) LOCATION: 1..327

( x i ) SEQUENCE DESCRIPTION: SEQ ID NO:1:

| AGC | GCC | GGG | GCC | GCG | GCT | GCA | GAC | GGG | CCG | TGC | GCT | CTG | CGT | GAG | CTG | 48 |
|---|---|---|---|---|---|---|---|---|---|---|---|---|---|---|---|---|
| Ser | Ala | Gly | Ala | Ala | Ala | Ala | Asp | Gly | Pro | Cys | Ala | Leu | Arg | Glu | Leu | |
| 1 | | | | 5 | | | | | 10 | | | | | 15 | | |

| AGC | GTA | GAC | CTG | CGG | GCC | GAG | CGC | TCG | GTG | CTC | ATC | CCC | GAG | ACA | TAC | 96 |
|---|---|---|---|---|---|---|---|---|---|---|---|---|---|---|---|---|
| Ser | Val | Asp | Leu | Arg | Ala | Glu | Arg | Ser | Val | Leu | Ile | Pro | Glu | Thr | Tyr | |
| | | | 20 | | | | | 25 | | | | | 30 | | | |

| CAG | GCC | AAC | AAC | TGC | CAG | GGG | GCC | TGC | GGC | TGG | CCT | CAG | TCG | GAC | CGC | 144 |
|---|---|---|---|---|---|---|---|---|---|---|---|---|---|---|---|---|
| Gln | Ala | Asn | Asn | Cys | Gln | Gly | Ala | Cys | Gly | Trp | Pro | Gln | Ser | Asp | Arg | |
| | | 35 | | | | | 40 | | | | | 45 | | | | |

| AAC | CCG | CGC | TAC | GGC | AAC | CAC | GTG | GTG | CTG | CTG | CTA | AAG | ATG | CAG | GCC | 192 |
|---|---|---|---|---|---|---|---|---|---|---|---|---|---|---|---|---|
| Asn | Pro | Arg | Tyr | Gly | Asn | His | Val | Val | Leu | Leu | Leu | Lys | Met | Gln | Ala | |
| | 50 | | | | | 55 | | | | | 60 | | | | | |

| CGC | GGC | GCC | ACC | CTG | GCG | CGC | CCG | CCC | TGC | TGT | GTG | CCC | ACA | GCC | TAC | 240 |
|---|---|---|---|---|---|---|---|---|---|---|---|---|---|---|---|---|
| Arg | Gly | Ala | Thr | Leu | Ala | Arg | Pro | Pro | Cys | Cys | Val | Pro | Thr | Ala | Tyr | |
| 65 | | | | | 70 | | | | | 75 | | | | | 80 | |

| ACC | GGC | AAG | CTC | CTC | ATC | AGC | CTG | TCC | GAG | GAG | CGC | ATC | AGT | GCG | CAC | 288 |
|---|---|---|---|---|---|---|---|---|---|---|---|---|---|---|---|---|
| Thr | Gly | Lys | Leu | Leu | Ile | Ser | Leu | Ser | Glu | Glu | Arg | Ile | Ser | Ala | His | |
| | | | | 85 | | | | | 90 | | | | | 95 | | |

| CAC | GTC | CCA | AAC | ATG | GTG | GCC | ACC | GAA | TGC | GGC | TGC | CGG | | | | 327 |
|---|---|---|---|---|---|---|---|---|---|---|---|---|---|---|---|---|
| His | Val | Pro | Asn | Met | Val | Ala | Thr | Glu | Cys | Gly | Cys | Arg | | | | |
| | | | 100 | | | | | 105 | | | | | | | | |

( 2 ) INFORMATION FOR SEQ ID NO:2:

( i ) SEQUENCE CHARACTERISTICS:
        ( A ) LENGTH: 109 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| Ser | Ala | Gly | Ala | Ala | Ala | Ala | Asp | Gly | Pro | Cys | Ala | Leu | Arg | Glu | Leu |
|---|---|---|---|---|---|---|---|---|---|---|---|---|---|---|---|
| 1 | | | | 5 | | | | | 10 | | | | | 15 | |

| Ser | Val | Asp | Leu | Arg | Ala | Glu | Arg | Ser | Val | Leu | Ile | Pro | Glu | Thr | Tyr |
|---|---|---|---|---|---|---|---|---|---|---|---|---|---|---|---|
| | | | 20 | | | | | 25 | | | | | 30 | | |

| Gln | Ala | Asn | Asn | Cys | Gln | Gly | Ala | Cys | Gly | Trp | Pro | Gln | Ser | Asp | Arg |
|---|---|---|---|---|---|---|---|---|---|---|---|---|---|---|---|
| | | 35 | | | | | 40 | | | | | 45 | | | |

| Asn | Pro | Arg | Tyr | Gly | Asn | His | Val | Val | Leu | Leu | Leu | Lys | Met | Gln | Ala |
|---|---|---|---|---|---|---|---|---|---|---|---|---|---|---|---|
| | 50 | | | | | 55 | | | | | 60 | | | | |

| Arg | Gly | Ala | Thr | Leu | Ala | Arg | Pro | Pro | Cys | Cys | Val | Pro | Thr | Ala | Tyr |
|---|---|---|---|---|---|---|---|---|---|---|---|---|---|---|---|
| 65 | | | | | 70 | | | | | 75 | | | | | 80 |

| Thr | Gly | Lys | Leu | Leu | Ile | Ser | Leu | Ser | Glu | Glu | Arg | Ile | Ser | Ala | His |
|---|---|---|---|---|---|---|---|---|---|---|---|---|---|---|---|
| | | | | 85 | | | | | 90 | | | | | 95 | |

| His | Val | Pro | Asn | Met | Val | Ala | Thr | Glu | Cys | Gly | Cys | Arg |
|---|---|---|---|---|---|---|---|---|---|---|---|---|
| | | | 100 | | | | | 105 | | | | |

( 2 ) INFORMATION FOR SEQ ID NO:3:

( i ) SEQUENCE CHARACTERISTICS:
        ( A ) LENGTH: 327 base pairs
        ( B ) TYPE: nucleic acid
        ( C ) STRANDEDNESS: both
        ( D ) TOPOLOGY: both ( i x ) FEATURE:
        ( A ) NAME/KEY: CDS
        ( B ) LOCATION: 1..327

( x i ) SEQUENCE DESCRIPTION: SEQ ID NO:3:

| AGC | GCG | GGG | GCC | ACC | GCC | GCC | GAC | GGG | CCG | TGC | GCG | CTG | CGC | GAG | CTC | 48 |
| Ser | Ala | Gly | Ala | Thr | Ala | Ala | Asp | Gly | Pro | Cys | Ala | Leu | Arg | Glu | Leu | |
| 1 | | | | 5 | | | | | 10 | | | | | 15 | | |

| AGC | GTA | GAC | CTC | CGC | GCC | GAG | CGC | TCC | GTA | CTC | ATC | CCC | GAG | ACC | TAC | 96 |
| Ser | Val | Asp | Leu | Arg | Ala | Glu | Arg | Ser | Val | Leu | Ile | Pro | Glu | Thr | Tyr | |
| | | | 20 | | | | | 25 | | | | | 30 | | | |

| CAG | GCC | AAC | AAT | TGC | CAG | GGC | GTG | TGC | GGC | TGG | CCT | CAG | TCC | GAC | CGC | 144 |
| Gln | Ala | Asn | Asn | Cys | Gln | Gly | Val | Cys | Gly | Trp | Pro | Gln | Ser | Asp | Arg | |
| | | | 35 | | | | 40 | | | | | 45 | | | | |

| AAC | CCG | CGC | TAC | GGC | AAC | CAC | GTG | GTG | CTG | CTG | CTG | AAG | ATG | CAG | GCC | 192 |
| Asn | Pro | Arg | Tyr | Gly | Asn | His | Val | Val | Leu | Leu | Leu | Lys | Met | Gln | Ala | |
| | 50 | | | | | 55 | | | | | 60 | | | | | |

| CGT | GGG | GCC | GCC | CTG | GCG | CGC | CCA | CCC | TGC | TGC | GTG | CCC | ACC | GCC | TAC | 240 |
| Arg | Gly | Ala | Ala | Leu | Ala | Arg | Pro | Pro | Cys | Cys | Val | Pro | Thr | Ala | Tyr | |
| 65 | | | | 70 | | | | | 75 | | | | | 80 | | |

| GCG | GGC | AAG | CTG | CTC | ATC | AGC | CTG | TCG | GAG | GAA | CGC | ATC | AGC | GCG | CAC | 288 |
| Ala | Gly | Lys | Leu | Leu | Ile | Ser | Leu | Ser | Glu | Glu | Arg | Ile | Ser | Ala | His | |
| | | | | 85 | | | | | 90 | | | | | 95 | | |

| CAC | GTG | CCC | AAC | ATG | GTG | GCC | ACC | GAG | TGT | GGC | TGC | CGG | | | | 327 |
| His | Val | Pro | Asn | Met | Val | Ala | Thr | Glu | Cys | Gly | Cys | Arg | | | | |
| | | | 100 | | | | | 105 | | | | | | | | |

( 2 ) INFORMATION FOR SEQ ID NO:4:

( i ) SEQUENCE CHARACTERISTICS:
        ( A ) LENGTH: 109 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

| Ser | Ala | Gly | Ala | Thr | Ala | Ala | Asp | Gly | Pro | Cys | Ala | Leu | Arg | Glu | Leu |
| 1 | | | | 5 | | | | | 10 | | | | | 15 | |

| Ser | Val | Asp | Leu | Arg | Ala | Glu | Arg | Ser | Val | Leu | Ile | Pro | Glu | Thr | Tyr |
| | | | 20 | | | | | 25 | | | | | 30 | | |

| Gln | Ala | Asn | Asn | Cys | Gln | Gly | Val | Cys | Gly | Trp | Pro | Gln | Ser | Asp | Arg |
| | | | 35 | | | | | 40 | | | | | 45 | | |

| Asn | Pro | Arg | Tyr | Gly | Asn | His | Val | Val | Leu | Leu | Leu | Lys | Met | Gln | Ala |
| | 50 | | | | | 55 | | | | | 60 | | | | |

| Arg | Gly | Ala | Ala | Leu | Ala | Arg | Pro | Pro | Cys | Cys | Val | Pro | Thr | Ala | Tyr |
| 65 | | | | 70 | | | | | 75 | | | | | 80 | |

| Ala | Gly | Lys | Leu | Leu | Ile | Ser | Leu | Ser | Glu | Glu | Arg | Ile | Ser | Ala | His |
| | | | | 85 | | | | | 90 | | | | | 95 | |

| His | Val | Pro | Asn | Met | Val | Ala | Thr | Glu | Cys | Gly | Cys | Arg |
| | | | 100 | | | | | 105 | | | | |

( 2 ) INFORMATION FOR SEQ ID NO:5:

( i ) SEQUENCE CHARACTERISTICS:
        ( A ) LENGTH: 13 amino acids
        ( B ) TYPE: amino acid
        ( D ) TOPOLOGY: linear ( x i ) SEQUENCE DESCRIPTION: SEQ ID NO:5:

| Trp | Pro | Gln | Ser | Asp | Arg | Asn | Pro | Arg | Tyr | Gly | Asn | His |
| 1 | | | | 5 | | | | | 10 | | | |

( 2 ) INFORMATION FOR SEQ ID NO:6:

( i ) SEQUENCE CHARACTERISTICS:

(A) LENGTH: 20 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:6:

CCAGAGATCA CCTGAATAGT 20

(2) INFORMATION FOR SEQ ID NO:7:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:7:

CCGTACATCC GTTGGAACGT 20

(2) INFORMATION FOR SEQ ID NO:8:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:8:

AGCTTGCCAA TTGGCCAAAC 20

(2) INFORMATION FOR SEQ ID NO:9:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:9:

ATCTTCTCAG TTGAGCAAAC 20

What is claimed is:

1. A method of inhibiting growth of an ocular melanoma comprising administering an effective mount of Müllerian Inhibiting Substance (MIS) to inhibit ocular melanoma growth.

2. The method of claim 1, wherein the MIS is purified from an immunoaffinity chromatography matrix by eluting with an effective amount of an alkali metal halide or an alkaline earth metal halide followed by eluting with an acid solution having a pH of between about 2.5 and 4.0.

3. The method of claim 1, wherein said MIS is proteolytically cleaved with plasmin to form N-terminal MIS and C-terminal MIS protein fragments.

4. The method of claim 1, further comprising administering an effective amount of a chemotherapeutic agent following administration of the MIS, said chemotherapeutic agent effective in inhibiting growth of said tumor.

5. The method of claim 4, wherein the chemotherapeutic agent is cisplatin.

6. The method of claim 1, wherein the MIS is recombinant human MIS (rhMIS).

7. A method of inhibiting growth of an ocular melanoma comprising administering an effective mount of a combination of a chemotherapeutic agent and Müllerian Inhibiting Substance (MIS) to inhibit ocular melanoma growth.

8. The method of claim 7, wherein the MIS is purified from an immunoaffinity chromatography matrix by eluting with an effective amount of an alkali metal halide or an alkaline earth metal halide followed by eluting with an acid solution having a pH of between about 2.5 and 4.0.

9. The method of claim 7, wherein said MIS is proteolytically cleaved with plasmin to form N-terminal MIS and C-terminal MIS protein fragments.

10. The method of claim 1 or 7, wherein said MIS is administered to a patient.

11. A method of inhibiting tumor growth comprising administering an effective amount of isolated C-terminal fragment of Müllerian Inhibiting Substance (MIS) having an amino acid sequence shown in either FIG. 17 (SEQ ID NO:2) or FIG. 18 (SEQ ID NO:4) to inhibit tumor growth, wherein said tumor is selected from the group consisting of vulvar carcinoma, cervical carcinoma, endometrial carcinoma, ovarian carcinoma, and ocular melanoma.

12. The method of claim 11, further comprising administering an effective amount of a chemotherapeutic agent following administration of the C-terminal fragment of MIS, said chemotherapeutic agent effective in inhibiting growth of said tumor.

13. The method of claim 12, wherein the chemotherapeutic agent is cisplatin.

14. The method of claim 11, wherein the C-terminal fragment of MIS is derived from recombinant human MIS (rhMIS).

15. The method of claim 1 or 11, wherein primary tumor growth is inhibited.

16. The method of claim 1 or 11, wherein metastatic tumor growth is inhibited.

17. A method of inhibiting tumor growth comprising administering an effective amount of a combination of a chemotherapeutic agent and isolated C-terminal fragment of Müllerian Inhibiting Substance (MIS) having an amino acid sequence shown in either FIG. 17 (SEQ ID NO:2) or FIG. 18 (SEQ ID NO:4) to inhibit tumor growth, wherein said tumor is selected from the group consisting of vulvar carcinoma, cervical carcinoma, endometrial carcinoma, ovarian carcinoma, and ocular melanoma.

18. The method of claim 11 or 17, wherein said C-terminal fragment of MIS its administered to a patient.

19. The method of any one of claims 11 or 17, wherein said tumor is a vulvar carcinoma.

20. The method of any one of claims 11 or 17, wherein said tumor is a cervical carcinoma.

21. The method of any one of claims 11 or 17, wherein said tumor is an endometrial carcinoma.

22. The method of any one of claims 11 or 17, wherein said tumor is an ovarian carcinoma.

23. The method of any one of claims 11 or 17, wherein said tumor is an ocular melanoma.

* * * * *

UNITED STATES PATENT AND TRADEMARK OFFICE
CERTIFICATE OF CORRECTION

PATENT NO. : 5,661,126

DATED : August 26, 1997

INVENTOR(S) : Donahoe et al.

It is certified that error appears in the above-identified patent and that said Letters Patent is hereby corrected as shown below:

On the title page item [75], under "Inventors", delete "Edward M. Barksdale, Cincinnati, Ohio".

At column 78, line 52, delete "mount" and insert therein --amount--.

At column 80, line 9, delete "its" and insert therein --is--.

Signed and Sealed this

Third Day of February, 1998

Attest:

BRUCE LEHMAN

Attesting Officer

Commissioner of Patents and Trademarks